US007012075B2

(12) United States Patent
Prasit et al.

(10) Patent No.: US 7,012,075 B2
(45) Date of Patent: Mar. 14, 2006

(54) CATHEPSIN CYSTEINE PROTEASE INHIBITORS

(75) Inventors: Petpihoon Prasit, San Diego, CA (US); Christopher Ian Bayly, Beaconsfield (CA); Joel Stephane Robichaud, Dollard des Ormeaux (CA); W. Cameron Black, Baie d'Urfe (CA); Eduardo L. Setti, San Mateo, CA (US); Robert M. Rydzewski, Newark, CA (US); James T. Palmer, Corte Madera, CA (US)

(73) Assignees: Merck & Co., Inc., Rahway, NJ (US); Axys Pharmaceuticals, Inc., South San Francisco, CA (US)

( * ) Notice: Subject to any disclaimer, the term of this patent is extended or adjusted under 35 U.S.C. 154(b) by 205 days.

(21) Appl. No.: 10/469,430

(22) PCT Filed: Mar. 1, 2002

(86) PCT No.: PCT/US02/06533

§ 371 (c)(1),
(2), (4) Date: Aug. 28, 2003

(87) PCT Pub. No.: WO02/069901

PCT Pub. Date: Sep. 12, 2002

(65) Prior Publication Data

US 2004/0198982 A1 Oct. 7, 2004

Related U.S. Application Data

(60) Provisional application No. 60/272,799, filed on Mar. 2, 2001.

(51) Int. Cl.
*A61K 31/495* (2006.01)
*A61K 31/44* (2006.01)
*A61K 31/275* (2006.01)
*C07D 413/00* (2006.01)
*C07C 255/00* (2006.01)

(52) U.S. Cl. .............. 514/252.13; 514/336; 514/520; 514/521; 544/369; 558/388; 558/392; 546/268.1

(58) Field of Classification Search ........... 514/252.13, 514/336, 520, 521; 544/369; 558/388, 392; 546/268.1
See application file for complete search history.

(56) References Cited

U.S. PATENT DOCUMENTS

| | | | |
|---|---|---|---|
| 6,608,057 B1 * | 8/2003 | Cywin et al. | 514/232.8 |
| 6,617,426 B1 * | 9/2003 | Munoz et al. | 530/331 |
| 6,635,621 B1 * | 10/2003 | Singh et al. | 514/19 |
| 6,649,642 B1 * | 11/2003 | Bekkali et al. | 514/394 |
| 6,716,818 B1 * | 4/2004 | Cai et al. | 514/19 |
| 6,720,319 B1 * | 4/2004 | Liu et al. | 514/232.2 |
| 6,730,671 B1 * | 5/2004 | Cywin et al. | 514/232.8 |
| 6,756,372 B1 * | 6/2004 | Emmanuel et al. | 514/231.5 |
| 6,835,727 B1 * | 12/2004 | Okamoto et al. | 514/408 |
| 6,849,605 B1 * | 2/2005 | Shapiro | 514/19 |
| 6,858,623 B1 * | 2/2005 | Bekkali et al. | 514/304 |
| 6,878,706 B1 * | 4/2005 | Gilmore et al. | 514/237.5 |

FOREIGN PATENT DOCUMENTS

| | | |
|---|---|---|
| WO | WO99/24460 | 5/1999 |
| WO | WO 00/49007 | 8/2000 |
| WO | WO 00/49008 | 8/2000 |
| WO | WO 00/55126 | 9/2000 |
| WO | WO 01/68645 | 9/2001 |
| WO | WO 01/87828 | 11/2001 |

* cited by examiner

*Primary Examiner*—Deborah C. Lambkin
(74) *Attorney, Agent, or Firm*—Nicole M. Beeler; Mark R. Daniel

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

29 Claims, No Drawings

CATHEPSIN CYSTEINE PROTEASE INHIBITORS

This application claims the benefit of Provisional Application No. 60/272,799, filed on Mar. 2, 2001.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, *Biochrem J* 192:365–368; Delaisse, J. et al., 1984, *Biochem Biophys Res Commun:*441–447; Delaisse, J. M. et al., 1987, *Bone* 8:305–313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, F, H, L, K, S, W, and Z have been cloned. Cathepsin K (which is also known by the abbreviation cat K) is also known as cathepsin O and cathepsin O2. See PCT Application WO 96/13523, Khepri Pharmaceuticals, Inc., published May 9, 1996, which is hereby incorporated by reference in its entirety. Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immunbe responses, including, but not limited to, rejection of organ transplants or tissue grafts. Increased Cathepsin B levels and redistribution of the enzyme are found in tumors, suggesting a role in tumor invasion and matastasis. In addition, aberrant Cathpsin B activity is implicated in such disease states as rheumatoid arthritis, osteoarthritis, pneumocystisis carinii, acute pancreatitis, inflammatory airway disease and bone and joint disorders.

Cysteine protease inhibitors such as E-64 (trans-epoxysuccinyl-L-leucylamide-(4-guanidino) butane) are known to be effective in inhibiting bone resorption. See Delaisse, J. M. et al., 1987, *Bone* 8:305–313, which is hereby incorporated by reference in its entirety. Recently, cathepsin K was cloned and found specifically expressed in osteoclasts See Tezuka, K. et al., 1994, *J Biol Chem* 269: 1106–1109; Shi, G. P. et al., 1995, *FEBS Lett* 357:129–134; Bromme, D. and Okamoto, K., 1995, *Biol Chem Hoppe Seyler* 376:379–384; Bromme, D. et al., 1996, *J Biol Chem* 271:2126–2132; Drake, F. H. et al., 1996, *J Biol Chem* 271:12511– 12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to result in inactive protein. See Gelb, B. D. et al., 1996, *Science* 273:1236–1238; Johnson, M. R. et al., 1996, *Genome Res* 6:1050–1055, which are hereby incorporated by reference in their entirety. Therefore, it appears that cathepsin K is involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, *J Biol Chem* 272:13955–13960; Littlewood-Evans, A. et al., 1997, *Bone* 20:81–86, which are hereby incorporated by reference in their entirety. Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively. See Bromme, D. et al., 1996, *J Biol Chem* 271: 2126–2132; Bossard, M. J. et al.,1996, *J Biol Chem* 271: 12517–12524, which are hereby incorporated by reference in their entirety. Cathepsin K is active at a broad pH range with significant activity between pH 4–8, thus allowing for good catalytic activity in the resorption lacunae of osteoclasts where the pH is about 4–5.

Human type I collagen, the major collagen in bone is a good substrate for cathepsin K. See Kafienah, W., et al., 1998, *Biochem J* 331:727–732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109–8112, which is hereby incorporated by reference in its entirety. The crystal structure of cathepsin K has been resolved. See McGrath, M. E., et al., 1997, *Nat Struct Biol* 4:105–109; Zhao, B., et al., 1997, *Nat Struct Biol* 4: 109–11, which are hereby incorporated by reference in their entirety. Also, selective peptide based inhibitors of cathepsin K have been developed See Bromme, D., et al., 1996, *Biochem J* 315:85–89; Thompson, S. K., et al.,1997, *Proc Natl Acad Sci USA* 94:14249–14254, which are hereby incorporated by reference in their entirety. Accordingly, inhibitors of Cathepsin K can reduce bone resorption. Such inhibitors would be useful in treating disorders involving bone resorption, such as osteoporosis.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula I, and the pharmaceutically acceptable salts and stereoisomers thereof:

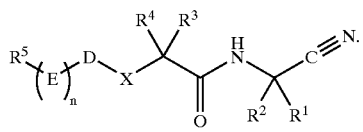

DETAILED DESCRIPTION OF THE INVENTION

The present invention relates to compounds of the following chemical formula:

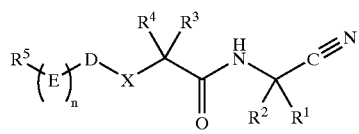

wherein $R^1$ is hydrogen, $C_{1-6}$ alkyl or $C_{1-6}$ alkenyl wherein said alkyl and alkenyl groups are optionally substituted with halo;

$R^2$ is hydrogen, $C_{1-6}$ alkyl or $C_{1-6}$ alkenyl wherein said alkyl and alkenyl groups are optionally substituted with halo;

or $R^1$ and $R^2$ can be taken together with the carbon atom to which they are attached to form a $C_{3-8}$ cycloalkyl ring wherein said ring system is optionally substituted with $C_{1-6}$ alkyl, hydroxyalkyl or halo;

$R^3$ is hydrogen, $C_{1-6}$ alkyl or $C_{1-6}$ alkenyl wherein said alkyl and alkenyl groups are optionally substituted with $C_{3-6}$ cycloalkyl or halo;

$R^4$ is hydrogen, $C_{1-6}$ alkyl or $C_{1-6}$ alkenyl wherein said alkyl and alkenyl groups are optionally substituted with $C_{3-6}$ cycloalkyl or halo;

or $R^3$ and $R^4$ can be taken together with the carbon atom to which they are attached to form a $C_{3-8}$ cycloalcyl ring, $C_{5-8}$ cycloalkenyl ring, or five to seven membered heterocyclyl wherein said cycloalkyl, cycloalkenyl and heterocyclyl groups are optionally substituted with $C_{1-6}$ alkyl, halo, hydroxyalkyl, hydroxy, alkoxy or keto;

X is selected from the group consisting of NH, $NR^6$, —$NHSO_2$—, O, —$C(R^7)(R^8)O$—, —$OC(R^7)(R^8)$—, —$C(R^7)(R^8)C(R^7)(R^8)O$—, S, $SO_2$, —$C(R^7)(R^8)S$—, —$SC(R^7)(R^8)$—, $C(R^7)(R^8)SO_2$, $SO_2C(R^7)(R^8)$—, —$C(R^7)(R^8)$—, —$C(R^7)(R^8)N(R^7)$—, —$N(R^7)C(R^7)(R^8)$—; $R^6$ is $C_{1-6}$ alkyl;

or $R^6$ and $R^4$ can be taken together with any of the atoms to which they may be attached or are between them to form a 4–12 membered heterocyclyl ring system wherein said ring system, which may be monocyclic or bicyclic, is optionally substituted with $C_{1-6}$ alkyl, halo, hydroxyalkyl, hydroxy, keto, $OR^7$, $SR^7$ or $N(R^7)_2$;

$R^7$ is hydrogen or $C_{1-6}$ alkyl;

$R^8$ is hydrogen or $C_{1-6}$ alkyl;

D is aryl, heteroaryl, $C_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from hydrogen, halogen, $C_{1-10}$ alkyl, $C_{3-8}$ cycloalkyl, aryl, aryl$C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo and $C_{1-5}$ alkylcarbonyloxy;

E is aryl, heteroaryl, $C_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from hydrogen, halogen, $C_{1-10}$ alkyl, $C_{3-8}$ cycloalkyl, aryl, aryl$C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo and $C_{1-5}$ alkylcarbonyloxy;

$R^5$ is hydrogen, $C_{1-6}$ alkyl, $C_{2-6}$ alkenyl, $C_{1-6}$ alkyloxy, halo, nitro, amino, cyano, aryl, heteroaryl, $C_{3-8}$ cycloalkyl, heterocyclyl, —$C(O)OR^7$, —$C(O)OSi[CH(CH_3)_2]_3$, —$OR^7$, —$C(O)R^7$, —$R^7C(O)R^9$, —$C(O)R^9$, —$C(O)N(R^7)(R^8)$, —$C(O)(R^7)N(R^7)(R^8)$, —$SR^7$, —$SR^9$, —$R^7SR^9$, —$R^9$, —$C(R^9)_3$, —$C(R^7)(R^8)N(R^9)_2$, —$NR^7CONR^7S(O)_2R^9$, —$SO_2R^7$, —$SO_2R_9$, —$SO_2N(R^7)(R^8)$, —$SO_2CH(R^7)(R^8)$, —$OSO_2R^7$, —$N(R^7)C(O)NR^7R^9$, —$N(R^7)C(O)R^7$, —$N(R^7)C(O)OR^7$, —$N(R^7)SO^2R^7$, —$C(R^7)(R^8)NR^7C(R^7)(R^8)R^9$, —$C(R^7)(R^8)N(R^7)R^9$, $C(R^7)(R^8)N(R^7)(R^8)$, —$C(R^a)(R^b)NR^aC(R^a)(R^b)$, —$C(R^a)(R^b)N(R^a)(R^b)$, —$C(R^a)(R^b)C(R^a)(R^b)N(R^a)(R^b)$, —$C(O)C(R^a)(R^b)N(R^a)(R^b)$, $C(O)C(R^a)(R^b)S(R^a)(R^b)$, $C(R^a)(R^b)C(O)N(R^a)(R^b)$;

wherein the above $R^5$ groups can be optionally substituted on either the carbon or the heteroatom with one to five substituents independently selected from the group consisting of $C_{1-6}$ alkyl, aryl, halo, —$OR^7$, —$O(aryl)$, —$NO_2$, —$NH_2$, —$NHS(O)_2 R^6$, —$C(R^7)(R^8)N(R^7)(R^8)$, —C($R^a$)($R^b$)C(O)N($R^a$)($R^b$), —N($R^7$)C($R^7$)($R^8$), —NH(CH$_2$)$_2$OH, —NHC(O)O$R^7$, Si(CH$_3$)$_3$, heterocyclyl and heteroaryl;

$R^9$ is selected from the group consisting of aryl, aryl(C$_{1-4}$)alkyl, heteroaryl, heteroaryl(C$_{1-4}$)alkyl, C$_{3-8}$cycloalkyl, C$_{3-8}$cycloalkyl(C$_{1-4}$)alkyl, and heterocyclyl(C$_{1-4}$)alkyl; and Ra is hydrogen, C$_{1-6}$ alkyl, (C$_{1-6}$ alkyl)aryl, (C$_{1-6}$ alkyl) hydroxyl, hydroxyl, halo, aryl, heteroaryl, C$_{3-8}$ cycloalkyl, heterocyclyl, wherein said alkyl, aryl, heteroaryl, C$_{3-8}$ cycloalkyl and heterocyclyl can be optionally substituted on either the carbon or the heteroatom with C$_{1-6}$ alkyl or halo;

Rb is hydrogen, C$_{1-6}$ alkyl, (C$_{1-6}$ alkyl)aryl, (C$_{1-6}$ alkyl) hydroxyl, hydroxyl, halo, aryl, heteroaryl, C$_{3-8}$ cycloalkyl, heterocyclyl,wherein said alkyl, aryl, heteroaryl, C$_{3-8}$ cycloalkyl and heterocyclyl can be optionally substituted on either the carbon or the heteroatom with C$_{1-6}$ alkyl or halo;

or $R^a$ and $R^b$ can be taken together with the carbon atom to which they are attached or are between them to form a C$_{3-8}$ cycloalkyl ring or C$_{3-8}$ heterocyclyl ring wherein said 3–8 membered ring system may be optionally substituted with C$_{1-6}$ alkyl and halo;

n is independently selected from an integer from one to two;

provided that when $R^1$ and $R^2$ are taken together with the carbon atom to which they are attached to form a C$_{3-8}$ cycloalkyl ring, n is independently selected from zero to two;

and provided that when $R^3$ and $R^4$ are taken together with the carbon atom to which they are attached to form a C$_{3-8}$ cycloalkyl ring, n is independently selected from zero to two;

and provided that when $R^4$ and $R^6$ are taken together with the carbon atom to which they are attached to form a C$_{3-8}$ cycloalkyl ring, n is independently selected from zero to two;

and the pharmaceutically acceptable salts and N-oxide derivatives thereof.

In an embodiment of the invention, X is N$R^6$ and $R^6$ and $R^4$ can be taken together with any of the atoms to which they may be attached or are between them to form a 4–8 membered heterocyclyl ring system wherein said ring system, which may be monocyclic or bicyclic, is optionally substituted with C$_{1-6}$ alkyl, halo, hydroxyalkyl, hydroxy, keto, O$R^7$, S$R^7$ or N($R^7$)$_2$, and n is an integer from zero to two. In a further embodiment, $R^6$ and $R^4$ form a pyrolidinyl, which is optionally substituted with the substituents mentioned above. In another embodiment, X is NH. In another embodiment of the invention X is S.

In an embodiment of the invention, D is aryl, heteroaryl, C$_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from C$_{1-6}$ alkyl, halo, —O$R^7$, haloalkyl, haloalkyloxy, cyano, amino, oxo, methylenedioxy, and nitro. In another embodiment of the invention, D is aryl, heteroaryl, C$_{3-8}$ cycloalkyl or heterocyclyl ring system selected from the group consisting of: phenyl, thiophenyl, oxazolyl, isoxazolyl, thiazolyl, isothiazolyl, triazolyl, tetrazolyl, pyridinyl, oxadiazolyl, thiadiazolyl, benzothiazolyl, benzimidazolyl, napthalenyl, or tetralinyl which is optionally substituted on either the carbon or the heteroatom with C$_{1-6}$ alkyl, halo, —O$R^7$, haloalkyl, haloalkyloxy, cyano, amino, oxo, methylenedioxy, and nitro. In a further embodiment, D is phenyl, which is optionally substituted by C$_{1-6}$ alkyl or halo.

In an embodiment of the invention, E is aryl, heteroaryl, C$_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from C$_{1-6}$ alkyl, halo, —O$R^7$, haloalkyl, haloalkyloxy, cyano, amino, oxo, methylenedioxy, and nitro. In another embodiment of the invention, E is aryl, heteroaryl, C$_{3-8}$ cycloalkyl or heterocyclyl ring system selected from: phenyl, piperazinyl, thiazolyl, benzothiophenyl, quinolinyl, isoquinolinyl, pyrazolyl, indolyl, pyrimidinyl, napthalenyl, imidazolyl, benzofuranyl, isobenzofuranyl, benzodioxinyl or furanyl which is optionally substituted on either the carbon or the heteroatom with C$_{1-6}$ alkyl, halo, —O$R^7$, haloalkyl, haloalkyloxy, cyano, amino, oxo, methylenedioxy, and nitro. In a further embodiment, E is phenyl, which is optionally substituted with C$_{1-6}$ alkyl or halo.

In an embodiment of the invention, $R^1$ and $R^2$ are both hydrogen. In another embodiment of the invention, $R^1$ and $R^2$, when on the same carbon atom, can be taken together with the carbon atom to which they are attached to form a 3–8 membered ring system wherein said ring system is optionally substituted with C$_{1-6}$ alkyl, hydroxyalkyl and halo. Examples of ring systems that can be formed include cyclopropyl, cyclobutyl, cyclopentyl, cyclohexyl and cycloheptyl. A preferred embodiment is when cyclopropyl is formed.

In an embodiment of the invention, $R^3$ is C$_{1-6}$ alkyl and $R^4$ is H. In a further embodiment of the invention $R^3$ is isobutyl and $R^4$ is H. In another embodiment of the invention, $R^3$ and $R^4$, when on the same carbon atom, can be taken together with the carbon atom to which they are attached to form C$_{3-8}$ cycloalkyl ring, C$_{5-8}$ cycloalkenyl ring, or five to seven membered heterocyclyl wherein said cycloalkyl, cycloalkenyl and heterocyclyl groups are optionally substituted with C$_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl and cycloheptyl. In a further embodiment of the invention, $R^3$ and $R^4$ form a cyclohexyl ring.

In an embodiment of the invention, $R^4$ and $R^6$ are defined such that they can be taken together with the nitrogen to which they are attached to form a monocyclic or bicyclic heterocyclyl with 5–7 members in each ring and optionally containing, in addition to the nitrogen, 1 or 2 additional heteroatoms selected from N, O and S, said heterocycle optionally substituted with one or more substituents selected from C$_{1-6}$ alkyl, halo, hydroxyalkyl, hydroxy, keto, O$R^7$, S$R^7$ or N($R^7$)$_2$. In a further example, $R^4$ and $R^6$ are defined such that they can be taken together with the nitrogen to which they are attached to form a 5 or 6 membered heterocyclyl ring system. Examples of the heterocycles that can thus be formed include, but are not limited five or six membered rings containing at least one nitrogen, which is optionally substituted with one or more substituents as described above. A preferred embodiment is when optionally substituted pyrrolidinyl and piperinyl is formed. A more preferred embodiment is when optionally substituted pyrrolidinyl is formed.

In an embodiment of the invention, $R^a$ and $R^b$ are defined such that they can be taken together with the carbon or nitrogen to which they are attached to form a monocyclic or bicyclic carbocycle or heterocycle with 5–7 members in each ring. The heterocycle can optionally contain, in addition to the nitrogen, 1 or 2 additional heteroatoms selected from N, O and S. Said carbocycle and heterocycle can be optionally substituted with one or more substituents selected from $C_{1-6}$ alkyl and halo.

Embodied by the present invention are methods for treating disorders related to abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. A preferred embodiment includes methods for treating osteoporosis and metastatic bone disease. A more preferred embodiment includes methods for treating osteoporosis.

Specific embodiments of the present invention include, but are not limited to:

(4S)-1-(3-bromophenyl)-N-cyanomethyl-4-methyl-prolinamide;
(4S)-N-(cyanomethyl)-4-methyl-1-(4'-piperazin-1-yl-1,1'-biphenyl-3-yl)-L-prolinamide;
(4S)-N-(1-cyanocyclopropyl)-4-methyl-1-(4'-piperazin-1-yl-1,1'-biphenyl-3-yl)-L-prolinamide;
(4S)-1-(1,1'-biphenyl-3-yl)-N-(cyanomethyl)-4-methyl-L-prolinamide;
(4S)-1-(4-chloro-1,1'-biphenyl-3-yl)-N-(cyanomethyl)-4-methyl-L-prolinamide;
(4S)-N-(cyanomethyl)-1-[3-(3,3-dimethylbut-1-ynyl)phenyl]-4-methyl-L-prolinamide;
(4S)-N-(cyanomethyl)-1-[3-(3-hydroxy-3-methylbut-1-ynyl)phenyl]-4-methyl-L-prolinamide;
N-(cyanomethyl)-1-(1-phenyl-1H-tetraazol-5-yl)piperidine-2-carboxamide;
(4S)-1-(5-bromo-2-chlorophenyl)-N-(cyanomethyl)-4-methyl-L-prolinamide;
(4S)-1-(3-bromo-4-chlorophenyl)-N-(cyanomethyl)-4-methyl-L-prolinamide;
(4S)-1-(6-chloro-1,1'-biphenyl-3-yl)-N-(cyanomethyl)-4-methyl-L-prolinamide;
1-(5-bromo-2-chlorophenyl)-N-(cyanomethyl)piperidine-2-carboxamide;
1-(3-bromo-4-chlorophenyl)-N-(cyanomethyl)piperidine-2-carboxamide;
1-(4-chloro-1,1'-biphenyl-3-yl)-N-(cyanomethyl)piperidine-2-carboxamide;
(4S)-1-(2-chlorophenyl)-N-(cyanomethyl)-4-methyl-L-prolinamide;
(4S)-1-(6-chloro-4'-piperazin-1-yl-1,1'-biphenyl-3-yl)-N-(cyanomethyl)-4-methyl-L-prolinamide;
1-(3-bromophenyl)-N-(cyanomethyl)-D-prolinamide;
(4S)-1-(4-chloro-4'-piperazin-1-yl-1,1'-biphenyl-3-yl)-N-(cyanomethyl)-4-methyl-L-prolinamide;
N-(cyanomethyl)-1-(4'-piperazin-1-yl-1,1'-biphenyl-3-yl)-D-prolinamide;
1-(5-bromo-2-chlorophenyl)-N-(cyanomethyl)-D-prolinamide;
1-(3-bromo-4-chlorophenyl)-N-(cyanomethyl)-D-prolinamide;
(4S)-1-[4-chloro-4'-(hydroxymethyl)-1,1'-biphenyl-3-yl]-N-(cyanomethyl)-4-methyl-L-prolinamide;
(4S)-1-(2-chloro-1,1'-biphenyl-3-yl)-N-(cyanomethyl)-4-methyl-L-prolinamide;
(4S)-1-{4-chloro-4'-[(dimethylamino)methyl]-1,1'-biphenyl-3-yl}-N-(cyanomethyl)-4-methyl-L-prolinamide;
1-(4-chloro-1,1'-biphenyl-3-yl)-N-(cyanomethyl)-D-prolinamide;
(4S)-1-[4-chloro-4'-(methylthio)-1,1'-biphenyl-3-yl]-N-(cyanomethyl)-4-methyl-L-prolinamide;
(4S)-1-[4-chloro-4'-(methylsulfonyl)-1,1'-biphenyl-3-yl]-N-(cyanomethyl)-4-methyl-L-prolinamide;
N-(cyanomethyl)-1-(2-phenyl-1,3-thiazol-4-yl)-L-prolinamide;
(4S)-N-(cyanomethyl)-4-methyl-1-(2-phenyl-1,3-thiazol-4-yl)-L-prolinamide;
(4S)-1-(4-chloro-4'-piperazin-1-yl-1,1'-biphenyl-3-yl)-N-(cyanomethyl)-4-hydroxy-L-prolinamide;
(4R)-1-(4-chloro-4'-piperazin-1-yl-1,1'-biphenyl-3-yl)-N-(cyanomethyl)-4-hydroxy-L-prolinamide;
1-(4-chloro-4'-piperazin-1-yl-1,1'-biphenyl-3-yl)-N-(cyanomethyl)-4-oxo-L-prolinamide;
(4S)-1-(4-chloro-4'-piperazin-1-yl-1,1'-biphenyl-3-yl)-N-(cyanomethyl)-4-fluoro-L-prolinamide;
(4R)-1-(4-chloro-4'-piperazin-1-yl-1,1'-biphenyl-3-yl)-N-(cyanomethyl)-4-fluoro-L-prolinamide;
1-(4-chloro-4'-piperazin-1-yl-1,1'-biphenyl-3-yl)-N-(cyanomethyl)-4,4-difluoro-L-prolinamide;
(4S)-1-(4-chloro-4'-piperazin-1-yl-1,1'-biphenyl-3-yl)-N-(cyanomethyl)-4-methoxy-L-prolinamide;
(4R)-1-(4-chloro-4'-piperazin-1-yl-1,1'-biphenyl-3-yl)-N-(cyanomethyl)-4-methoxy-L-prolinamide;
(4S)-1-(4-chloro-4'-piperazin-1-yl-1,1'-biphenyl-3-yl)-N-(cyanomethyl)-4-(methylthio)-L-prolinamide;
(4R)-1-(4-chloro-4'-piperazin-1-yl-1,1'-biphenyl-3-yl)-N-(cyanomethyl)-4-(methylthio)-L-prolinamide;
(1R,2S,5S)-3-(4-chloro-4'-piperazin-1-yl-1,1'-biphenyl-3-yl)-N-(cyanomethyl)-3-azabicyclo[3.1.0]hexane-2-carboxamide;
(1S,2S,5R)-3-(4-chloro-4'-piperazin-1-yl-1,1'-biphenyl-3-yl)-N-(cyanomethyl)-3-azabicyclo[3.1.0]hexane-2-carboxamide;
N-(cyanomethyl)-1-[2-(4-piperazin-1-ylphenyl)cyclopropyl]-L-prolinamide;
(4S)-N-(cyanomethyl)-4-methyl-1-[2-(4-piperazin-1-ylphenyl)cyclopropyl]-L-prolinamide;
N-(cyanomethyl)-4,4-difluoro-1-[2-(4-piperazin-1-ylphenyl)cyclopropyl]-L-prolinamide;
(4S)-1-(1,3-benzothiazol-2-yl)-N-(cyanomethyl)-4-methyl-L-prolinamide;
(4S)-N-(cyanomethyl)-4-methyl-1-(1-methyl-5-piperazin-1-yl-1H-benzimidazol-2-yl)-L-prolinamide;
(4S)-1-(4-bromo-1-methyl-1H-benzimidazol-2-yl)-N-(cyanomethyl)-4-methyl-L-prolinamide;
(4S)-N-(cyanomethyl)-4-methyl-1-(1-naphthyl)-L-prolinamide;
(4S)-N-(cyanomethyl)-4-methyl-1-(2-naphthyl)-L-prolinamide;
(4S)-N-(cyanomethyl)-4-methyl-1-(5,6,7,8-tetrahydronaphthalen-2-yl)-L-prolinamide;
(4S)-N-(cyanomethyl)-4-methyl-1-(5,6,7,8-tetrahydronaphthalen-1-yl)-L-prolinamide;
(4S)-N-(cyanomethyl)-4-methyl-1-[5-methyl-2-(4-piperazin-1-ylphenyl)-1,3-thiazol-4-yl]-L-prolinamide;
N-(cyanomethyl)-1-[5-methyl-2-(4-piperazin-1-ylphenyl)-1,3-thiazol-4-yl]-L-prolinamide;
(4S)-N-(cyanomethyl)-4-methyl-1-[5-methyl-2-(3-piperazin-1-ylphenyl)-1,3-thiazol-4-yl]-L-prolinamide;
(4S)-N-(cyanomethyl)-4-methyl-1-(5-methyl-2,2'-bi-1,3-thiazol-4-yl)-L-prolinamide;
(3S)-N-(cyanomethyl)-2-[5-methyl-2-(4-piperazin-1-ylphenyl)-1,3-thiazol-4-yl]-2-azabicyclo[2.2.1]heptane-3-carboxamide;

(4S)-1-{4-chloro-4'-[(methylamino)carbonyl]-1,1'-biphenyl-3-yl}-N-(cyanomethyl)-4-methyl-L-prolinamide;
(4S)-1-(4-chloro-4'-{[(2-methoxyethyl)(methyl)amino]methyl}-1,1'-biphenyl-3-yl)-N-(cyanomethyl)-4-methyl-L-prolinamide;
(4S)-1-(4-chloro4'-propionyl-1,1'-biphenyl-3-yl)-N-(cyanomethyl)-4-methyl-L-prolinamide;
(4S)-1-{4-chloro-4'-[(methylsulfonyl)amino]-1,1'-biphenyl-3-yl}-N-(cyanomethyl)-4-methyl-L-prolinamide;
(4S)-1-[4-chloro-4'-(2-pyrrolidin-1-ylethyl)-1,1'-biphenyl-3-yl]-N-(cyanomethyl)-4-methyl-L-prolinamide;
(4S)-1-{4-chloro-4'-[(methylamino)sulfonyl]-1,1'-biphenyl-3-yl}-N-(cyanomethyl)-4-methyl-L-prolinamide;
(4S)-1-{4-chloro-4'-[(1-methyl-1H-315-imidazol-3-yl)methyl]-1,1'-biphenyl-3-yl}-N-(cyanomethyl)-4-methyl-L-prolinamide;
(4S)-1-[4-chloro-4'-(N,N-dimethylglycyl)-1,1'-biphenyl-3-yl]-N-(cyanomethyl)-4-methyl-L-prolinamide;
(4S)-1-[4-chloro-4'-(5-methyl-1,1-dioxido-1,2,5-thiadiazinan-2-yl)-1,1'-biphenyl-3-yl]-N-(cyanomethyl)-4-methyl-L-prolinamide;
(4S)-1-{4'-[1-(2-amino-2-oxoethyl)-4-hydroxypiperidin-4-yl]-4-chloro-1,1'biphenyl-3-yl}-N-(cyanomethyl)-4-methyl-L-prolinamide;
(4S)-1-(4-chloro-4'-{[(1-methyl-1H-imidazol-2-yl)thio]methyl}-1,1'-biphenyl-3-yl)-N-(cyanomethyl)-4-methyl-L-prolinamide;
(4S)-1-{4-chloro-4'-[1-(2-hydroxyethyl)piperidin-4-yl]-1,1'-biphenyl-3-yl}-N-(cyanomethyl)-4-methyl-L-prolinamide;
(4S)-1-{2-chloro-5-[(1E,3E)-4-({2-[(2-fluoroethyl)amino]ethyl}amino)-1-methylhexa-1,3,5-trienyl]phenyl}-N-(cyanomethyl)-4-methyl-L-prolinamide;
(4S)-1-[4-chloro-4'-(2-oxoimidazolidin-1-yl)-1,1'-biphenyl-3-yl]-N-(cyanomethyl)-4-methyl-L-prolinamide;
(4S)-1-(4-chloro-4'-{1-[(methoxycarbonyl)amino]cyclopropyl}-1,1'-biphenyl-3-yl)-N-(cyanomethyl)-4-methyl-L-prolinamide;
(4S)-N-(cyanomethyl)-4-methyl-1-[4-(4-piperazin-1-ylphenyl)-1,3-thiazol-2-yl]-L-prolinamide;
(4S)-N-(cyanomethyl)-4-methyl-1-[5-(4-piperazin-1-ylphenyl)-1,3-thiazol-2-yl]-L-prolinamide;
(4S)-N-(cyanomethyl)-4-methyl-1-[5-(4-piperazin-1-ylphenyl)isothiazol-3-yl]-L-prolinamide;
(4S)-N-(cyanomethyl)-4-methyl-1-[1-(4-piperazin-1-ylphenyl)-1H-pyrazol-3-yl]-L-prolinamide;
(4S)-N-(cyanomethyl)-4-methyl-1-[1-(4-piperazin-1-ylphenyl)-1H-pyrazol-4-yl]-L-prolinamide;
(4S)-N-(cyanomethyl)-4-methyl-1-[1-methyl-3-(4-piperazin-1-ylphenyl)-1H-pyrazol-5-yl]-L-prolinamide;
(4S)-N-(cyanomethyl)-4-methyl-1-[5-(4-piperazin-1-ylphenyl)-1,2,4-thiadiazol-3-yl]-L-prolinamide;
(4S)-N-(cyanomethyl)-4-methyl-1-[5-(4-piperazin-1-ylphenyl)-1,3,4-thiadiazol-2-yl]-L-prolinamide;
(4S)-N-(cyanomethyl)-4-methyl-1-[3-(4-piperazin-1-ylphenyl)-1,2,4-thiadiazol-5-yl]-L-prolinamide;
(4S)-N-(cyanomethyl)-4-methyl-1-[1-(4-piperazin-1-ylphenyl)-1H-1,2,4-triazol-3-yl]-L-prolinamide;
(4S)-N-(cyanomethyl)-4-methyl-1-[1-methyl-3-(4-piperazin-1-ylphenyl)-1H-1,2,4-triazol-5-yl]-L-prolinamide;
1-(3-bromophenyl)-N-(cyanomethyl)-2-piperidinecarboxamide;
N-(cyanomethyl)-1-[4'-(1-piperazinyl)[1,1'-biphenyl]-3-yl]-2-piperidinecarboxamide;
(2R,3S)-1-(3-bromophenyl)-N-(cyanomethyl)-3-methyl-2-piperidinecarboxamide;
1-[1,1'-biphenyl]-3-yl-N-(cyanomethyl)-2-piperidinecarboxamide;
N-(cyanomethyl)-1-[3-(2-naphthyl)phenyl]-2-piperidinecarboxamide;
N1-(cyanomethyl)-N2-{4-[4-(4-methylpiperazin-1-yl)phenyl]thien-3-yl}-L-leucinamide;
N1-(cyanomethyl)-N2-[4-(4-piperazin-1-ylphenyl)isothiazol-3-yl]-L-leucinamide;
N1-(cyanomethyl)-N2-(4-{4-[(dimethylamino)methyl]phenyl}thien-3-yl)-L-leucinamide;
N1(cyanomethyl)-N2-[4-(4-{[(2-hydroxyethyl)amino]methyl}phenyl)thien-3-yl]-L-leucinamide;
N1-(cyanomethyl)-N2-{4-[4-(morpholin-4-ylmethyl)phenyl]thien-3-yl}-L-leucinamide;
N2-(4-{[(benzylamino)methyl]phenyl}thien-3-yl)-N1-(cyanomethyl)-L-leucinamide;
N2-[4-(4-tert-butylphenyl)thien-3-yl]-N1-(cyanomethyl)-L-leucinamide;
N1-(cyanomethyl)-N2-[4-(4-isopropylphenyl)thien-3-yl]-L-leucinamide;
N1-(cyanomethyl)-N2-[3-(4-piperazin-1-ylphenyl)isoxazol-4-yl]leucinamide;
N1-(cyanomethyl)-N2-[3-(4-piperazin-1-ylphenyl)isoxazol-4-yl]-L-leucinamide;
N1-(cyanomethyl)-N2-[3-(4-piperazin-1-ylphenyl)isoxazol-4-yl]-D-leucinamide;
N1-(cyanomethyl)-N2-(4-{4-[2-(dimethylamino)ethyl]phenyl}thien-3-yl)-L-leucinamide;
N1-(1-cyanocyclopropyl)-N2-[3-(4-piperazin-1-ylphenyl)isoxazol-4-yl]-L-leucinamide;
N1-(cyanomethyl)-N2-{3-[4-(4-isopropylpiperazin-1-yl)phenyl]isoxazol-4-yl}-L-leucinamide;
N2-[4-(3-bromo-4-piperazin-1-ylphenyl)-3-methylisothiazol-5-yl]-N1-(cyanomethyl)leucinamide;
N1-(cyanomethyl)-N2-{4-[4-(4-isopropylpiperazin-1-yl)phenyl]isothiazol-3-yl}-L-leucinamide;
N2-[4-(3-bromo-4-piperazin-1-ylphenyl)isothiazol-3-yl]-N1-(cyanomethyl)-L-leucinamide;
N2-[4-(4-bromophenyl)isothiazol-3-yl]-N1-(cyanomethyl)-L-leucinamide;
N1-(cyanomethyl)-N2-(1-phenyl-1H-tetraazol-5-yl)-L-leucinamide;
N1-(cyanomethyl)-N2-(1-phenyl-1H-tetraazol-5-yl)-L-leucinamide;
N1-(cyanomethyl)-N2-[4-(4-iodophenyl)-3-methylisothiazol-5-yl]-L-leucinamide;
N1-(cyanomethyl)-N2-(3-methyl-4-phenylisothiazol-5-yl)-L-leucinamide;
N2-[4-(1,1'-biphenyl-4-yl)-3-methylisothiazol-5-yl]-N1-(cyanomethyl)-L-leucinamide;
N1-(cyanomethyl)-N2-[4-(4-piperazin-1-ylphenyl)isothiazol-5-yl]leucinamide;
N1-(cyanomethyl)-N2-[3-methyl-4-(4-pyridin-3-ylphenyl)isothiazol-5-yl]-L-leucinamide;
N1-(cyanomethyl)-N2-[3-methyl-4-(4-pyridin-4-ylphenyl)isothiazol-5-yl]-L-leucinamide;
N1-(cyanomethyl)-N2-{3-methyl-4-[4-(1-trityl-1H-imidazol-5-yl)phenyl]isothiazol-5-yl}-L-leucinamide;
N1-(cyanomethyl)-N2-{4-[4-(1H-imidazol-5-yl)phenyl]-3-methylisothiazol-5-yl}-L-leucinamide;
N1-(cyanomethyl)-N2-{3-methyl-4-[4-(1-trityl-1H-imidazol-2-yl)phenyl]isothiazol-5-yl}-L-leucinamide;
N1-(cyanomethyl)-N2-[4-(4-hydroxyphenyl)-3-methyl-isothiazol-5-yl]-L-leucinamide;
N1-(cyanomethyl)-N2-{3-methyl-4-[4-(1-oxidopylidin-4-yl)phenyl]isothiazol-5-yl}-L-leucinamide;

N1-(cyanomethyl)-N2-[4-(2-piperazin-1-ylpyrimidin-5-yl) isothiazol-3-yl]-L-leucinamide;
N1-(cyanomethyl)-N2-{4-[4-piperazin-1-yl-2-(trifluoromethyl)phenyl]isothiazol-3-yl}-L-leucinamide;
N1-(cyanomethyl)-N2-{4-[4-(1,4-diazepan-1-yl)phenyl] isothiazol-3-yl}-L-leucinamide;
N1-(cyanomethyl)-N2-{4-[4-(3,5-dimethylpiperazin-1-yl) phenyl]isothiazol-3-yl}-L-leucinamide;
N1-(cyanomethyl)-N2-{4-[4-(N,N-dimethylglycyl)phenyl] isothiazol-3-yl}-L-leucinamide;
N1-(cyanomethyl)-N2-(4-{4-[(2,6-dimethylpiperidin-1-yl) acetyl]phenyl}isothiazol-3-yl)-L-leucinamide;
N1-(cyanomethyl)-N2-{4-[4-(N,N-dimethylglycyl)phenyl]-3-methylisothiazol-5-yl}-L-leucinamide;
N2-{4-[4-(1-amino-1-methylethyl)phenyl]isothiazol-3-yl}-N1-(cyanomethyl)-L-leucinamide;
N2-[4-(4-acetylphenyl)-3-methylisothiazol-5-yl]-N1-(cyanomethyl)-L-leucinamide;
N2-(4-{4-[(tert-butylamino)sulfonyl]phenyl}-3-methylisothiazol-5-yl)-N1-(cyanomethyl)-L-leucinamide;
N1-(cyanomethyl)-N2-{3-methyl-4-[4-(piperazin-1-ylsulfonyl)phenyl]isothiazol-5-yl}-L-leucinamide;
N1-(cyanomethyl)-N2-{3-methyl-4-[4-(methylsulfonyl) phenyl]isothiazol-5-yl}-L-leucinamide;
N2-{4-[4-(aminosulfonyl)phenyl]-3-methylisothiazol-5-yl}-N1-(cyanomethyl)-L-leucinamide;
N1-(cyanomethyl)-N2-[4-(2-fluoro-4-piperazin-1-ylphenyl)-3-methylisothiazol-5-yl]-L-leucinamide;
N1-(cyanomethyl)-N2-[4-(3-fluoro-4-piperazin-1-ylphenyl) thien-3-yl]-L-leucinamide;
N1-(cyanomethyl)-N2-{4-[3-(hydroxymethyl)phenyl]thien-3-yl}-L-leucinamide;
N2-(2-bromo-4-{3-[(dimethylamino)methyl]phenyl}thien-3-yl)-N1-(cyanomethyl)-L-leucinamide;
N1-(cyanomethyl)-N2-(4-{3-[(dimethylamino)methyl] phenyl}thien-3-yl)-L-leucinamide;
N1-(cyanomethyl)-N2-{4-[3-fluoro-4-(hydroxymethyl)phenyl]thien-3-yl}-L-leucinamide;
N1-(cyanomethyl)-N2-{4-[4-(4-hydroxypiperidin-4-yl)phenyl]thien-3-yl}-L-leucinamide;
N1-(cyanomethyl)-N2-(4-{4-[(dimethylamino)methyl]-3-fluorophenyl}thien-3-yl)-L-leucinamide;
4-(4-{4-[1-(Cyanomethyl-carbamoyl)-3-methyl-butylamino]-thiophen-3-yl}-2-fluoro-benzyl)-piperazine-1-carboxylic acid tert-butyl ester;
N1-(cyanomethyl)-N2-{4-[3-fluoro-4-(piperazin-1-ylmethyl)phenyl]thien-3-yl}-L-leucinamide;
N1-(cyanomethyl)-N2-{4-[4-(pyrrolidin-1-ylmethyl)phenyl]thien-3-yl}-L-leucinamide;
N1-(cyanomethyl)-N2-[3-methyl-4-(4-piperazin-1-ylphenyl)isothiazol-5-yl]-L-leucinamide;
N1-(cyanomethyl)-N2-{4-[4-(4-isopropylpiperazin-1-yl) phenyl]-3-methylisothiazol-5-yl}-L-leucinamide;
6-{5-[1-(Cyanomethyl-carbamoyl)-3-methyl-butylamino]-3-methyl-isothiazol4-yl}-napthalene-2-carboxylic acid methyl ester;
N1-(cyanomethyl)-N2-(3-methyl-4-{4-[4-(2,2,2-trifluoroethyl)piperazin-1-yl]phenyl}isothiazol-5-yl)-L-leucinamide;
N1-(cyanomethyl)-N2-{3-methyl-4-[4-(4-propylpiperazin-1-yl)phenyl]isothiazol-5-yl}-L-leucinamide;
N2-{4-[4-(4-acetylpiperazin-1-yl)phenyl]-3-methylisothiazol-5-yl}-N1-(cyanomethyl)-L-leucinamide;
N1-(cyanomethyl)-N2-(3-methyl-4-{4-[4-(methylsulfonyl) piperazin-1-yl]phenyl}isothiazol-5-yl)-L-leucinamide;
N2-{4-[4-(4-tert-butylpiperazin-1-yl)phenyl]-3-methylisothiazol-5-yl}-N1-(cyanomethyl)-L-leucinamide;
N1-(cyanomethyl)-N2-(4-{4-[(1S,4S)-2,5-diazabicyclo [2.2.1]hept-2-yl]phenyl}-3-methylisothiazol-5-yl)-L-leucinamide;
N1-(cyanomethyl)-N2-{4-[6-(hydroxymethyl)-2-naphthyl]-3-methylisothiazol-5-yl}-L-leucinamide;
N1-(cyanomethyl)-N2-(4-{4-[4-(2-hydroxyethyl)piperazin-1-yl]phenyl}-3-methylisothiazol-5-yl)-L-leucinamide;
N1-(cyanomethyl)-N2-{4-[4-(4-cyclopropylpiperazin-1-yl) phenyl]-3-methylisothiazol-5-yl}-L-leucinamide;
N1-(cyanomethyl)-N2-(4-{4-[4-(2-methoxyethyl)piperazin-1-yl]phenyl}-3-methylisothiazol-5-yl)-L-leucinamide;
N1-(cyanomethyl)-N2-(4-{4-[4-(2-fluoroethyl)piperazin-1-yl]phenyl}-3-methylisothiazol-5-yl)-L-leucinamide;
N1-(cyanomethyl)-N2-(4-{6-[(dimethylamino)methyl]-2-naphthyl}-3-methylisothiazol-5-yl)-L-leucinamide;
N1-(cyanomethyl)-N2-{3-methyl-4-[6-(pyrrolidin-1-ylmethyl)-2-naphthyl]isothiazol-5-yl}-L-leucinamide;
N1-(cyanomethyl)-N2-(4-{4-[4-(2-hydroxypropyl)piperazin-1-yl]phenyl}-3-methylisothiazol-5-yl)-L-leucinamide;
N1-(cyanomethyl)-N2-(4-{4-[4-(2-hydroxy-2-methylpropyl)piperazin-1-yl]phenyl}-3-methylisothiazol-5-yl)-L-leucinamide;
N2-(4-{4-[4-(2-anilino-2-oxoethyl)piperazin-1-yl]phenyl}-3-methylisothiazol-5-N1-(cyanomethyl)-L-leucinamide;
N2-(4-{4-[4-(2-amino-2-oxoethyl)piperazin-1-yl]phenyl}-3-methylisothiazol-5-yl)-N1-(cyanomethyl)-L-leucinamide;
N1-(cyanomethyl)-N2-{3-methyl-4-[4-(4-methylmorpholin-2-yl)phenyl]isothiazol-5-yl}-L-leucinamide;
N1-(cyanomethyl)-N2-[3-methyl-4-(4-morpholin-4-ylphenyl)isothiazol-5-yl]-L-leucinamide;
N1-(cyanomethyl)-N2-(4-phenylthien-3-yl)-L-leucinamide;
N1-(1-cyanocyclopropyl)-N2-[4-(4-piperazin-1-ylphenyl) thien-3-yl]-L-leucinamide;
N1-(cyanomethyl)-N2-[1-methyl-4-(4-piperazin-1-ylphenyl)-1H-pyrazol-3-yl]leucinamide;
N1-(cyanomethyl)-N2-[3-methyl-4-(4-piperazin-1-ylphenyl)isothiazol-5-yl]leucinamide;
N1-(cyanomethyl)-N2-[4-(4-piperazin-1-ylphenyl)-1,2,5-oxadiazol-3-yl]leucinamide;
N1-(cyanomethyl)-N2-[4-(4-piperazin-1-ylphenyl)-1H-pyrazol-3-yl]leucinamide;
N1-(cyanomethyl)-N2-[3-methyl-4-(4-piperazin-1-ylphenyl)isoxazol-5-yl]leucinamide;
N1-(cyanomethyl)-N2-[5-methyl-4-(4-piperazin-1-ylphenyl)isoxazol-3-yl]leucinamide;
N1-(cyanomethyl)-N2-(4-{4-[(methylamino)methyl] phenyl}thien-3-yl)-L-leucinamide;
N2-(4-{4-[(tert-butylamino)methyl]phenyl}thien-3-yl)-N1-(cyanomethyl)-L-leucinamide;
N1-(cyanomethyl)-N2-[4-(4-{[(2,2,2-trifluoroethyl)amino] methyl}phenyl)thien-3-yl]-L-leucinamide;
N1-(cyanomethyl)-N2-(4-{4-[1-(methylamino)ethyl] phenyl}thien-3-yl)-L-leucinamide;
N1-(cyanomethyl)-N2-(4-{4-[(isopropylamino)methyl] phenyl}thien-3-yl)-L-leucinamide;
N1-(cyanomethyl)-N2-[4-(4-{[(cyclopropylmethyl)amino] methyl}phenyl)thien-3-yl]-L-leucinamide;
N1-(cyanomethyl)-N2-(4-{4-[1-(isopropylamino)ethyl] phenyl}thien-3-yl)-L-leucinamide;
N1-(cyanomethyl)-N2-[4-(4-{[(2S)-2-(hydroxymethyl)pyrrolidin-1-yl]methyl}phenyl)thien-3-yl]-L-leucinamide;
N1-(cyanomethyl)-N2-[4-(4-{[(3-pyrrolidin-1-ylpropyl) amino]methyl}phenyl)thien-3-yl]-L-leucinamide;
N1-(cyanomethyl)-N2-{4-[4-(1H-imidazol-1-ylmethyl)phenyl]thien-3-yl}-L-leucinamide;

N1-(cyanomethyl)-N2-{4-[6-(4-methylpiperazin-1-yl)pyridin-3-yl]thien-3-yl}-L-leucinamide;
N1-(cyanomethyl)-N2-[4-(6-piperazin-1-ylpyridin-3-yl)thien-3-yl]-L-leucinamide;
N1-(cyanomethyl)-N2-{4-[4-(trifluoromethyl)phenyl]thien-3-yl}-L-leucinamide;
N2-[4-(3-bromophenyl)thien-3-yl]-N1-(cyanomethyl)-L-leucinamide;
N1-(cyanomethyl)-N2-[4-(1-naphthyl)thien-3-yl]-L-leucinamide;
N2-(5-acetyl-2,3'-bithien-4'-yl)-N1-(cyanomethyl)-L-leucinamide;
N1-(cyanomethyl)-N2-(5-methyl-2,3'-bithien-4'-yl)-L-leucinamide;
N2-[4-(4-chlorophenyl)thien-3-yl]-N1-(cyanomethyl)-L-leucinamide;
N1-(cyanomethyl)-N2-[4-(4-fluorophenyl)thien-3-yl]-L-leucinamide;
N1-(cyanomethyl)-N2-[4-(2-methylphenyl)thien-3-yl]-L-leucinamide;
N1-(cyanomethyl)-N2-[4-(4-vinylphenyl)thien-3-yl]-L-leucinamide;
N1-(cyanomethyl)-N2-[4-(3-ethoxyphenyl)thien-3-yl]-L-leucinamide;
N1-(cyanomethyl)-N2-[4-(1H-indol-5-yl)thien-3-yl]-L-leucinamide;
N1-(cyanomethyl)-N2-[4-(3-fluoro-2-methylphenyl)thien-3-yl]-L-leucinamide;
N1-(cyanomethyl)-N2-[4-(1H-pyrrol-2-yl)thien-3-yl]-L-leucinamide;
N1-(cyanomethyl)-N2-[4-(4-methylphenyl)thien-3-yl]-L-leucinamide;
N1-(cyanomethyl)-N2-(4-pyridin-3-ylthien-3-yl)-L-leucinamide;
N1-(cyanomethyl)-N2-[4-(4-methoxyphenyl)thien-3-yl]-L-leucinamide;
N1-(cyanomethyl)-N2-[4-(5-fluoro-2-methylphenyl)thien-3-yl]-L-leucinamide;
N2-(3,3'-bithien-4-yl)-N1-(cyanomethyl)-L-leucinamide;
N1-(cyanomethyl)-N2-[4-(3,5-dichlorophenyl)thien-3-yl]-L-leucinamide;
N2-{4-[3-(acetylamino)phenyl]thien-3-yl}-N1-(cyanomethyl)-L-leucinamide;
N2-[4-(4-bromophenyl)thien-3-yl]-N1-(cyanomethyl)-L-leucinamide;
N1-(cyanomethyl)-N2-{4-[4-fluoro-3-(trifluoromethyl)phenyl]thien-3-yl}-L-leucinamide;
N2-[4-(1-benzofuran-2-yl)thien-3-yl]-N1-(cyanomethyl)-L-leucinamide;
N1-(cyanomethyl)-N2-[4-(2-formylphenyl)thien-3-yl]-L-leucinamide;
N2-[4-(3-chlorophenyl)thien-3-yl]-N1-(cyanomethyl)-L-leucinamide;
N1-(cyanomethyl)-N2-[4-(2,4-dichlorophenyl)thien-3-yl]-L-leucinamide;
N1-(cyanomethyl)-N2-{4-[4-(trifluoromethyl)phenyl]thien-3-yl}-L-leucinamide;
N1-(cyanomethyl)-N2-{4-[3-(trifluoromethyl)phenyl]thien-3-yl}-L-leucinamide;
N1-(cyanomethyl)-N2-[4-(3-fluorophenyl)thien-3-yl]-L-leucinamide;
N1-(cyanomethyl)-N2-[4-(2-methoxyphenyl)thien-3-yl]-L-leucinamide;
N2-{4-[3,5-bis(trifluoromethyl)phenyl]thien-3-yl}-N1-(cyanomethyl)-L-leucinamide;
N2-[4-(3-chloro-4-fluorophenyl)thien-3-yl]-N1-(cyanomethyl)-L-leucinamide;
N1-(cyanomethyl)-N2-{4-[2-(trifluoromethyl)phenyl]thien-3-yl}-L-leucinamide;
N1-(cyanomethyl)-N2-{4-[4-(methylthio)phenyl]thien-3-yl}-L-leucinamide;
N1-(cyanomethyl)-N2-[4-(3-fluoro-4-methoxyphenyl)thien-3-yl]-L-leucinamide;
N1-(cyanomethyl)-N2-[4-(3,4-dichlorophenyl)thien-3-yl]-L-leucinamide;
N2-[4-(1,3-benzodioxol-5-yl)thien-3-yl]-N1-(cyanomethyl)-L-leucinamide;
N1-(cyanomethyl)-N2-[4-(3,4-dimethoxyphenyl)thien-3-yl]-L-leucinamide;
N1-(cyanomethyl)-N2-[4-(3,4,5-trimethoxyphenyl)thien-3-yl]-L-leucinamide;
N1-(cyanomethyl)-N2-[4-(3-formyl-2-furyl)thien-3-yl]-L-leucinamide;
N1-(cyanomethyl)-N2-[4-(3-isopropoxyphenyl)thien-3-yl]-L-leucinamide;
N1-(cyanomethyl)-N2-[4-(2,3-dimethoxyphenyl)thien-3-yl]-L-leucinamide;
N1-(cyanomethyl)-N2-{4-[4-(trifluoromethoxy)phenyl]thien-3-yl}-L-leucinamide;
N1-(cyanomethyl)-N2-{4-[4-(hydroxymethyl)phenyl]thien-3-yl}-L-leucinamide;
N2-[4-(1,1'-biphenyl-3-yl)thien-3-yl]-N1-(cyanomethyl)-L-leucinamide;
N1-(cyanomethyl)-N2-[4-(3-cyanophenyl)thien-3-yl]-L-leucinamide;
N1-(cyanomethyl)-N2-[4-(1H-indol-5-yl)thien-3-yl]-L-leucinamide;
N2-[4-(5-chloro-2-methoxyphenyl)thien-3-yl]-N1-(cyanomethyl)-L-leucinamide;
N1-(cyanomethyl)-N2-[4-(2,5-dimethoxyphenyl)thien-3-yl]-L-leucinamide;
N2-[4-(4-chloro-3-fluorophenyl)thien-3-yl]-N1-(cyanomethyl)-L-leucinamide;
N1-(cyanomethyl)-N2-[4-(3,5-dimethylisoxazol-4-yl)thien-3-yl]-L-leucinamide;
N2-[4-(4-acetylphenyl)thien-3-yl]-N1-(cyanomethyl)-L-leucinamide;
N1-(cyanomethyl)-N2-[4-(4-methylphenyl)thien-3-yl]-L-leucinamide;
N1-(cyanomethyl)-N2-(4-pyrimidin-5-ylthien-3-yl)-L-leucinamide
N1-(cyanomethyl)-N2-[4-(3-nitrophenyl)thien-3-yl]-L-leucinamide;
N1-(cyanomethyl)-N2-(4-phenylthien-3-yl)-L-leucinamide;
N1-(cyanomethyl)-N2-[4-(3-methoxyphenyl)thien-3-yl]-L-leucinamide;
N1-(cyanomethyl)-N2-{4-[2-(hydroxymethyl)phenyl]thien-3-yl}-L-leucinamide;
N2-[4-(3-aminophenyl)thien-3-yl]-N1-(cyanomethyl)-L-leucinamide;
N1-(cyanomethyl)-N2-(4-pyridin-4-ylthien-3-yl)-L-leucinamide;
N1-(cyanomethyl)-N2-[4-(4-cyanophenyl)thien-3-yl]-L-leucinamide;
N2-[4-(1-benzothien-3-yl)thien-3-yl]-N1-(cyanomethyl)-L-leucinamide;
N1-(cyanomethyl)-N2-(4-quinolin-5-ylthien-3-yl)-L-leucinamide;
N1-(cyanomethyl)-N2-(4-quinolin-8-ylthien-3-yl)-L-leucinamide;
N1-(cyanomethyl)-N2-[4-(1H-pyrazol-3-yl)thien-3-yl]-L-leucinamide;
N1-(cyanomethyl)-N2-[4-(5-fluoro-2-methoxyphenyl)thien-3-yl]-L-leucinamide;

N2-[4-(1-benzothien-7-yl)thien-3-yl]-N1-(cyanomethyl)-L-leucinamide;
N1-(cyanomethyl)-N2-(4-quinolin-6-ylthien-3-yl)-L-leucinamide;
N1-(cyanomethyl)-N2-[4-(3-oxo-3-phenylpropanoyl)thien-3-yl]-L-leucinamide;
N1-(cyanomethyl)-N2-[4-(3-phenylisoxazol-5-yl)thien-3-yl]-L-leucinamide;
N1-(cyanomethyl)-N2-[4-(2-naphthyl)thien-3-yl]-L-leucinamide;
N-(cyanomethyl)-2-[(5,5-dimethyl-2-oxo-4-phenyl-2,5-dihydro-3-furanyl)amino]-4-methylpentanamide;
(2S)-N-(cyanomethyl)-4-methyl-2-({4-[4-(1-piperazinyl)phenyl]-3-thienyl}amino)pentanamide;
2-{[4'-(aminomethyl)-1,1'-biphenyl4-yl]thio}-N-(cyanomethyl)-4-methylpentanamide;
2-(1,1'-biphenylylthio)-N-(cyanomethyl)-4-methylpentanamide;
N-(cyanomethyl)-2-{[4'-(hydroxymethyl)-1,1'-biphenyl-4-yl]thio}-4-methylpentanamide;
N-(cyanomethyl)-4-methyl-2-[(4'-piperidin-1-yl-1,1'-biphenyl-4-yl)thio]pentanamide;
2-({4'-[(benzylamino)methyl]-1,1'-biphenyl-4-yl}thio)-N-(cyanomethyl)-4-methylpentanamide;
N-(cyanomethyl)-2-({4'-[(cyclopropylamino)methyl]-1,1'-biphenyl-4-yl}thio)-4-methylpentanamide;
N-(cyanomethyl)-4-methyl-2-[(4'-{[(1-methylpiperidin-4-yl)amino]methyl}-1,1'-biphenyl-4-yl)thio]pentanamide;
N-(cyanomethyl)-2-({4'-[(dicyclobutylamino)methyl]-1,1'-biphenyl-4-yl}thio)-4-methylpentanamide;
N-(cyanomethyl)-2-({4'-[(dicyclopentylamino)methyl]-1,1'-biphenyl-4-yl}thio)-4-methylpentanamide;
N-(cyanomethyl)-2-({4'-[(cyclopentylamino)methyl]-1,1'-biphenyl-4-yl}thio)-4-methylpentanamide;
N-(cyanomethyl)-4-methyl-2-[(4-piperazin-1-ylphenyl)thio]pentanamide;
N-(cyanomethyl)-2-[(3',5'-difluoro-1,1'-biphenyl-4-yl)thio]-4-methylpentanamide;
2-{[4-(5-chlorothien-2-yl)phenyl]thio}-N-(cyanomethyl)-4-methylpentanamide;
N-(cyanomethyl)-4-methyl-2-{[4'-(trifluoromethyl)-1,1'-biphenyl-4-yl]thio}pentanamide;
N-(cyanomethyl)-4-methyl-2-[(3'-methyl-1,1'-biphenyl-4-yl)thio]pentanamide;
N-(cyanomethyl)-4-methyl-2-[(4-quinolin-5-ylphenyl)thio]pentanamide;
2-{[4-(1-benzothien-3-yl)phenyl]thio}-N-(cyanomethyl)-4-methylpentanamide;
N-(cyanomethyl)-4-methyl-2-[(4-quinolin-8-ylphenyl)thio]pentanamide;
2-[(4'-cyano-1,1'-biphenyl-4-yl)thio]-N-(cyanomethyl)-4-methylpentanamide;
N-(cyanomethyl)-4-methyl-2-{[4-(1H-pyrazol-3-yl)phenyl]thio}pentanamide;
N-(cyanomethyl)-2-[(5'-fluoro-2'-methoxy-1,1'-biphenyl-4-yl)thio]-4-methylpentanamide;
2-{[4-(1-benzothien-7-yl)phenyl]thio}-N-(cyanomethyl)-4-methylpentanamide;
N-(cyanomethyl)-4-methyl-2-[(4-quinolin-6-ylphenyl)thio]pentanamide;
N-(cyanomethyl)-2-[(3'-fluoro-4'-piperazin-1-yl-1,1'-biphenyl-4-yl)thio]-4-methylpentanamide;
N-(cyanomethyl)-2-{[4'-(4-ethylpiperazin-1-yl)-1,1'-biphenyl4-yl]thio)}-4-methylpentanamide;
N-(cyanomethyl)-2-[(3'-ethyl-4'-piperazin-1-yl-1,1'-biphenyl-4-yl)thio]-4-methylpentanamide;
N-(cyanomethyl)-4-methyl-2-[(4-{2-[(4-propylpiperazin-1-yl)carbonyl]-1H-indol-5-yl}phenyl)thio]pentanamide;
N-(cyanomethyl)-4-methyl-2-[(4-{2-[(4-methylpiperazin-1-yl)carbonyl]-1H-indol-5-yl}phenyl)thio]pentanamide;
N-(cyanomethyl)-4-methyl-2-({4-[2-(piperazin-1-ylcarbonyl)-1H-indol-5-yl]phenyl}thio)pentanamide;
N-(cyanomethyl)-2-{[4'-(4-methoxypiperidin-4-yl)-1,1'-biphenyl-4-yl]thio}-4-methylpentanamide;
N-(cyanomethyl)-4-methyl-2-{[4-(2-piperazin-1-ylpyrinidin-5-yl)phenyl]thio}pentanamide;
N-(cyanomethyl)-4-methyl-2-{[4'-piperazin-1-yl-2'-(trifluoromethyl)-1,1'-biphenyl-4-yl]thio}pentanamide;
N-(cyanomethyl)-1-{[4'-(4-ethylpiperazin-1-yl)-1,1'-biphenyl-4-yl]thio}cyclohexanecarboxamide;
N-(cyanomethyl)-2-{[4'-(2,6-dimethylpiperazin-1-yl)-1,1'-biphenyl-4-yl]thio}-4-methylpentanamide;
N-(cyanomethyl)-2-({4-[5-(2-hydroxyethyl)-4-methyl-1,3-thiazol-2-yl]phenyl}thio)-4-methylpentanamide;
2-[(4'-acetyl-1,1'-biphenyl-4-yl)thio]-N-(cyanomethyl)-4-methylpentanamide;
N-(cyanomethyl)-3-(1-methylcyclopropyl)-2-[(4'-piperazin-1-yl-1,1'-biphenyl-4-yl)thio]propanamide;
N-(cyanomethyl)-2-{[4-(1H-imidazol-4-yl)phenyl]thio}-4-methylpentanamide;
(2R)-N-(cyanomethyl)-4-methyl-2-[(4'-piperazin-1-yl-1,1'-biphenyl-4-yl)thio]pentanamide;
(2S)-N-(cyanomethyl)-4-methyl-2-[(4'-piperazin-1-yl-1,1'-biphenyl-4-yl)thio]pentanamide
N-(cyanomethyl)-1-[(4'-piperazin-1-yl-1,1'-biphenyl-4-yl)thio]cyclohexanecarboxamide;
N-(cyanomethyl)-4-methyl-2-[(4'-{[2-(trimethylsilyl)ethyl]sulfonyl}-1,1'-biphenyl-4-yl)thio]pentanamide;
2-{[4-(4-chlorophenyl)-1,2,3-thiadiazol-5-yl]thio}-N-(cyanomethyl)-4-methylpentanamide;
N-(cyanomethyl)-4-methyl-2-[(3-methyl-1-phenyl-1H-pyrazol-5-yl)thio]pentanamide;
2-[(4-bromo-3-methyl-1-phenyl-1H-pyrazol-5-yl)thio]-N-(cyanomethyl)-4-methylpentanamide;
N-(cyanomethyl)-4-methyl-2-[(5-phenyl-4H-1,2,4-triazol-3-yl)sulfanyl]pentanamide;
N-(cyanomethyl)-4-methyl-2-{[4'-(1-piperazinyl)[1,1'-biphenyl]-3-yl]sulfanyl}pentanamide;
N-(cyanomethyl)-4-methyl-2-{[4'-(1-piperazinyl)[1,1'-biphenyl]-2-yl]sulfanyl}pentanamide;
1-[(2-bromophenyl)sulfanyl]-N-(cyanomethyl)cyclohexanecarboxamide;
N-(cyanomethyl)-4-methyl-2-{[4'-(1-piperazinyl)[1,1'-biphenyl]-4-yl]sulfanyl}pentanamide;
1-[(3-bromophenyl)sulfanyl]-N-(cyanomethyl)cyclohexanecarboxamide;
N-(cyanomethyl)-1-{[4'-(1-piperazinyl)[1,1'-biphenyl]-2-yl]sulfanyl}cyclohexanecarboxamide;
N-(cyanomethyl)-1-{[4'-(1-piperazinyl)[1,1'-biphenyl]-3-yl]sulfanyl}cyclohexanecarboxamide;
N-(cyanomethyl)-4-methyl-2-[(4-piperazin-1-ylbenzyl)thio]pentanamide;
N-(cyanomethyl)-4-methyl-2-{[(4'-piperazin-1-yl-1,1'-biphenyl-4-yl)methyl]thio}pentanamide;
(2S)-N-(cyanomethyl)-4-methyl-2-{[4'-(1-piperazinyl)[1,1'-biphenyl]-4-yl]amino}pentanamide;
(2S)-N-(cyanomethyl)-4-methyl-2-{[4'-(1-piperazinyl)[1,1'-biphenyl]-3-yl]amino}pentanamide;
1-(3-bromoanilino)-N-(cyanomethyl)cyclohexanecarboxamide;
(2S)-N-(cyanomethyl)-4-methyl-2-{[4'-(1-piperazinyl)[1,1'-biphenyl]-2-yl]amino}pentanamide;

(2S)-N-(cyanomethyl)-4-methyl-2-({4'-[2-(4-methyl-1-piperazinyl)-1,3-thiazol-4-yl][1,1'-biphenyl]-3-yl}amino)pentanamide;
(2S)-N-(cyanomethyl)-4-methyl-2-({4'-[2-(4-methyl-1-piperazinyl)-1,3-thiazol-4-yl][1,1'-biphenyl]-2-yl}amino)pentanamide;
N-(cyanomethyl)-4-methyl-2-({3-[4-(1-piperazinyl)phenyl]-2-pyridinyl}oxy)pentanamide;
(2S)-N-(cyanomethyl)-4-methyl-2-({5-[4-(1-piperazinyl)phenyl]-2-pyridinyl}amino)pentanamide;
2-([1,1'-biphenyl]-4-ylmethoxy)-N-(cyanomethyl)-4-methylpentanamide;
N-(cyanomethyl)-4-methyl-2-{[4'-(1-piperazinyl)[1,1'-biphenyl]-4-yl]sulfonyl}pentanamide;
N-(cyanomethyl)-4methyl-2-{[4'-(1-piperazinyl)[1,1'-biphenyl]-3-yl]sulfonyl}pentanamide;
N-(cyanomethyl)-4-methyl-2-{[4'-(1-piperazinyl)[1,1'-biphenyl]-2-yl]sulfonyl}pentanamide;
N-(cyanomethyl)-4-methyl-2-({5-[4-(1-piperazinyl)phenyl]-2-pyrimidinyl}amino)pentanamide;
N-(cyanomethyl)-1-{[4'-(1-piperazinyl)[1,1'-biphenyl]-3-yl]amino}cyclohexanecarboxamide;
triisopropylsilyl 4-[3'-(1-{[(cyanomethyl)amino]carbonyl}-3-methylbutoxy)[1,1'-biphenyl]-4-yl]-1-piperazinecarboxylate;
triisopropylsilyl 4-[4'-(1-{[(cyanomethyl)amino]carbonyl}-3-methylbutoxy)[1,1'-biphenyl]-4-yl]-1-piperazinecarboxylate;
N-(cyanomethyl)-1-{[4'-(1-piperazinyl)[1,1'-biphenyl]-4-yl]amino}cyclohexanecarboxamide;
N-(cyanomethyl)-4-methyl-2-{[4'-(1-piperazinyl)[1,1'-biphenyl]-3-yl]oxy}pentanamide;
N-(cyanomethyl)-4-methyl-2-{[4'-(1-piperazinyl)[1,1'-biphenyl]-4-yl]oxy}pentanamide;
N-(cyanomethyl)-1-{[4'-(1-piperazinyl)[1,1'-biphenyl]-2-yl]amino}cyclohexanecarboxamide;
N-(cyanomethyl)-4-methyl-2-{[4'-(1-piperazinyl)[1,1'-biphenyl]-2-yl]oxy}pentanamide;
N-(cyanomethyl)-4-methyl-2-{[4'-(1-piperazinyl)[1,1'-biphenyl]-2-yl]methyl}pentanamide;
N-(cyanomethyl)-4-methyl-2-{[4'-(1-piperazinyl)[1,1'-biphenyl]-3-yl]methyl}pentanamide;
N-(cyanomethyl)-4-methyl-2-{[4'-(1-piperazinyl)[1,1'-biphenyl]-4-yl]methyl}pentanamide;
(2S)-N-(cyanomethyl)-4-methyl-2-({2-methyl-3-oxo-5-[4-(1-piperazinyl)phenyl]-2,3-dihydro-4-pyridazinyl}amino)pentanamide;
(2S)-N-(cyanomethyl)-4-methyl-2-({[4'-(1-piperazinyl)[1,1'-biphenyl]-3-yl]methyl}amino)pentanamide;
(2S)-N-(cyanomethyl)-4-methyl-2-({[4'-(1-piperazinyl)[1,1'-biphenyl]-4-yl]methyl}amino)pentanamide;
tert-butyl 4-{3'-[(1{[(cyanomethyl)amino]carbonyl }-3-methylbutoxy)methyl][1,1'-biphenyl]-4-yl}-1-piperazinecarboxylate;
tert-butyl 4-{4'-[(1-{[(cyanomethyl)amino]carbonyl}-3-methylbutoxy)methyl][1,1'-biphenyl]-4-yl}-1-piperazinecarboxylate;
tert-butyl 4-{2'-[(1-{[(cyanomethyl)amino]carbonyl}-3-methylbutoxy)methyl][1,1'-biphenyl]-4-yl}-1-piperazinecarboxylate;
N-(cyanomethyl)-4-methyl-2-{[4'-(1-piperazinyl)[1,1'-biphenyl]-2-yl]methoxy}pentanamide;
N-(cyanomethyl)-4-methyl-2-{[4'-(1-piperazinyl)[1,1'-biphenyl]-3-yl]methoxy}pentanamide;
N-(cyanomethyl)-4-methyl-2-{[4'-(1-piperazinyl)[1,1'-biphenyl]-4-yl]methoxy}pentanamide;
[(3S)-3-isobutyl-2-oxo-2,3-dihydroimidazo[2,1-a]thieno[3,4-c]isoquinolin-1(11bH)-yl]acetonitrile;
[(3S)-3-isobutyl-2-oxo-2,3-dihydrofuro[3,2-c]imidazo[1,2-a]thieno[3,4-e]pyridin-1(10bH)-yl]acetonitrile;
N-(cyanomethyl)-1-(1-bromophenyl)piperidine-2-carboxamide;
1-{4'-[4-(tert-butyloxycarbonyl)piperazin-1-yl]-1,1'-biphenyl-4-yl}-N-(cyanomethyl)-piperidine-2-carboxamide;
1-[4'-(piperazin-1-yl)-1,1'-biphenyl4-yl]-N-(cyanomethyl)-piperidine-2-carboxamide;
1-{3'-[4-(piperidin-1-yl)piperidin-1-yl]-1,1'-biphenyl-3-yl}-N-(cyanomethyl)-piperidine-2-carboxamide;
1-{3'-[2-(4-methylpiperazin-1-yl)thiazol-4-yl]-1,1'-biphenyl-3-yl}-N-(cyanomethyl)-piperidine-2-carboxamide;
1-{4'-[4-(morpholin-4-yl)piperidin-1-yl]-1,1'-biphenyl-3-yl}-N-(cyanomethyl)-piperidine-2-carboxamide;
1-{3'-(piperazin-1-yl)-1,1'-biphenyl-3-yl}-N-(cyanomethyl)-piperidine-2-carboxamide;
1-{4'-[2-(4-methylpiperazin-1-yl)thiazol-4-yl]-1,1'-biphenyl-3-yl}-N-(cyanomethyl)-piperidine-2-carboxamide;
1-{3'-[4-(morpholin-4-yl)piperidin-1-yl]-1,1'-biphenyl-3-yl}-N-(cyanomethyl)-piperidine-2-carboxamide;
1-(4'-trifluoromethyl-1,1'-biphenyl-3-yl)-N-(cyanomethyl)-piperidine-2-carboxamide;
1-(2',3'difluoro-1,1'-biphenyl-3-yl)-N-(cyanomethyl)-piperidine-2-carboxamide;
1-{3'-[4-(tert-butyloxycarbonyl)piperazin-1-yl]-1,1'-biphenyl-4-yl}-N-(cyanomethyl)-piperidine-2-carboxamide;
1-[3'-(piperazin-1-yl)-1,1'-biphenyl-4-yl]-N-(cyanomethyl)-piperidine-2-carboxamide;
1-{4'-[4-(tert-butyloxycarbonyl)piperazin-1-yl]-1,1'-biphenyl-2-yl}-N-(cyanomethyl)-piperidine-2R-carboxamide;
N-(cyanomethyl)-1-(3-bromophenyl)piperidine-2R-carboxamide;
1-{3'-(piperazin-1-yl)-1,1'-biphenyl-3-yl}-N-(cyanomethyl)-piperidine-2R-carboxamide;
1-{3-[2-(4-morpholin-4-ylpiperazin-1-yl)thiazol-4-yl]-phenyl}-N-(cyanomethyl)-piperidine-2-carboxamide;
1-{3-[2-(piperazin-1-yl)thiazol-4-yl]-phenyl}-N-(cyanomethyl)-piperidine-2-carboxamide;
1-{3-[2-(4-methylhomopiperazin-1-yl)thiazol-4-yl]-phenyl}-N-(cyanomethyl)-piperidine-2-carboxamide;
N-(cyanomethyl)-1-(3-bromo-5-fluorophenyl)piperidine-2-carboxamide;
N-(cyanomethyl)-1-(3-bromo-6-fluorophenyl)piperidine-2-carboxamide;
N-(cyanomethyl)-1-(3-bromo-4-fluorophenyl)piperidine-2-carboxamide;
1-{5-fluoro-4'-[4-(tert-butyloxycarbonyl)piperazin-1-yl]-1,1'-biphenyl-3-yl}-N-(cyanomethyl)-piperidine-2-carboxamide;
1-{5-fluoro-4'-(piperazin-1-yl)-1,1'-biphenyl-3-yl}-N-(cyanomethyl)-piperidine-2-carboxamide;
1-{6-fluoro-4'-[4-(tert-butyloxycarbonyl)piperazin-1-yl]-1,1'-biphenyl-3-yl}-N-(cyanomethyl)-piperidine-2-carboxamide;
1-[6-fluoro4'-(piperazin-1-yl)-1,1'-biphenyl-3-yl]-N-(cyanomethyl)-piperidine-2-carboxamide;
N-(cyanomethyl)-1-(6-bromopyridin-2-yl)piperidine-2-carboxamide;
1-[6-(4-piperazin-1-ylphenyl)pyridin-2-yl]-N-(cyanomethyl)-piperidine-2-carboxamide;
1-{6-[4-(4-tert-butoxycarbonylpiperazin-1-yl)phenyl]pyridin-2-yl}-N-(cyanomethyl)-piperidine-2-carboxamide;
1-{5-[4-(4-tert-butoxycarbonylpiperazin-1-yl)phenyl]pyridin-3-yl}-N-(cyanomethyl)-piperidine-2-carboxamide;

1-{4-fluoro-[4'-[4-(tert-butyloxycarbonyl)piperazin-1-yl]-1,1'-biphenyl-3-yl}-N-(cyanomethyl)-piperidine-2-carboxamide;
1-[4-fluoro-4'-(piperazin-1-yl)-1,1'-biphenyl-3-yl]-N-(cyanomethyl)-piperidine-2-carboxamide;
1-{5-[4-(piperazin-1-yl)phenyl]pyridin-3-yl}-N-(cyanomethyl)-piperidine-2-carboxamide;
N1-(cyanomethyl)-N2-(2,2,3,3-tetrafluoro-1-phenylcyclopropyl)-L-leucinamide;
N1-(cyanomethyl)-N2-(3,3,4,4-tetrafluoro-1-phenylcyclopentyl)-L-leucinamide;
N1-(cyanomethyl)-N2-(2,2-difluoro-5-phenylcyclopentyl)-L-leucinamide;
N1-(cyanomethyl)-N2-(2,2-difluoro-2,3-dihydro-1H-inden-1-yl)-L-leucinamide;
N1-(cyanomethyl)-N2-{1-[4-(N,N-dimethylglycyl)phenyl]cyclopropyl}-L-leucinamide;
1-{4-[2-(4-methyl-piperazin-1-yl)-thiazol-4-yl]-phenoxy}-cyclohexanecarboxylic acid cyanomethyl-amide;
2-(biphenyl-3-yloxy)-4-methyl-pentanoic cyanomethyl-amide;
2-(biphenyl-4-yloxy)-4-methyl-pentanoic cyanomethyl-amide;

and the pharmaceutically acceptable salts and N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739–1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396–1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteoporosis in cathepsin K-deficient mice. Proc. Natl. acad. Sci. USA 95:13453–13458; 1998.

Another embodiment of the invention is a method treating cancer in a mammal in need thereof, comprising administering to the mammal a therapeutically effective amount of any of the compounds or any of the pharmaceutical compositions described above. It is known in the literature that Cathepsin K is expressed in human breast carcinoma, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 December 1;57(23):5386–90.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration. It should be understood that topical routes of administration include transdermal delivery and patches.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol,.sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PIH; and the pharmaceutically acceptable salts and mixtures thereof.

"Organic bisphosphonate" refers to compounds of the chemical formula

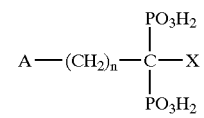

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-midazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 $\mu$g/kg body weight and preferably about 10 to about 2000 $\mu$g/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163–172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (5 Feb. 1996) and U.S. Pat. Nos. 4,782,084 and 4,885,314. The term HG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

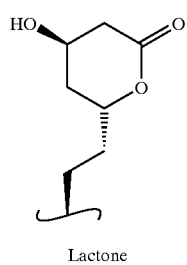

Lactone

I

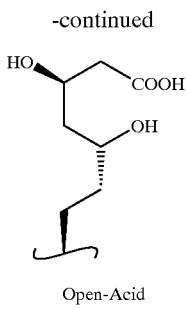

Open-Acid

II

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolaamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ and $\alpha_6\beta_4$ integrins. H. N. Lode and coworkers in PNAS USA 96: 1591–1596 (1999) have observed synergistic effects between an antiangiogenic $\alpha v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690–709 (1993). Studies have demonstrated the clinical benefits of parathyroid hormone in stimulating bone formation and thereby increasing bone mass and strength. Results were reported by R M Neer et al., in New Eng J Med 344 1434–1441 (2001).

In addition, parathyroid hormone-related protein fragments or analogues, such as PTHrP-(1–36) have demonstrated potent anticalciuric effects [see M. A. Syed et al., "Parathyroid hormone-related protein-(1–36) stimulates renal tubular calcium reabsorption in normal human volunteers: implications for the pathogenesis of humoral hypercalcemia of malignancy," JCEM 86: 1525–1531 (2001)] and may also have potential as anabolic agents for treating osteoporosis.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "bone resorption," as used herein, refers to the process by which osteoclasts degrade bone.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/ minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereo-chemistry of Carbon Compounds,* John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

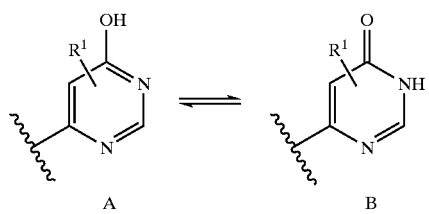

When any variable (e.g. $R^a$, $R^b$, $R^7$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is to be understood that when n is zero, $R^5$ is bonded directly to D, which is optionally substituted.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The term "optional" or "optionally" means that the subsequently described event or circumstance may or may not occur, and that the description includes instances where the event or circumstance occurs and instances in which it does not. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear, branched, or cyclic arrangement. For example, "$C_1$–$C_{10}$ alkyl" specifically includes methyl, ethyl, propyl, butyl, pentyl, hexyl, heptyl, octyl, nonyl, decyl, and so on. "Alkoxy" represents an alkyl group of indicated number of carbon atoms attached through an oxygen bridge.

The term "cycloalkyl" or "carbocycle" shall mean cyclic rings of alkanes of three to eight total carbon atoms, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight, branched or cyclic, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight or branched, containing from 2 to 10 carbon atoms and at least 1 carbon to carbon triple bond. Up to 3 carbon-carbon triple bonds may be present. Thus, "C2–C6 alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$)alkylene-aryl. If aryl is taken to be phenyl, this definition would include phenyl itself as well as —$CH_2Ph$, —$CH_2CH_2Ph$, $CH(CH_3)$ $CH_2CH(CH_3)Ph$, and so on.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic or bicyclic ring of up to 10 atoms in each ring, wherein at least one ring is aromatic and contains from 1 to 4 heteroatoms selected from the group consisting of O, N and S, SO and $SO_2$. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O).

The term "haloalkyl" means an alkylradical as defined above that is substituted with one or more halogen atoms, preferably one to three halogen atoms.

The term "hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

The term "heterocycle" or "heterocyclyl" as used herein is intended to mean a 5- to 10-membered nonaromatic ring containing from 1 to 4 heteroatoms selected from the group consisting of O, N, S, SO and $SO_2$, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "acylamino" means the radical —NHCOR where R is an alkyl group as defined above.

The term "acylaminoalkyl" means an alkyl radical as defined above that is substituted with one or two —NHCOR groups where R is an alkyl group as defined above, e.g. acetylaminomethyl and the like.

The term "alkylamino" means the radical —NHR where R is an alkyl group as defined above, i.e. methylamino, ethylamino, and the like.

The term "alkylaminoalkyl" means an alkyl radical as defined above that is substituted with one or two —NHR where R is an alkyl group as defined above, i.e. methylaminomethyl, ethylaminomethyl, and the like.

The term "dialkylamino" means the radical —NRR where R is independently alkyl as defined above, i.e. dimethylamino and the like.

The term "hydroxycarbonyl" means the radical as defined above, i.e., methoxycarbonylmethyl and the like.

The term "hydroxycarbonylalkoxy" means the radical —OCOOH.

The term "alkylcarbonyloxy" means the radical —OCOOR where R is alkyl as defined above, i.e., methoxycarbonyloxy and the like.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.,* 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:

| | |
|---|---|
| AcOH = | acetic acid |
| Boc = | t-butyloxycarbonyl |
| $Boc_2O$ = | di-tert-butyl dicarbonate |
| BuLi = | butyl lithium |
| $CCl_4$ = | carbon tetrachloride |
| $CH_2Cl_2$ = | methylene chloride |
| $CH_3CN$ = | acetonitrile |
| $CHCl_3$ = | chloroform |
| $Cs_2CO_3$ = | cesium carbonate |
| CuI = | copper iodide |
| DIAD = | diisopropyl azodicarboxylate |
| DMA = | N,N-dimethyl acetamide |
| DMAP = | 4-(dimethylamino)pyridine |
| DMF = | N,N-dimethylformamide |
| DMSO = | dimethylsulfoxide |
| DPPA = | diphenylphosphoryl azide |
| EDCI = | 1-(3-dimethylaminopropyl)-3-ethylcarbodiimide hydrochloride |
| $Et_2O$ = | diethyl ether |
| $Et_3N$ = | triethylamine |
| EtOAc = | ethyl acetate |
| EtOH = | ethanol |
| HATU = | o-(7-azabenzotriazol-1-yl)-N,N,N',N'-tetramethyluronium hexafluorophosphate |
| HOAc = | acetic acid |
| KCN = | potassium cyanide |
| $K_2CO_3$ = | potassium carbonate |
| $KOBu^t$ = | potassium tert-butoxide |
| $LiAlH_4$ = | lithium aluminum hydride |
| LiOH = | lithium hydroxide |
| mCPBA = | metachloroperbenzoic acid |
| MeOH = | methanol |
| MeOTf = | methyl triflate |
| $MeSO_3H$ = | methane sulfonic acid |
| $MgSO_4$ = | magnesium sulfate |
| Ms = | methanesulfonyl = mesyl |
| MsCl = | methanesulfonyl chloride |
| MTBE = | tert-butyl methyl ether |
| $NaBH_4$ = | sodium borohydride |
| NaH = | sodium hydride |
| $Na_2CO_3$ = | sodium carbonate |
| $NaHCO_3$ = | sodium hydrogencarbonate |
| NaOCl = | sodium hypoclorite |
| NaOH = | sodium hydroxide |
| $Na_2SO_4$ = | sodium sulfate |
| NBS = | N-bromosuccinimide |
| NCS = | N-chlorosuccinimide |
| $NH_3$ = | ammonia |
| $NH_4Cl$ = | ammonium chloride |
| Pd/C = | palladium on carbon |
| $PdCl_2(dppf)$ = | [1,1'-bis(diphenylphosphino)ferrocene]dichloropalladium(II) |
| $Pd_2(dba)_3$ = | tris(dibenzylideneacetone)dipalladium(0) |
| PG = | protecting group |
| $POCl_3$ = | phosphorus oxychloride |
| $PPh_3$ = | triphenylphosphine |
| PPTS = | pyridinium p-toluenesulfonate |
| $iPr_2Nli$ = | lithium diisopropyl amide |
| PyBOP = | benzotriazol-1-yloxytris(pyrrolidino)phosphonium-hexafluorophosphate |
| rt = | room temperature |
| sat. aq. = | saturated aqueous |
| TFA = | trifluoroacetic acid |
| THF = | tetrahydrofuran |
| tlc = | thin layer chromatography |
| Troc = | trichloroethyloxycarbonyl |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Substituent numbering as shown in the schemes does not necessarily correlate to that used in the claims.

GENERAL SYNTHESIS

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989); Organic Reactions, Volumes 1–40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of the present invention in which X=—NH—, n is 1 or 2, and other groups are as defined in the Summary of the Invention may be prepared according to Schemes 1a, 1b or 1c as illustrated below.

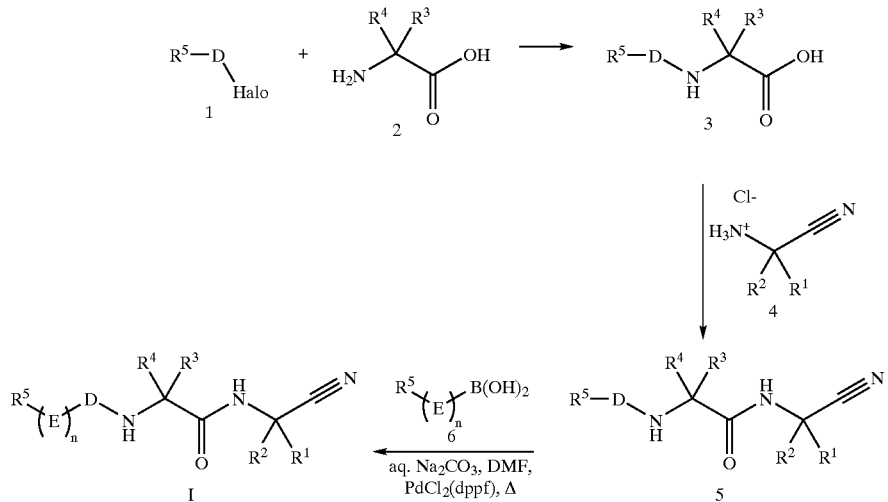

Scheme 1a

Treatment of the alpha-aminoacetic acid of formula 2 with a compound of formula 1 provides a compound of formula 3. When the reacting halogen in compound 1 is a bromide, the reaction may be carried out in the presence of copper iodide and a base such as potassium carbonate in a suitable organic solvent such as dimethylacetamide, and the like. In cases where the reactive halogen is a chloride, a direct nucleophilic displacement may be possible when carried out in the presence of a base such as potassium carbonate.

Compounds of formula 1, 2 and 4 are commercially available or may be synthesized by methods well known in the art. For example, 3,4-dibromothiophene, chlorophenyl tetrazole, leucine and aminoacetonitrile hydrochloride are commercially available.

Treatment of 3 with 2-aminoacetonitrile of formula 4 in the presence of a suitable coupling agent such as PyBOP affords compound 5. The reaction is carried out in a suitable organic solvent such as dimethylformamide, dioxane, and the like and in the presence of an organic base such as triethylamine, diisopropylamine, pyridine, and the like.

In the instance where $R^5$ is a halogen, compound 5 may be converted to compounds of Formula I where n is 1 or 2 by reacting 5 with a boronic acid compound of formula 6 where n is 1 or 2, and E and $R^5$ are as defined in the Summary of the Invention. The reaction is carried out in the presence of a palladium catalyst such as $PdCl_2(dppf)$, a base such as sodium carbonate and in a suitable organic solvent such as dimethylformamide.

Compounds of formula 6 are either commercially available or they may be prepared from the corresponding aryl bromide or triflate by methods well known in the art.

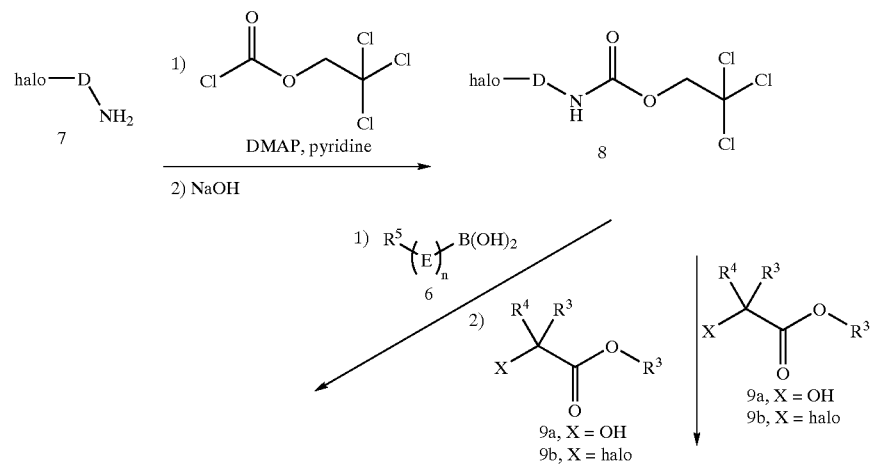

Scheme 1b

-continued

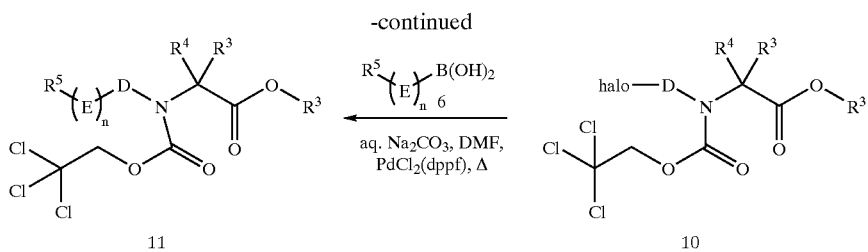

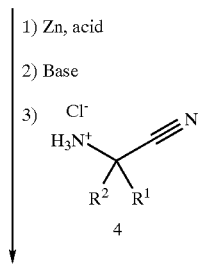

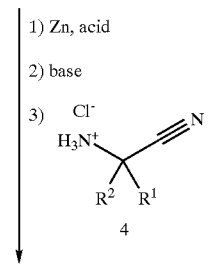

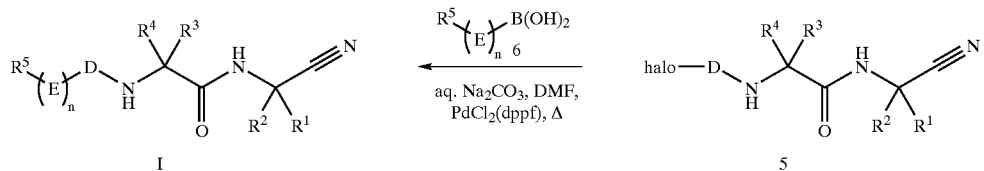

Alternative syntheses of compounds of the present invention in which X=—NH— using Mitsonobu or alkylation chemistry are depicted in Scheme 1b. Treatment of compound 7 with 2,2,2-trichloroethyl chloroformate in the presence of suitable bases such as DMAP and pyridine in an appropriate organic solvent such as dichloromethane may afford the di-troc protected amine. The mono-troc compound 8 may then be obtained by base cleavage of one of the troc groups. Alternatively the mono-troc compound 8 may be obtained directly from compound 7. Using a Mitsonobu route, the troc amine 8 is reacted with the alcohol 9a using reagents such as triphenyl phosphine and diisopropyl azodicarboxylate in the presence of a suitable organic solvent such as DMF.

Alternatively, the troc amine 8 may be alkylated with the corresponding halogenated compound 9b using a base such as sodium hydride. Compounds 9a and 9b are either commercially available or are described in the literature. Either route generates compound 10 which may then be elaborated to compounds of Formula I by one of two sequences: (i) Suzuki reaction with boronic acids of general structure 6 to yield compounds 11 followed by removal of the troc group with zinc in the presence of an appropriate acid such as KH$_2$PO$_4$, base hydrolysis of the ester and coupling with aminoacetonitrile 4 or (ii) removal of the troc group of 10 with zinc in the presence of an appropriate acid such as KH$_2$PO$_4$, base hydrolysis of the ester and coupling with aminoacetonitrile 4 followed by Suzuki reaction between the generated compound 5 and the boronic acid 6. The intermediate 11 may also be obtained by reversing the order of the Mitsonobu/alkylation step and the Suzuki reaction with boronic acid 6 as illustrated in Scheme 1b.

In Scheme 1b, the synthesis commences with the halogenated aryl/heteroaryl amine 7. Compounds of general structure 7 are either commercially available or may be prepared according to Schemes 11 and 12.

Instead of commencing with the halogenated aryl/heteroaryl amine 7, one may synthesize compounds of the present invention in which X=—NH— by using the above described Mitsonobu and alkylation chemistry starting with the non-halogenated intermediate 13 (see Scheme 1c). Compound 13, in turn, may be prepared as described in Scheme 1c from the aryl/heteroaryl amine 12 either by forming the mono-troc 13 directly or forming the di-troc intermediate followed by base cleavage of one of the troc groups. Compounds of general structure 12 are either commercially available or may be prepared according to Schemes 13 and 14. Compound 14 may be elaborated to compounds of Formula I by one of three possible sequences as illustrated in Scheme 1c.

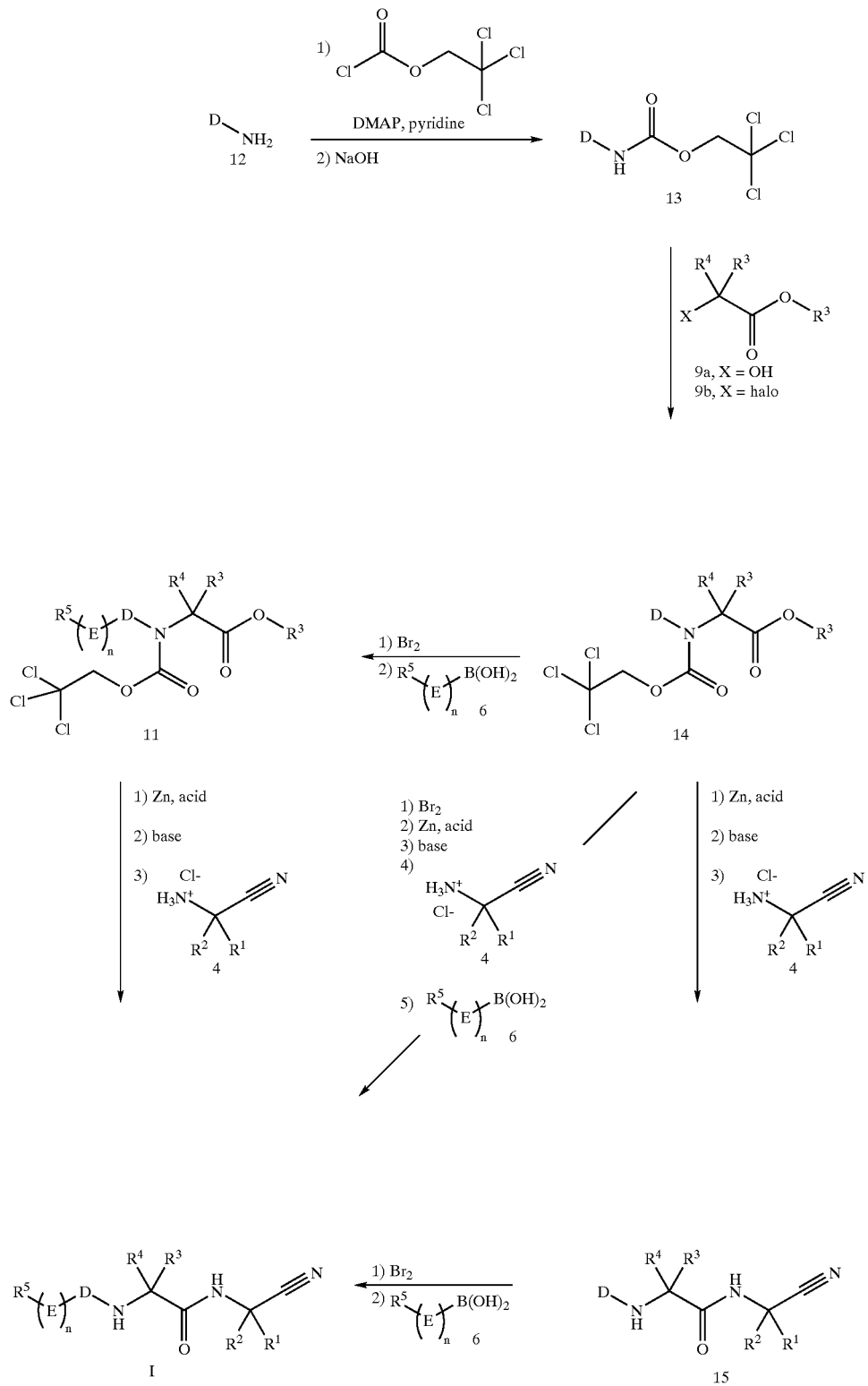

Compounds of the present invention where X=—NH—, —O—, —S—, —C($R^7$)($R^8$)O—, —C($R^7$)($R^8$)NH—, —C($R^7$)($R^8$)S—, —SO$_2$—, —C($R^7$)($R^8$)SO$_2$—, n is 1 or 2, and other groups are as defined in the Summary of the Invention may be prepared according to Schemes 2a and 2b illustrated below.

formula 18. Suitable bases are aqueous lithium hydroxide, sodium hydroxide, and the like. Suitable solvents are alcoholic solvents such as methanol, ethanol, and the like. A compound of formula 18 may then be converted to a corresponding compound of Formula I where n is 1 or 2 as described in Scheme 1a above.

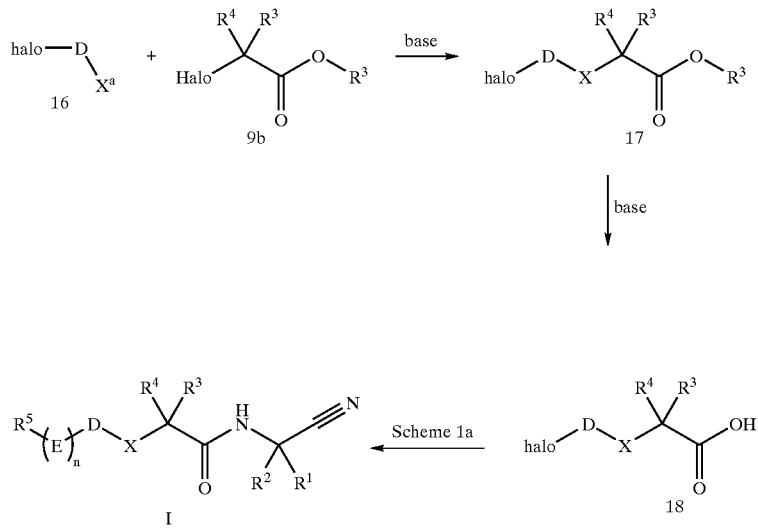

Treatment of a compound of formula 16 where $X^a$ is —NH$_2$, —OH, —SH, —C($R^7$)($R^8$)NH$_2$, —C($R^7$)($R^8$)OH, or —C($R^7$)($R^8$)SH where $R^7$ and $R^8$ are as defined in the Summary of the Invention with the compound of formula 9b provides a compound of formula 17 where X is —NH—, —O—, —S—, —C($R^7$)($R^8$)NH—, —C($R^7$)($R^8$)O— or —C($R^7$)($R^8$)S—, respectively. The reaction is carried out in the presence of a strong non-nucleophilic base such as sodium hydride, potassium tert-butoxide, and the like and in a suitable organic solvent such as dimethylformamide, tetrahydrofuran, and the like. Hydrolysis of the ester group in 17 under basic reaction conditions provides a compound of Alternatively, treatment of a compound of formula 16 where $X^a$ is —NH$_2$, —OH, —SH, —C($R^7$)($R^8$)NH$_2$, —C($R^7$)($R^8$)OH, or —C($R^7$)($R^8$)SH where $R^7$ and $R^8$ are as defined in the Summary of the Invention with the boronic acid 6 as previously described provides compound 19. Compound 19 may then be reacted with compound of formula 9b as described in Scheme 2a to provide a compound of formula 20 where X is —NH—, —O—, —S—, —C($R^7$)($R^8$)NH—, —C($R^7$)($R^8$)O— or —C($R^7$)($R^8$)S—, respectively. Compound 20 may be elaborated as previously described to a corresponding compound of Formula I.

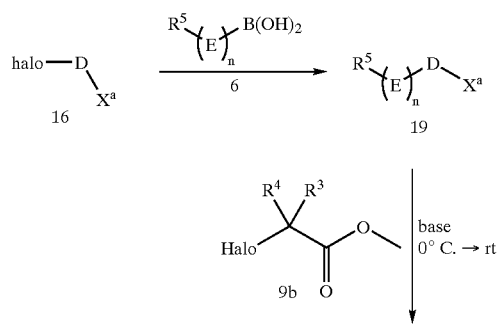

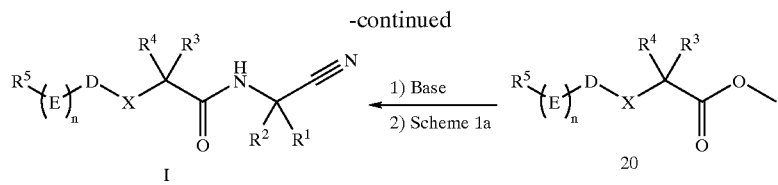

Alternatively, a compound of Formula I where X is —O— may be prepared by reacting a 2,2,2-trichloroethanol compound of formula CCl$_3$—C(R$^3$R$^4$)—OH with a compound of 16 where X$^a$ is —OH to provide a compound of formula 18 which is then converted to a compound of Formula I as described in Scheme 1a.

A compound of Formula I where X is —SO$_2$— or —C(R$^7$)(R$^8$)SO$_2$— may be prepared from a corresponding compound of Formula I where X is —S— or —C(R$^7$)(R$^8$)S— under oxidation reaction conditions well known in the art.

Compounds of the present invention in which X=—CH$_2$NH— may be prepared according to Scheme 3, as illustrated below.

Scheme 3

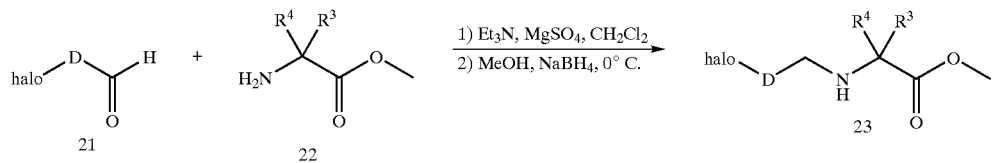

Condensation of an aldehyde of formula 21 with 2-aminoacetate of formula 22, followed by reduction of the resulting imine with a suitable reducing agent such as sodium borohydride provides a compound of formula 23. Hydrolysis of the ester group in 23 under basic reaction conditions provides the corresponding acid 24 which is then converted to a compound of Formula I as described in Scheme 1a above. Compounds 21 and 22 are either commercially available or may be synthesized according to procedures well known in the art.

Compounds of the present invention in which X=—CH$_2$— may be prepared according to Scheme 4 illustrated below.

Scheme 4

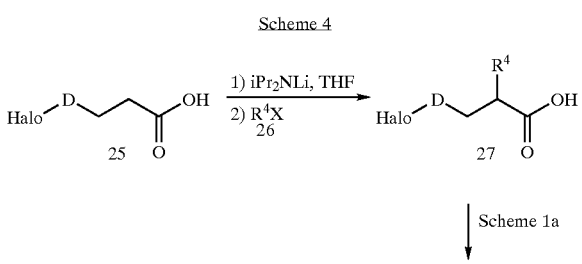

-continued

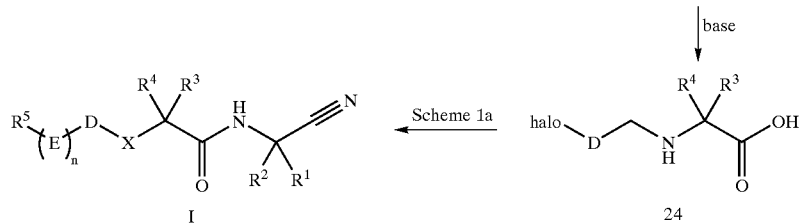

Alkylation of a compound of formula 25 with an alkylating agent of formula 26 where R$^4$ is alkyl and X is a suitable leaving group such as halo, tosylate, mesylate, and the like, provides a compound of formula 27 which is then converted to a compound of Formula I where R$^4$ is alkyl as described in Scheme 1a above. The alkylation reaction is carried out in the presence of a base such as butyllithium, lithium isopropylamide, and the like and in a suitable organic solvent such as tetrahydrofuran, diethyl ether, and the like. Compounds 25 and 26 are either commercially available or may by synthesized according to procedures well known in the art.

Compounds of Formula I where X is —NR$^6$— and R$^6$ and R$^4$ form a ring may be prepared as illustrated in Scheme 5a below.

Compounds of formula 30 in which R$^5$ is halo may then be elaborated to compounds of general formula I in which n=1 or 2 via a Suzuki reaction with boronic acid 6 and then coupling to an aminoacetonitrile of formula 4 as previously described. Alternatively, compound 30 may be coupled with an aminoacetonitrile of formula 4 to provide compounds of

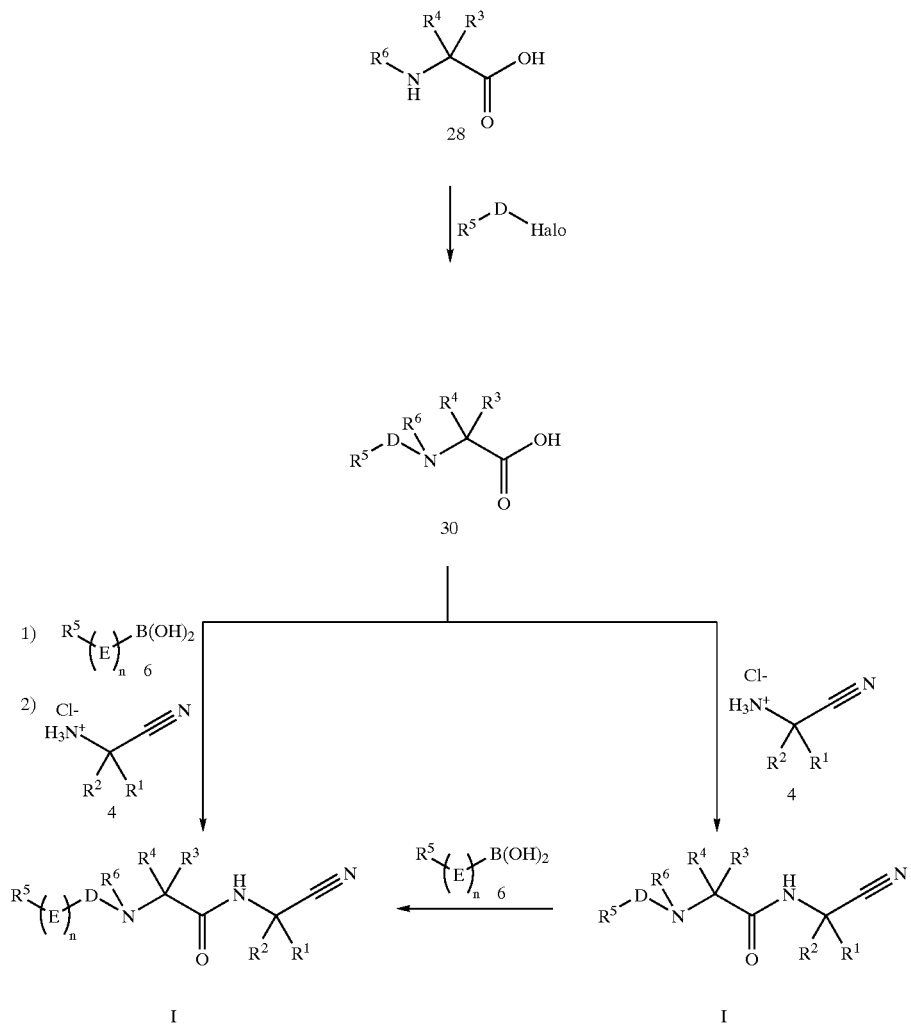

Treatment of a compound of formula 28 (where R$^6$ and R$^4$ form a 4–8 membered ring as described in the Summary of the Invention) with a compound of formula 29 provides a compound 30. This reaction may be performed in the presence of copper iodide and a base such as potassium carbonate in a suitable organic solvent such as dimethylacetamide, and the like (as described in Scheme 1a). Alternatively, the reaction may be carried out in the presence of a palladium(0) catalyst (i.e. Pd$_2$(dba)$_3$), a base such as cesium carbonate or sodium tert-butoxide and in a suitable organic solvent such as toluene.

Compounds of formula 28 and 29 are either commercially available or may be prepared according to procedures well known in the art.

general formula I in which n=0. Compounds of general formula I in which n=0 and R$^5$ is halo, in turn, may be elaborated to compounds of general formula I in which n=1 or 2 using the boronic acid 6 as previously described.

Compounds of Formula I where X=—NR$^6$— and R$^6$ and R$^4$ are taken together to form a 4–8 membered ring system as described in the Summary of the Invention and D=thiazole may be prepared as illustrated in Scheme 5b below.

Scheme 5b

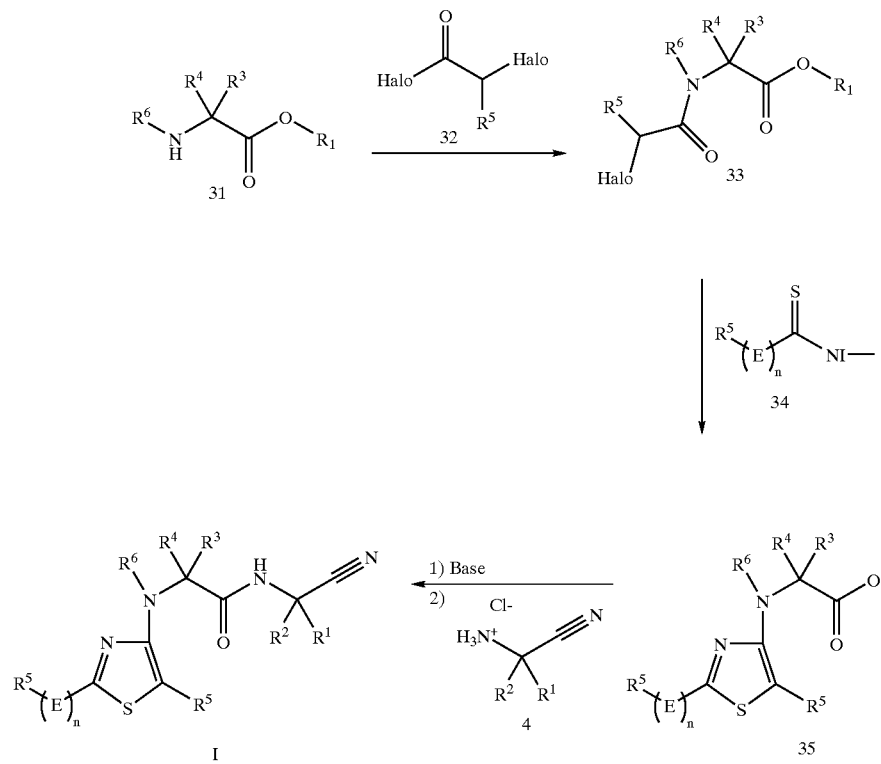

Treatment of a compound of formula 31 (where $R^6$ and $R^4$ form a 4–8 membered ring as described in the Summary of the Invention) with a halo acetyl halide of formula 32 in the presence of a base such as triethylamine and a suitable organic solvent such as acetonitrile provides compound 33. Compound 33 may then be condensed with a thioamide of formula 34 in the presence of a suitable organic solvent such as DMF. This generates compounds of formula 35 which, in turn, may be elaborated to compounds of formula 1 where X is —$NR^6$— and $R^6$ and $R^4$ form a 4–8 membered ring and D is a thiazole by basic hydrolysis of the ester group of 35 and coupling with an aminoacetonitrile of formula 4.

Compound 31, 32 and 34 are either commercially available or may be synthesized by methods well known in the art.

Compounds of Formula I where $R^3$ is hydrogen and $R^4$ is 1-substituted 1,1-dimethylcyclopropane may be prepared as illustrated in Scheme 6 below.

Scheme 6

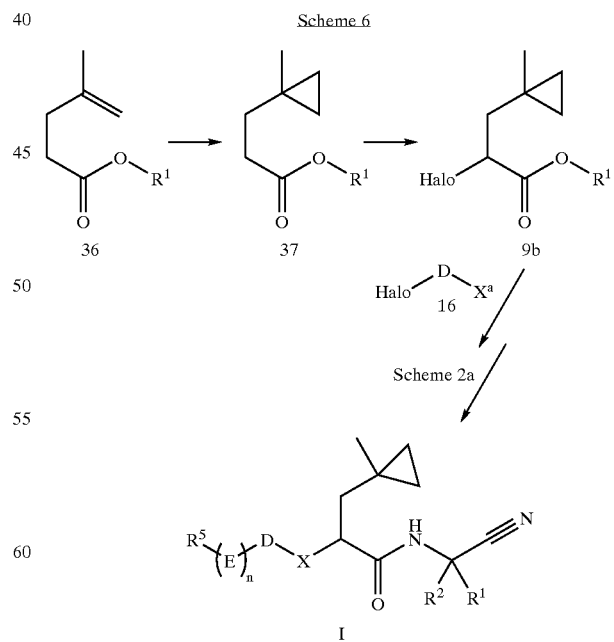

Compound of formula 36 may be cyclopropanated to compound 37 using such reagents as Pd(II) acetate and diazomethane in a suitable organic solvent such as diethyl ether. Compounds of formula 37 may be halogenated using procedures well known in the art. For example, compound 37 could be treated with LDA and TMSCl followed by bromination with NBS to yield a brominated compound of formula 9b. Elaboration of compound 9b to compounds of formula I where $R^3$ is hydrogen and $R^4$ is 1-substituted 1,1-dimethylcyclopropane may proceed as described in Scheme 2a.

Compounds of Formula I where $R^5$ is $(R^a)(R^b)CNHC(R^a)(R^b)$— may be prepared as illustrated in Schemes 7a and 7b below. $R^a$ and $R^b$ are as described in the Summary of the Invention.

such as sodium carbonate and in a suitable organic solvent such as DMF. Compound 40 in which PG represents any known, compatible nitrogen protecting group such as BOC, is either commercially available or may be prepared according to procedures well known in the art. Following removal of the nitrogen protecting group (i.e. methanesulfonic acid removal of a BOC protecting group) compound 41 may be elaborated to the final compounds of formula 42 using standard reductive amination conditions (see Scheme 3 for an example of a reductive amination). Hence compound 64a is condensed with the amine of 41 using a dehydrating reagent such as $MgSO_4$ and then reduction of the resulting imine with a suitable reducing agent such as sodium boro-

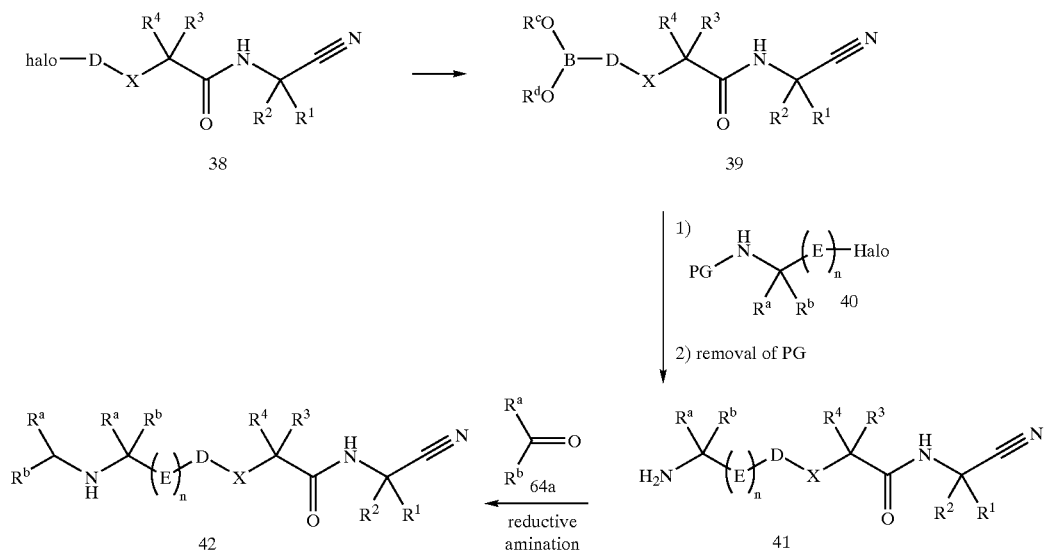

Scheme 7a

In Scheme 7a above, the halogenated compound of formula 38 (see Scheme 1a, compound 5, Scheme 2a or 2b) may be converted to a boronic acid 39 (where $R^c$ and $R^d$ are hydrogens) or boronic ester 39 (where $R^c$ and $R^d$ are optionally substituted alkyls or where $R^c$ and $R^d$ may be attached to form a $C_{3-8}$ cycloalkyl ring wherein said ring is optionally substituted) using conditions well known in the art. A Suzuki reaction between 39 and 40 may be carried out in the presence of a palladium catalyst such as $PdCl_2(dppf)$, a base hydride affords compound 42. Compound 64a in which $R^a$ and $R^b$ are defined as described in the Summary of the Invention either commercially available or may be synthesized by methods well known in the art.

Alternatively, compounds of Formula I where $R^5$ is $(R^a)(R^b)NC(R^a)(R^b)$— and $R^a$ and $R^b$ are defined as in the Summary of the Invention may be prepared as illustrated in Scheme 7b below.

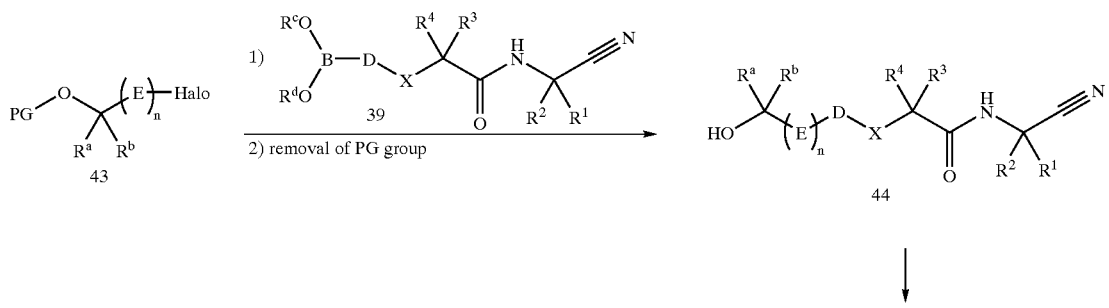

Scheme 7b

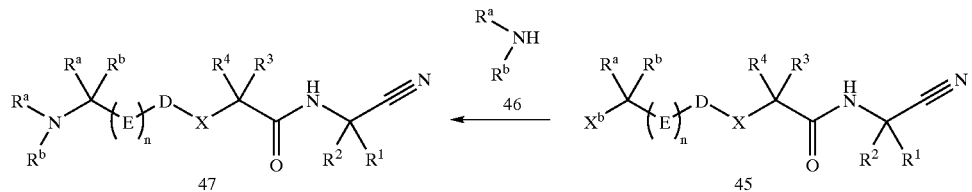

In Scheme 7b above, a Suzuki reaction between 39 and 43 may be carried out in the presence of a palladium catalyst such as PdCl$_2$(dppf), a base such as sodium carbonate and in a suitable organic solvent such as DMF. Compound 39 is prepared as described in Scheme 7a. Compound 43 in which PG represents any known, compatible oxygen protecting group, is either commercially available or may be prepared according to procedures well known in the art. Following removal of the oxygen protecting group, compound 44 may be converted to compound 45 in which $X^b$ is either a halo, mesylate or tosylate group. In cases where $X^b$ is a halogen, compound 45 may be obtained by treating compound 44 with reagents such as NBS, triphenylphospine and imidazole. In cases where $X^b$ is a mesylate or tosylate, compound 45 may be obtained by procedures well known in the art. Compound 45 may be elaborated to the final compounds of formula 47 by displacing $X^b$ with an amine of formula 46. In cases where $R^a$ and $R^b$ are alkyl, hydrogen or are taken together to form a C$_{3-8}$ cycloalkyl ring, this reaction may proceed by using an excess of the amine 46 in a suitable organic solvent such as DMF. In cases where either $R^a$ and $R^b$ are aryl or heteroaryl, a strong base such as sodium hydride may be required.

Compounds of Formula I where $R^5$ is $(R^a)(R^b)NCH_2C$ $(R^a)(R^b)$— and $R^a$ and $R^b$ are as described in the Summary of Invention may be prepared as illustrated in Scheme 8 below.

Scheme 8

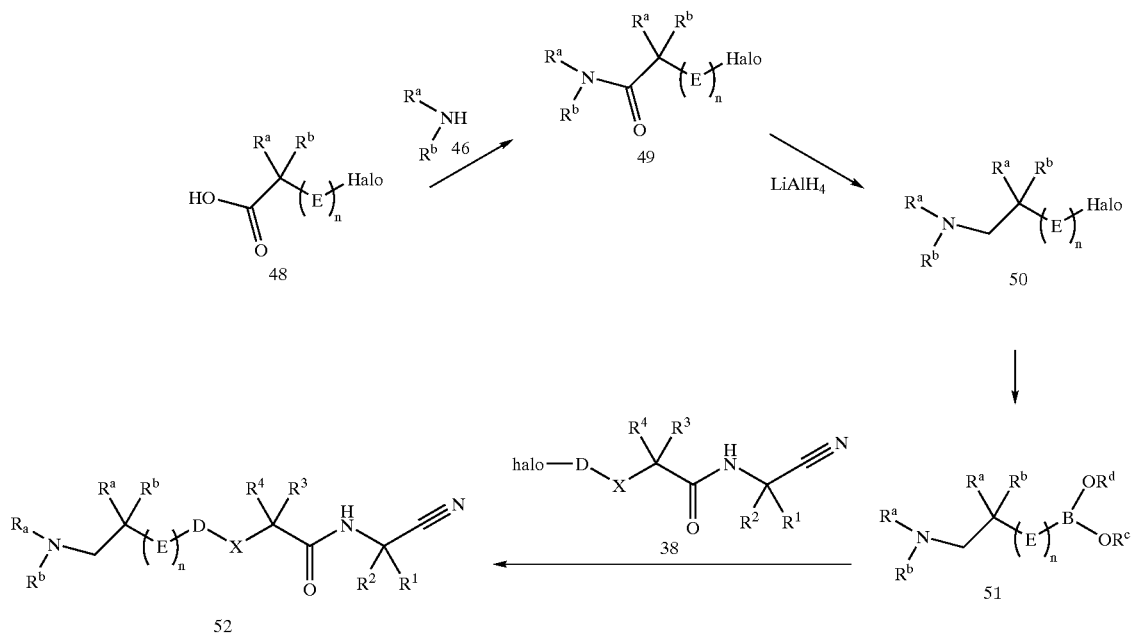

Compounds of formula 46 and 48 in which $R^a$ and $R^b$ are defined as described in the Summary of Invention may be coupled in the presence of a suitable coupling agent such as PyBOP to afford compound 49. The reaction is carried out in a suitable organic solvent such as dimethylformamide, dioxane, and the like and in the presence of an organic base such as triethylamine, diisopropylamine, pyridine, and the like. Compounds 46 and 48 are either commercially available or may be prepared using methods well known in the art.

Reduction of the carbonyl in compound 49 may be carried out using a reducing agent such as LiAlH$_4$ to provide the amine 50. The halogenated compound 50 may be converted to the boronic acid 51 (where $R^c$ and $R^d$ are hydrogens) or boronic ester 51 (where $R^c$ and $R^d$ are optionally substituted alkyls or where $R^c$ and $R^d$ may be attached to form a $C_{3-8}$ cycloalkyl ring wherein said ring is optionally substituted) using conditions well known in the art. Finally, compound 51 may be elaborated to the final compounds of formula 52 by Suzuki reaction with compound 38 as previously described.

Compounds of Formula I where $R^5$ is $(R^a)(R^b)NC(R^a)(R^b)C(O)$— and $R^a$ and $R^b$ are as described in the Summary of Invention may be prepared as illustrated in Scheme 9 below.

be attached to form a $C_{3-8}$ cycloalkyl ring wherein said ring is optionally substituted) using conditions well known in the art.

The halogenation of compound 55 to compound 56 may be obtained using standard halogenation reagents such as bromine or phenyltrimethyl ammonium tribromide in solvents such as MeOH or THF, respectively.

Compound 56 may be elaborated to the final compounds of formula 57 by displacing the halogen with an amine of formula 46. In cases where $R^a$ and $R^b$ are alkyl, hydrogen or

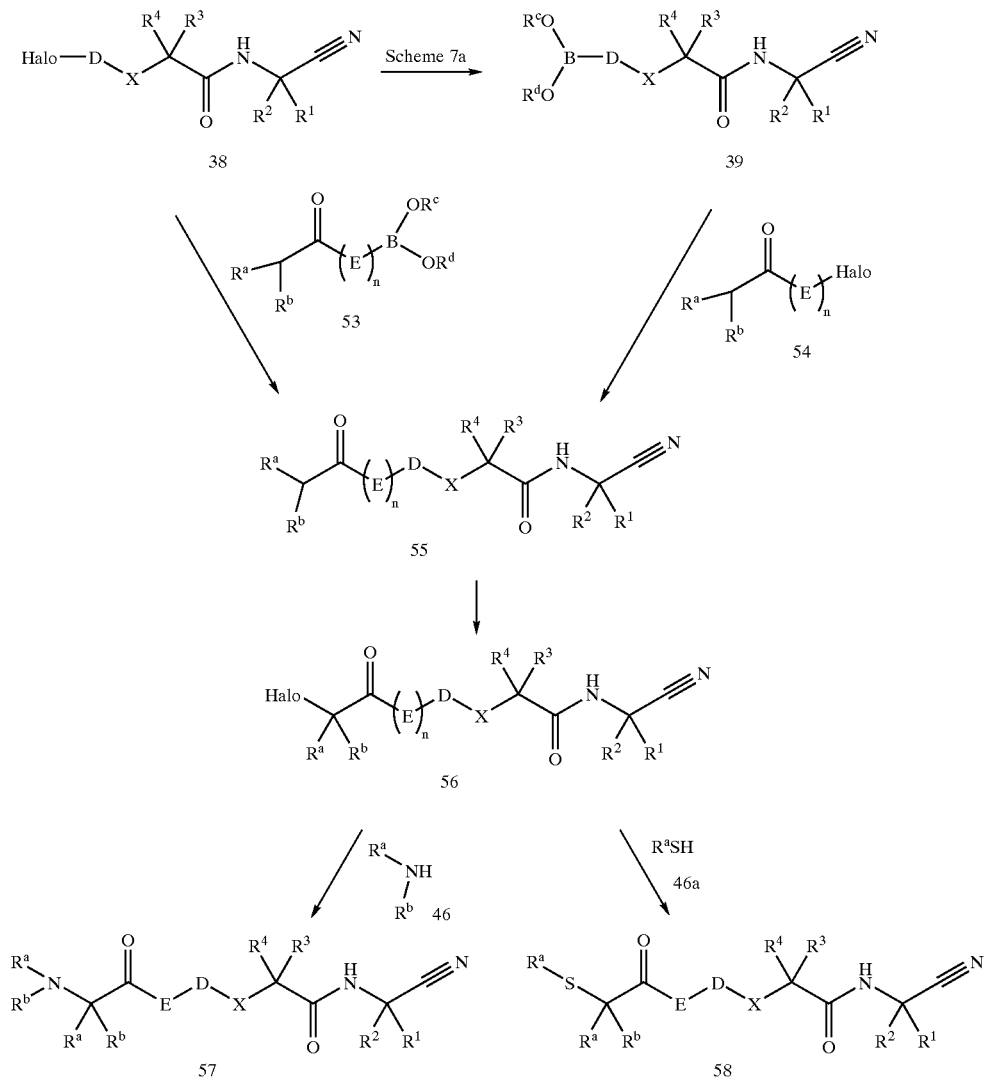

As illustrated in Scheme 9 above, compound 55 may be obtained via a standard Suzuki reaction between compounds 38 and 53 or between compounds 39 and 54. Compounds 38 and 39 are described in Scheme 7a. Compound 54 where $R^a$ and $R^b$ are as described in the Summary of Invention is either commercially available or may be synthesized using methods well known in the art. The halogenated compound of formula 54 may be converted to a boronic acid 53 (where $R^c$ and $R^d$ are hydrogens) or boronic ester 53 (where $R^c$ and $R^d$ are optionally substituted alkyls or where $R^c$ and $R^d$ may are taken together to form a $C_{3-8}$ cycloalkyl ring, this reaction may proceed by using an excess of the amine 46 in a suitable organic solvent such as DMF. In cases where either $R^a$ and $R^b$ are aryl or heteroaryl, a strong base such as sodium hydride may be required.

Compound 56 may be elaborated to the final compounds of formula 58 in which $R^5$ is $(R^a)SC(R^a)(R^b)C(O)$— by displacing the halogen with a thiol of formula 46a. This reaction may proceed using a base such as triethylamine and in a suitable organic solvent such as DMF.

Compounds of Formula I where one of the E rings is a piperazine and the piperazine nitrogen is substituted with $R^5$ may be obtained as illustrated in Scheme 10 below.

pound 64b with compound 59 using a dehydrating reagent such as $MgSO_4$ and then reduction of the resulting imine with a suitable reducing agent such as sodium borohydride.

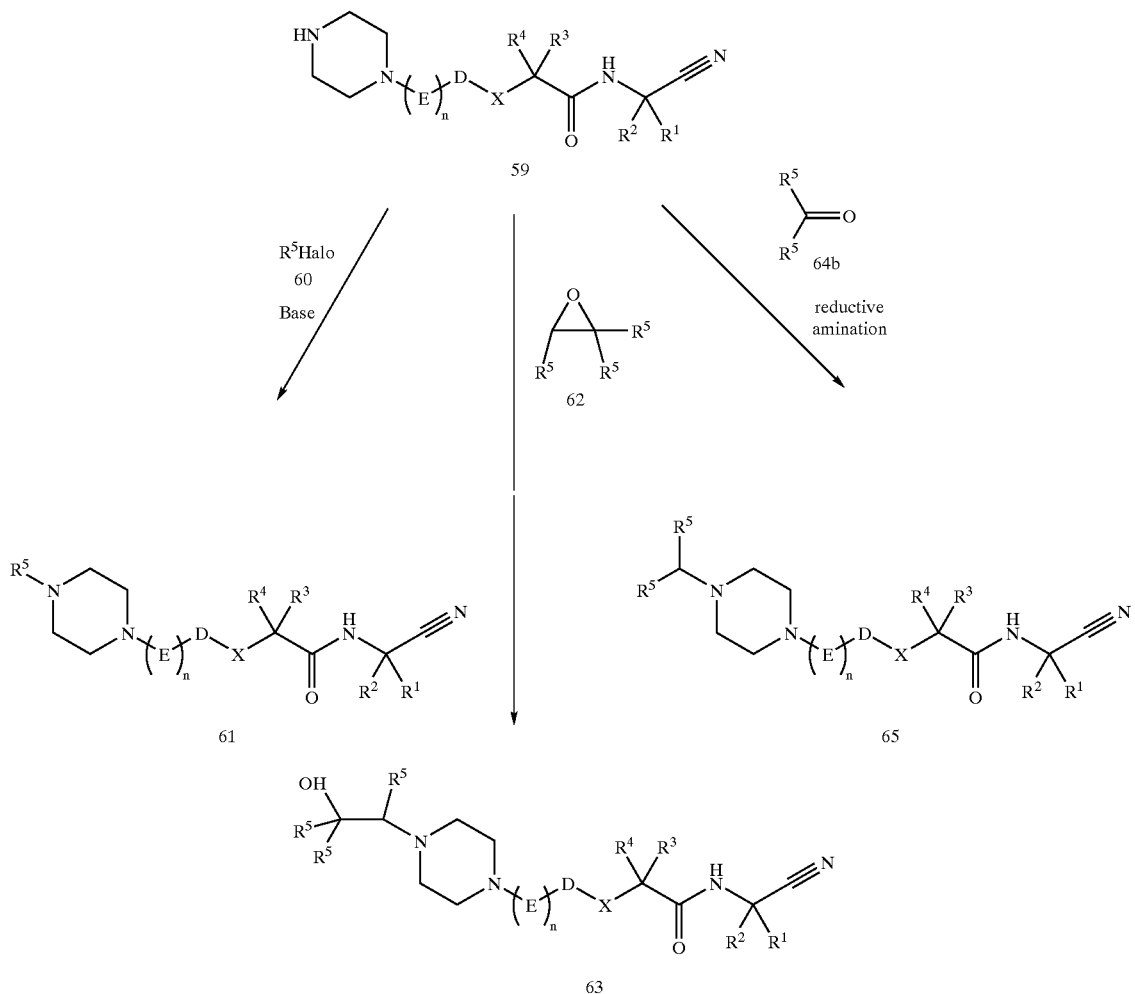

Scheme 10

A compound of formula 59 where one of the E rings is a piperazine may be converted to compounds of formula 61 as illustrated in Scheme 10 above. The alkylation of the piperazine nitrogen may proceed with a halogenated compound of formula 60 in which $R^5$ is as described in the Summary of Invention. The reaction conditions could involve the use of a base such as triethylamine and in a suitable organic solvent such as acetonitrile. Compound 60 is either commercially available or may be synthesized by methods well known in the art.

Alternatively, compound 59 could be converted to the final compound of formula 63 by opening of the epoxide of formula 62 with the piperazine nitrogen of compound 59. The epoxide 62 is either commercially available or may be synthesized by methods well known in the art and the reaction may proceed in the presence of a suitable organic solvent such as isopropanol.

Alternatively, as shown in Scheme 10, compounds of formula 65 could be obtained by the condensation of com- Compound 64b is either commercially available or synthesized by methods well known in the art.

As shown in Scheme 11, compounds of general structure 7 may be generated by halogenation of compounds of general formula 12 using well known halogenating agents such as $Br_2$ in a suitable organic solvent such as acetic acid.

Scheme 11

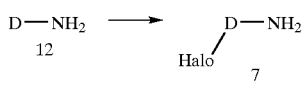

Alternatively as indicated in Scheme 12, compounds of formula 7 could be obtained by reduction of the corresponding nitro compound 66 using a reducing agent such as iron in the presence of $NH_4Cl$ and ethanol.

Scheme 12

Compounds of general formula 68 (or 12 in Scheme 1c when n=0 and $R^5$=H) may be synthesized as illustrated in Scheme 13 and 14 below.

Scheme 13

As illustrated in Scheme 13, the nitro compound 67 may be reduced to the amine 68 as previously described. Compound 67 is either commercially available or may be synthesized from compound 66 using a Suzuki reaction with compound 6 as previously described.

Scheme 14

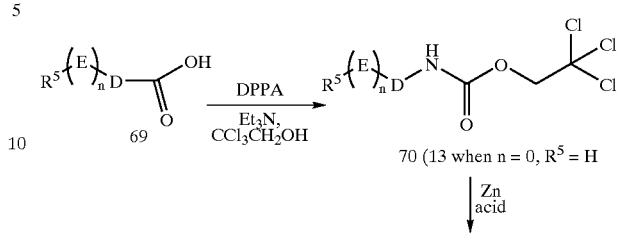

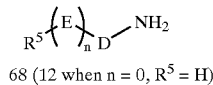

As outlined in Scheme 14, the amine 68 may be obtained via Curtius rearrangement of the acid 69 followed by removal of the troc group. The reaction may be carried out using reagents such as diphenylphosphonic azide and 2,2,2-trichloroethanol using a base such as triethylamine in a suitable organic solvent such as toluene. The troc group may be removed to afford the amine 68 as previously described.

In the case where X=—NH— and D=oxadiazole, compounds of the present invention may be prepared as shown in Scheme 15.

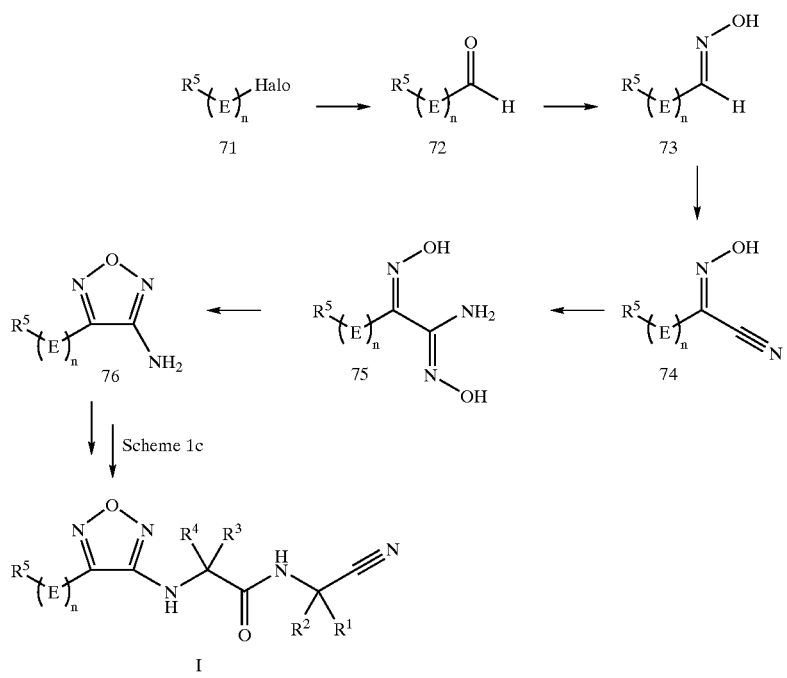

As illustrated in Scheme 15, a halogenated compound of formula 71 may be converted to the aldehyde 72 using conditions well known in the literature. An aldehyde of formula 72 may be converted into an oxime of formula 73 using reagents such as hydroxylamine hydrochloride in the presence of a base such as sodium carbonate. The formation of compound 74 may proceed by oxidation of 73 with NaOCl and subsequent treatment with KCN. Compound 74 may then be further treated with hydroxylamine hydrochloride to generate compound 75. The final ring closure to form the oxadiazole 76 may proceed with a base such as sodium hydroxide in a suitable organic solvent such as ethanol. The oxadiazole 76 may be elaborated to compounds of the present invention by methods described earlier (i.e. Scheme 1c). In the case where X=—NH— and D=isoxazole, compounds of the present invention may be prepared as shown in Scheme 16. An aldehyde of formula 72 may be converted into an oxime which may be chlorinated to compound 77. Compound 77 may be converted to a nitrile oxide by methods well known in the literature (i.e. treatment with a base). An appropriately substituted olefin 78 may be reacted with the nitrile oxide formed in situ to form a compound of formula 79 bearing an isoxazole ring. If the olefin contains a carboxylic ester substituent, ester hydrolysis followed by Curtius rearrangement in the presence of an appropriate alcohol will provide the carbamate-protected aminoisoxazole 80. In the case where this carbamate is troc, the aminoisoxazole 80 may be converted into compounds of the present invention by methods described earlier.

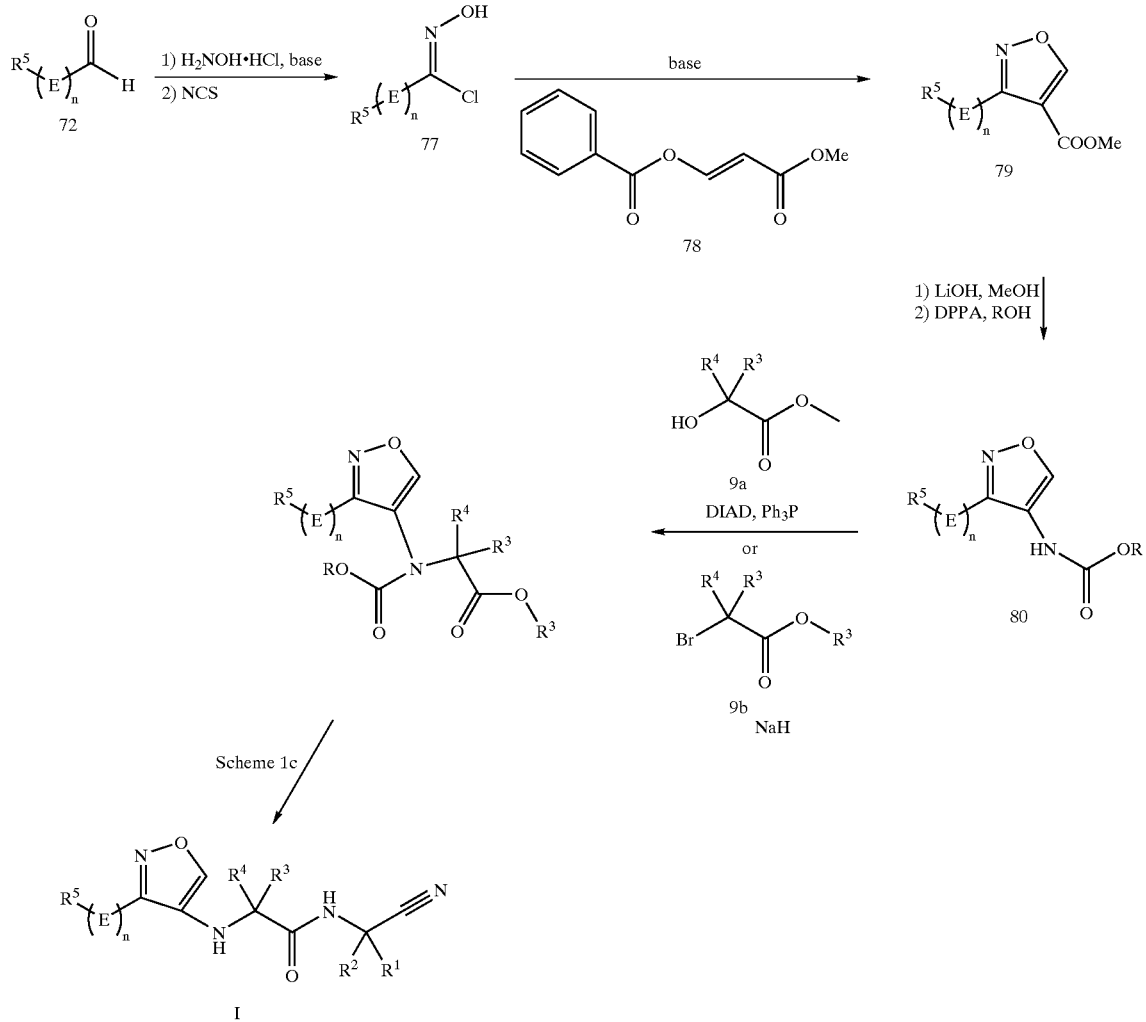

In the case where X=NH and D=isothiazole, compounds of the present invention may be prepared as shown in Scheme 17. Suitably substituted amido dithianes of formula 81 may be prepared by methods known in the literature. Oxidative cyclization in the presence of chlorine gas generates the N-substituted isothiazolinone 82. These may undergo rearrangement in the presence of an activating agent such as phosphorus oxychloride or methyl triflate followed by treatment with ammonia gas to provide the amino-substituted isothizaoles 83. Aromatic ring bromination then provides the bromo-substituted aminoisothiazole 84. This bromo-substituted aminoisothiazole may be converted into compounds of the present invention by methods described earlier.

Scheme 17

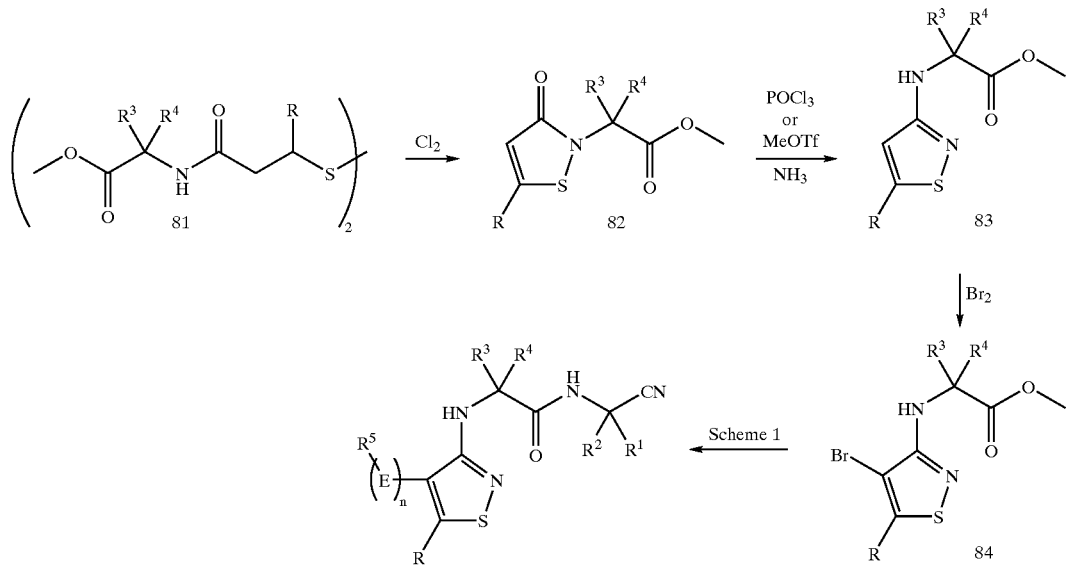

The following Examples describe the synthesis of selected compounds of the present invention. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Substituent numbering as shown in the schemes does not necessarily correlate to that used in the claims.

EXAMPLES

Example 1

Synthesis of (2S)-N-(Cyanomethyl)-4-Methyl-2-{[4'-(1-Piperazinyl)[1,1'-Biphenyl]-4-yl]Amino}Pentanamide To 1,4-dibromobenzene (16.1 g, 68.25 mmol), L-leucine (2.984 g, 22.75 mmol), potassium carbonate (4.71 g, 34.13 mmol), and copper iodide (650 mg, 3.41 mmol) was added dry DMA (N,N-dimethylacetamide, 100 mL). The reaction flask was thoroughly degassed with dry nitrogen and heated at 95° C. for 3 days. Water and hexane were added and the organic phase was separated and discarded (to remove excess 1,4-dibromobenzene). The pH of the aqueous phase was adjusted to 3 and the product was extracted with EtOAc (3×), dried on $Na_2SO_4$, concentrated in vacuo, and purified by flash chromatography over silica gel (EtOAc/Hex/AcOH, 3/7/1% then 4/6/1%) to afford (2S)-2-(4-bromoanilino)-4-methylpentanoic acid.

To (2S)-2-(4-bromoanilino)-4-methylpentanoic acid (5.80 g, 20.28 mmol), PyBOP (11.08 g, 21.29 mmol), and aminoacetonitrile hydrochloride (3.75 g, 40.56 mmol) in dry DMF (150 mL) under dry nitrogen at 0° C. was added triethylamine (8.8 mL, 62.87 mmol) dropwise and the reaction was warmed to rt and stirred overnight. Aqueous sat. $NaHCO_3$ was added and the product was extracted with ether (2×), dried over $Na_2SO_4$, concentrated in vacuo, and purified by flash chromatography over silica gel (EtOAc/Hex, 35/65 then 4/6) to afford (2S)-2-(4-bromoanilino)-N-(cyanomethyl)-4-methylpentanamide.

To a suspension of 1-(4-bromophenyl)-piperazine hydrochloride (103.15 g, 371.59 mmol) in MeCN (1.5 L) at 0° C. under dry nitrogen was added a catalytic amount of DMAP (4.54 g, 37.159 mmol) followed by triethylamine (155 mL, 1114.77 mmol) and di-tert-butyl dicarbonate (121.65 g, 557.385 mmol, dissolved in a minimum amount of MeCN) and the reaction was warmed to rt and stirred for 5.5 hours. The reaction mixture was filtered, EtOAc was added and the organic phase washed with aqueous 10% citric acid, water (2×), brine, dried on $MgSO_4$, and concentrated in vacuo to afford tert-butyl 4-(4-bromophenyl)-1-piperazinecarboxylate which was used as such in the next step.

To tert-butyl 4-(4-bromophenyl)-1-piperazinecarboxylate (118.30 g, 346.9 mmol) in dry THF/MePh (1/1, 1.5 L) at −78° C. under dry nitrogen was added n-BuLi (2.5 M, 160 mL, 398.9 mmol) dropwise and the reaction was stirred at −78° C. for 20 minutes. Triisopropyl borate (96.1 mL, 416.3 mmol) was added dropwise and the reaction was warmed to 0° C. and stirred for 2 hours. Aqueous sat. $NH_4Cl$ (400 mL), water (100 mL) and 1 equivalent of $H_3PO_4$ (20 ML) were added and the mixture stirred for 15 minutes and then concentrated to a volume of approximately 200 mL (at which stage the mixture became bluish and a precipitate formed). A dropping funnel was charged with heptane (800 mL) and the solvent was added to the reaction mixture with vigorous stirring over a period of one hour and the resulting suspension was stirred overnight. The suspension was filtered, washed with heptane (2×200 mL), and dried over the weekend in vacuo to afford 4-[4-(tert-butoxycarbonyl)-1-piperazinyl]phenylboronic acid.

To (2S)-2-(4-bromoanilino)-N-(cyanomethyl)-4-methylpentanamide (555 mg, 1.71 mmol), and 4-[4-(tert-butoxycarbonyl)-1-piperazinyl]phenylboronic acid (520 mg, 1.71 mmol) in DMF (20 mL) under dry nitrogen was added aqueous sodium carbonate (2 M, 2.55 mL, 5.13 mmol) followed by the catalyst $PdCl_2(dppf)$ (42 mg, 0.051 mmol). The reaction was heated to 105° C. for 0.75 hours and more $PdCl_2(dppf)$ (42 mg, 0.051 mmol) was added and the reaction mixture was heated for another 4–5 hours. Water was added and the product extracted with ether (2×), dried over $Na_2SO_4$, concentrated in vacuo, and purified by flash chromatography over silica gel (EtOAc/Hex, 4/6 then 1/1) to afford tert-butyl 4-{4'-[((1S)-1-{[(cyanomethyl)amino]carbonyl}-3-methylbutyl)amino][1,1'-biphenyl]-4-yl}-1-piperazinecarboxylate.

To tert-butyl 4-{4'-[((1S)-1-{[(cyanomethyl)amino]carbonyl}-3-methylbutyl)amino][1,1'-biphenyl]-4-yl}-1-piperazinecarboxylate (122 mg, 0.242 mmol) in dry TB (5 mL) under dry nitrogen was gradually added a total of 10 equivalents of $MeSO_3H$ (160 μL, 2.42 mmol) over a period of 5 days in portions of 1–2 equivalents at a time. Aqueous sat. $NaHCO_3$ was added carefully and the product was extracted with EtOAc (3×), dried over $Na_2SO_4$, concentrated in vacuo, and purified by flash chromatography over silica gel ($NH_4OH/MeOH/CH_2Cl_2$, 1.5/13.5/85) to afford (2S)-N-(cyanomethyl)-4-methyl-2-{[4'-(1-piperazinyl)[1,1'-biphenyl]-4-yl]amino}pentanamide. MS (+ESI): 406.9 $[M+1]^+$.

Example 2

Synthesis of N-(Cyanomethyl)-4-Methyl-2-({5-[4-(1-Piperazinyl)Phenyl]-2-Pyrimidinyl}Amino)Pentanamide To 2-amino-5-bromopyrimidine (3.12 g, 17.93 mmol) in dry DMF (60 mL) at 0° C. under dry nitrogen was added NaH (860 mg, 21.52 mmol) portionwise and the reaction was warmed to rt and stirred for 1 hour. The reaction was cooled again to 0° C. and methyl 2-bromo-4-methylpentanoate (4.7 g, 22.42 mmol, Bull. Chem. Soc. Jpn. 1989, 62, 2562) was added dropwise and the reaction was warmed to rt and stirred another 4 hours. Water was added, the aqueous phase neutralized with aq. 10 % HCl, and the product extracted with $Et_2O$ (2×), dried over $Na_2SO_4$, concentrated in vacuo, and purified by flash chromatography over silica gel (EtOAc/Hex, 2/8 then 3/7 then 4/6) to afford methyl 2-[(5-bromo-2-pyrimidinyl)amino]-4-methylpentanoate.

To methyl 2-[(5-bromo-2-pyrimidinyl)amino]-4-methylpentanoate (1.27 g, 4.2 mmol) in MeOH (50 mL) was added an aqueous solution of LiOH (2 M, 21 mL, 42 mmol) and the reaction was stirred for 5 hours. The reaction was neutralized with aqueous 10% HCl (pH of 6–7) and concentrated to a minimum volume in vacuo. Brine was added and the product was extracted with EtOAc (3×), dried on $Na_2SO_4$, concentrated in vacuo, and stripped with MePh (3×) to afford N-(5-bromo-2-pyrimidinyl)leucine which was used as such in the next step.

To the crude N-(5-bromo-2-pyrimidinyl)leucine (1.3 g, 4.2 mmol), PyBOP (2.62 g, 5.04 mmol), aminoacetonitrile hydrochloride (930 mg, 10.08 mmol) in dry DMF (50 mL) under dry nitrogen was added triethylamine (2.4 mL, 16.8 mmol) dropwise and the reaction was stirred overnight. Aqueous Sat. $NaHCO_3$ was added and the product extracted with $Et_2O$ (2×), dried on $Na_2SO_4$, concentrated in vacuo, and purified by flash chromatography over silica gel (EtOAc/Hex, 1/1) to afford 2-[(5-bromo-2-pyrimidinyl) amino]-N-(cyanomethyl)-4-methylpentanamide.

To 2-[(5-bromo-2-pyrimidinyl)amino]-N-(cyanomethyl)-4-methylpentanamide (123 mg, 0.377 mmol) and 4-[4-(tert-butoxycarbonyl)-1-piperazinyl]phenylboronic acid (140 mg, 0.453 mmol) in DMF (10 mL) under dry nitrogen was added aqueous sodium carbonate (2 M, 0.6 mL, 1.2 mmol) followed by the catalyst $PdCl_2(dppf)$ (15 mg, 0.0113 mmol). The reaction was heated to 90° C. for 0.5 hours and more $PdCl_2(dppf)$ (15 mg, 0.0113 mmol) was added and the reaction mixture was heated for another 5.5 hours. Water was added and the product extracted with ether (2×), dried over $Na_2SO_4$, concentrated in vacuo, and purified by flash chromatography over silica gel (EtOAc/Hex, 7/3) to afford tert-butyl 4-(4-{2-[(1-{[(cyanomethyl)amino]carbonyl}-3-methylbutyl)amino]-5-pyrimidinyl}phenyl)-1-piperazinecarboxylate.

To tert-butyl 4-(4-{2-[(1-{[(cyanomethyl)amino]carbonyl}-3-methylbutyl)amino]-5-pyrimidinyl}phenyl)-1-piperazinecarboxylate (108 mg, 0.213 mmol) in dry THF (5 mL) under dry nitrogen was gradually added a total of 9 equivalents of $MeSO_3H$ (total of 125 μL, 1.92 mmol) over a period of 3 days in portions of 1–2 equivalents at a time. Aqueous sat. $NaHCO_3$ was added carefully and the product extracted with EtOAc (3×), dried over $Na_2SO_4$, concentrated in vacuo, and purified by flash chromatography over silica gel ($NH_4OH/MeOH/CH_2Cl_2$, 1/9/90) to afford N-(cyanomethyl)-4-methyl-2-({5-[4-(1-piperazinyl)phenyl]-2-pyrimidinyl}amino)pentanamide. MS (–ESI): 406.4 $[M-1]^-$.

Example 3

Synthesis of (2S)-N-(Cyanomethyl)-4-Methyl-2-({[4'-(1-Piperazinyl)[1,1'-Biphenyl]-4-yl]Methyl}Amino)Pentanamide To L-leucine methyl ester hydrochloride (1.427 g, 7.855 mmol), 4-bromobenzaldehyde (1.451 g, 7.855 mmol), and $MgSO_4$ (0.1 g/mmol, 1 g) in $CH_2Cl_2$ (20 mL) was added triethylamine (840 μL, 8.25 mmol) dropwise and the reaction mixture was stirred overnight. The heterogeneous solution was filtered over celite, the filter cake washed several times with $CH_2Cl_2$ and the filtrate was concentrated in vacuo. The residue was dissolved in a minimal amount of MeOH and $NaBH_4$ (300 mg, 7.855 mmol) was added portionwise at 0° C. and the reaction mixture was stirred for 3.5 hours. The reaction was quenched with water and the product was extracted with EtOAc (2×), dried over $Na_2SO_4$, concentrated in vacuo, and purified by flash chromatography over silica gel (EtOAc/Hex, 2/8) to afford methyl (2S)-2-[(4-bromobenzyl)amino]-4-methylpentanoate.

To methyl (2S)-2-[(4-bromobenzyl)amino]-4-methylpentanoate (2.198 g, 7.0 mmol) in MeOH (30 mL) was added an aqueous solution of LiOH (2 M, 17.5 mL, 35 mmol) and the reaction was stirred overnight. The reaction was neutralized with aqueous 10% HCl (pH of 6–7) and the product crystallized out of solution and was filtered and dried in vacuo to afford (2S)-2-[(4-bromobenzyl)amino]-4-methylpentanoic acid.

To (2S)-2-[(4-bromobenzyl)amino]-4-methylpentanoic acid (1.343 g, 4.62 mmol), PyBOP (2.65 g, 5.08 mmol), aminoacetonitrile hydrochloride (940 mg, 10.16 mmol) in dry DMF (30 mL) under dry nitrogen was added triethylamine (2.2 mL, 15.71 mmol) dropwise and the reaction was stirred for 4 hours. Aqueous sat. $NaHCO_3$ was added and the product extracted with $Et_2O$ (2×), dried on $Na_2SO_4$, concentrated in vacuo, and purified by flash chromatography over silica gel (EtOAc/Hex, 4/6 then 1/1) to afford (2S)-2-[(4-bromobenzyl)amino]-N-(cyanomethyl)-4-methylpentanamide.

To (2S)-2-[(4-bromobenzyl)amino]-N-(cyanomethyl)-4-methylpentanamide (285 mg, 0.843 mmol) and 4-[4-(tert-butoxycarbonyl)-1-piperazinyl]phenylboronic acid (315 mg, 1.02 mmol) in DMF (10 mL) under dry nitrogen was added aqueous sodium carbonate (2 M, 1.3 mL, 2.53 mmol) followed by the catalyst PdCl$_2$(dppf) (25 mg, 0.026 mmol). The reaction was heated to 95° C. for 0.5 hours and more PdCl$_2$(dppf) (25 mg, 0.026 mmol) was added and the reaction mixture was heated overnight. Water was added and the product extracted with ether (2×), dried over Na$_2$SO$_4$, concentrated in vacuo, and purified by flash chromatography over silica gel (EtOAc/Hex, 4/6) to afford tert-butyl 4-(4'-{[((1S)-1-{[(cyanomethyl)amino]carbonyl}-3-methylbutyl)amino]methyl}[1,1'-biphenyl]-4-yl)-1-piperazinecarboxylate.

To tert-butyl 4-(4'-{[((1S)-1-{[(cyanomethyl)amino]carbonyl}-3-methylbutyl)amino]-methyl}[1,1'-biphenyl]-4-yl)-1-piperazinecarboxylate (85 mg, 0.164 mmol) in dry THF (5 mL) under dry nitrogen was gradually added a total of 8 equivalents of MeSO$_3$H (total of 85 μL, 1.31 mmol) over a period of 2 days in portions of 1–2 equivalents at a time. Aqueous sat. NaHCO$_3$ was added carefully and the product extracted with EtOAc (3×), dried over Na$_2$SO$_4$, concentrated in vacuo, and purified by flash chromatography over silica gel (NH$_4$OH/MeOH/CH$_2$Cl$_2$, 1/9/90) to afford (2S)-N-(cyanomethyl)-4-methyl-2-({[4'-(1-piperazinyl)[1,1'-biphenyl]-4-yl]methyl}amino)pentanamide. MS (+APCI): 420.3 [M+1]$^+$.

Example 4

Synthesis of N-(Cyanomethyl)-4-Methyl-2-{[4'-(1-Piperazinyl)[1,1'-Biphenyl]-3-yl]oxy}Pentanamide 3-Bromophenol (2.99 g, 17 mmoles) in a mixture of DMF (3 mL) and THF (15 mL) was treated with potassium tert-butoxide (1.85 g, 16.5 mmoles) and stirred for 30 minutes. Methyl 2-bromo-4-methylpentanoate (2.5 mL, 15.75 mmoles) was added in one portion and the reaction was stirred overnight. The reaction was diluted with diethyl ether, water and sat. aq. bicarbonate. The phases were separated and the organic phase was washed with 2 portions of 1.2 N hydrochloric acid and then brine. The organic phase was dried over anhydrous magnesium sulfate and concentrated under reduced pressure to afford a residue which was purified by flash chromatography to give methyl 2-(3-bromophenoxy)-4-methylpentanoate.

Methyl 2-(3-bromophenoxy)-4-methylpentanoate, in a mixture of water (42 mL), methanol (8 mL) and tetrahydrofuran (4 mL) was treated with lithium hydroxyde monohydrate (1.3 g, 31.6 mmoles) until disappearance of the starting material was observed by TLC. The reaction was diluted with 1.2 N hydrochloric acid until pH 1. The aqueous phase was extracted 3 times with dichloromethane. The organic phase was concentrated under reduced pressure to provide a residue that was used as such in the next reaction. To a solution of the resulting crude 2-(3-bromophenoxy)-4-methylpentanoic acid in DMF (30 mL) was added aminoacetonitrile hydrochloride (2.9 g, 31.5 mmoles) and HATU (6.3 g, 16.5 mmoles). After stirring for 1 minute, triethylamine (8.75 mL, 63 mmoles) was added in one portion. The reaction was stirred overnight, diluted with ethyl acetate and water. The organic phase was separated and washed twice with 1.2 N hydrochloric acid, brine and dried over magnesium sulfate. After concentration under reduced pressure, the solid 2-(3-bromophenoxy)-N-(cyanomethyl)-4-methylpentanamide obtained was sufficiently pure.

A cold (−78° C.) solution of 1-(4-bromophenyl)piperazine (6g, 21.6 mmoles) and triethylamine (7.5 mL, 54 mmoles) in dichloromethane (200 mL) and dimethylformamide (15 mL) was treated with dry solid carbon dioxide (24 g, 540 mmoles) and stirred for 30 minutes prior to the addition of triisopropyl trifluoromethanesulfonate (5.5 mL, 20.5 mmoles). The reaction was warmed to room temperature overnight. Water and dichloromethane were added and the phases were separated. The organic phase was washed with sat. aq. sodium bicarbonate, washed with 1.2 N hydrochloric acid, washed with a mixture of brine (98%) and sat. aq. sodium bicarbonate (2%), dried over magnesium sulfate and concentrated under reduced pressure to give triisopropylsilyl 4-(4-bromophenyl)-1-piperazinecarboxylate. The product was clean and used as such in the next step.

A solution of triisopropylsilyl 4-(4-bromophenyl)-1-piperazinecarboxylate (4.5 g, 10.2 mmoles) in toluene (17 mL) and tetrahydrofuran (17 mL) was degassed by bubbling nitrogen at room temperature via a fritted gas dispenser for 10 minutes and then cooled to −78° C. for the addition of butyllithium (4.9 mL as a 2.5 M solution in hexanes, 12.3 mmoles). The solution turned yellow and after 30 minutes, triisopropylborate (3 mL, 13.3 mmoles) was added and the solution was warmed to 0° C. over 2.5 h prior to quenching with sat. aq. ammonium chloride (22 mL). To the flask was added 0.825 mL of phosphoric acid (14.8 M, 12.3 mmoles). The solution was stirred for 30 minutes. The phases were separated and the organic phase was dried over sodium sulfate. Right after filtering off the drying agent, the organic phase was washed with wet tetrahydrofuran (approx 2% water). The solution was concentrated to approx 15 mL. While concentrating, three 0.5 mL-portions of water were added to prevent boroxine formation. At this point, hexane was added and the resulting precipitate was filtered to yield 4-(4-{[(triisopropylsilyl)oxy]carbonyl}-1-piperazinyl)phenylboronic acid.

To 2-(3-bromophenoxy)-N-(cyanomethyl)-4-methylpentanamide (1 g, 3.07 mmoles) in toluene (20 mL) was added 4-(4-{[(triisopropylsilyl)oxy]carbonyl}-1-piperazinyl)phenylboronic acid (1.25g, 3.07 mmoles) followed by solid potassium carbonate (0.85 g, 6.14 mmoles) and finally [1,1'-bis(diphenylphosphino)-ferrocene]dichloropalladium (II), complex with dichloromethane (1:1) (250 mg, 0.31 mmoles). The reaction was stirred overnight at 80° C. and cooled to room temperature prior to taking it up in ethylacetate. The organic phase was washed three times with 1.2 N hydrochloric acid, washed with brine, dried over magnesium sulfate and concentrated under reduced pressure. The residue was purified by chromatography (10% EtOAc, 90% Hexanes) to give triisopropylsilyl 4-[3'-(1-{[(cyanomethyl)amino]carbonyl}-3-methylbutoxy)[1,1'-biphenyl]-4-yl]-1-piperazinecarboxylate.

Triisopropylsilyl 4-[3'-(1-{[(cyanomethyl)amino]carbonyl}-3-methylbutoxy)[1,1'-biphenyl]-4-yl]-1-piperazinecarboxylate (365 mg, 0.6 mmoles) in 8 mL of tetrahydrofuran was treated with tetrabutylammonium fluoride (0.75 mL, 1 M in THF, 0.75 mmoles) at 0° C. until the disappearance of the starting material was observed by TLC. The reaction was diluted with diethyl ether, ethyl acetate, water and sat. aq. sodium bicarbonate. The phases were separated, the organic phase washed with brine and dried over sodium sulfate. After concentration under reduced pressure, the residue was purified by flash chromatography (1% sat. aqueous ammonium hydroxide, 9% methanol, 90% dichloromethane) to afford N-(cyanomethyl)-4-methyl-2-{[4'-(1-piperazinyl)[1,1'-biphenyl]-3-yl]oxy}pentanamide. MS (−ESI): 405.3 [M−1]$^−$.

Example 5

Synthesis of N-(Cyanomethyl)-4-Methyl-2-{[4'-(1-Piperazinyl)[1,1'-Biphenyl]-4-yl]Methoxy}Pentanamide 4-Bromobenzylalcohol (1.1 g, 5.9 mmoles) in 12 mL of DMF was treated with sodium hydride (260 mg, 60% oil dispersion, 6.5 mmoles) and stirred for 30 minutes. Methyl 2-bromo-4-methylpentanoate (1.1 mL, 6.8 mmoles) was added in one portion and the reaction was stirred overnight. The reaction was diluted with diethyl ether, ethyl acetate, water and sat. aq. bicarbonate. The phases were separated and the organic phase was washed with 2 portions of 1.2 N hydrochloric acid and then brine. The organic phase was dried over anhydrous sodium sulfate and concentrated under reduced pressure to yield a residue which was purified by flash chromatography to afford methyl 2-[(4-bromobenzyl)oxy]-4-methylpentanoate.

Methyl 2-[(4-bromobenzyl)oxy]-4-methylpentanoate in a mixture of water (3 mL), methanol (3 mL) and tetrahydrofuran (6 mL) was treated with lithium hydroxyde monohydrate (560 mg, 13.3 mmoles) until disappearance of the starting material was observed by TLC. The reaction was diluted with 1.2 N hydrochloric acid until pH 1. The aqueous phase was extracted 3 times with dichloromethane. The organic phase was concentrated under reduced pressure to afford 2-[(4-bromobenzyl)oxy]-4-methylpentanoic acid which was used as such in the next reaction.

To a solution of 2-[(4-bromobenzyl)oxy]4-methylpentanoic acid in DMF (15 mL) was added aminoacetonitrile hydrochloride (1.9 g, 20.6 mmoles) and HATU (5 g, 13.3 mmoles). After stirring for one minute, triethylamine (5.3 mL, 38.3 mmoles) was added in one portion. The reaction was stirred overnight, diluted with ethyl acetate and water. The organic phase was separated and washed twice with 1.2 N hydrochloric acid, brine and dried over magnesium sulfate. After concentration under reduced pressure, 2-[(4-bromobenzyl)oxy]-N-(cyanomethyl)-4-methylpentanamide was obtained.

To 2-[(4-bromobenzyl)oxy]-N-(cyanomethyl)-4-methylpentanamide (646 mg, 1.9 mmoles) in DMF (12.5 mL) was added 4-[4-(tert-butoxycarbonyl)-1-piperazinyl]phenylboronic acid (640 mg, 2.1 mmoles) followed by 2 M aqueous sodium carbonate (2.85 mL, 5.7 mmoles) and finally [1,1'-bis(diphenylphosphino)-ferrocene]dichloropalladium(II), complex with dichloromethane (1:1) (78 mg, 0.1 mmoles). The reaction was stirred overnight at 85° C. and cooled to room temperature prior to taking it up in ethylacetate. The organic phase was washed three times with 1.2 N hydrochloric acid, washed with brine, dried over magnesium sulfate and concentrated under reduced pressure. The residue was purified by chromatography (10% EtOAc, 90% Hexanes) to give tert-butyl 4-{4'-[(1-{[(cyanomethyl)amino]carbonyl}-3-methylbutoxy)-methyl][1,1 '-biphenyl]-4-yl}-1-piperazinecarboxylate.

A solution of tert-butyl 4-{4'-[(1-{[(cyanomethyl)amino]carbonyl}-3-methylbutoxy)methyl][1,1'-biphenyl]-4-yl}-1-piperazinecarboxylate (115 mg, 0.21 mmoles) in tetrahydrofuran (3.5 mL) was treated with methanesulfonic acid (30 µL, 0.4 mmoles). The same amount of acid was added 5 times at 1.5 hour intervals and stirred overnight. Acid addition was resumed and two more portions (30 µL, 0.4 mmoles) were added, with a 1.5 hour interval. The reaction was diluted with diethyl ether, ethylacetate, sat. aq. sodium bicarbonate. The phases were separated and the organic phase was dried over sodium sulfate and concentrated under reduced pressure. The product was chromatographed (1% sat. aq. ammonium hydroxyde, 9% methanol, 90% dichloromethane) to obtain 77 mg N-(cyanomethyl)-4-methyl-2-{[4'-(1-piperazinyl)[1,1'-biphenyl]-4-yl]methoxy}pentanamide, a yellowish solid.

MS (–APCI): 419.5 [M–1]$^-$.

Example 6

Synthesis of N-(Cyanomethyl)-4-Methyl-2-{[4'-(1-Piperazinyl)[1,1'-Biphenyl]-2-yl]Methyl}Pentanamide To N,N-diisopropylamine (2.6 mL, 18.4 mmol) in dry THF (40 mL) under dry nitrogen and at 0° C. was added n-BuLi (2.5 M, 7.35 mL, 18.3 mmol) dropwise and the reaction was stirred at rt for 20 min. The reaction mixture was again cooled to 0° C. and 3-(2-bromophenyl)-propionic acid (1.9 g, 8.29 mmol, dissolved in dry THF, 40 mL) was added dropwise via cannula and then warmed to rt and stirred for 15 min. The reaction mixture was again cooled to 0° C. and 1-iodo-2-methyl propane (1.5 mL, 13.26 mmol) was added dropwise. The reaction was then warmed to rt and stirred overnight. Aqueous 10% HCl was added carefully followed by brine and the product was extracted with EtOAc (3×), dried over $Na_2SO_4$, concentrated in vacuo, and purified by flash chromatography over silica gel (EtOAc/Hex/AcOH, 4/6/0.5%) to afford 2-(2-bromobenzyl)-4-methylpentanoic acid.

To 2-(2-bromobenzyl)-4-methylpentanoic acid (1.248 g, 4.38 mmol), PyBOP (3.12 g, 6.0 mmol), aminoacetonitrile hydrochloride (1.11 g, 12.0 mmol) in dry DMF (30 mL) under dry nitrogen was added triethylamine (1.9 mL, 18.53 mmol) dropwise and the reaction was stirred for 2.5 hours. Aqueous Sat. $NaHCO_3$ was added and the product, extracted with $Et_2O$ (2×), dried on $Na_2SO_4$, concentrated in vacuo, and purified by flash chromatography over silica gel (EtOAc/Hex, 3/7) to afford 2-(2-bromobenzyl)-N-(cyanomethyl)-4-methylpentanamide.

To 2-(2-bromobenzyl)-N-(cyanomethyl)-4-methylpentanamide (260 mg, 0.805 mmol) and 4-[4-(tert-butoxycarbonyl)-1-piperazinyl]phenylboronic acid (275 mg, 0.886 mmol) in DMF (10 mL) under dry nitrogen was added aqueous sodium carbonate (2 M, 1.2 mL, 2.42 mmol) followed by the catalyst $PdCl_2$(dppf) (25 mg, 0.025 mmol). The reaction was heated to 90° C. for 0.5 hours and more $PdCl_2$(dppf) (25 mg, 0.025 mmol) was added and the reaction mixture was heated for another 4 hours. Water was added and the product extracted with ether (2×), dried over $Na_2SO_4$, concentrated in vacuo, and purified by flash chromatography over silica gel (EtOAc/Hex, 35/65) to afford tert-butyl 4-[2'-(2-{[(cyanomethyl)amino]carbonyl}-4-methylpentyl)[1,1 '-biphenyl]-4-yl]-1-piperazinecarboxylate.

To tert-butyl 4-[2'-(2-{[(cyanomethyl)amino]carbonyl}-4-methylpentyl)[1,1'-biphenyl]-4-yl]-1-piperazinecarboxylate (407 mg, 0.808 mmol) in dry THF (10 mL) under dry nitrogen was gradually added a total of 6.5 equivalents of $MeSO_3H$ (total of 340 µL, 5.25 mmol) over a period of 3 days in portions of 1–2 equivalents at a time. Aqueous sat. $NaHCO_3$ was added carefully and the product extracted with EtOAc (3×), dried over $Na_2SO_4$, concentrated in vacuo, and purified by flash chromatography over silica gel ($NH_4$/OH/MeOH/$CH_2Cl_2$, 1/9/90) to afford N-(cyanomethyl)-4-methyl-2-{[4'-(1-piperazinyl)[1,1'-biphenyl]-2-yl]methyl}pentanamide.

MS (–ESI): 403.5 [M–1]$^-$.

Example 7

Synthesis of N-(Cyanomethyl)-2-[(5,5-Dimethyl-2-Oxo-4-Phenyl-2,5-Dihydro-3-Furanyl)Amino]-4-Methylpentanamide A mixture of 2-hydroxy-2-methylpropiophenone (2.0 g, 12.2 mmol), N-phthaloylglycine (2.7 g, 13.2 mmol), 1-cyclohexyl-3-(2-morpholinoethyl)carbodiimide metho-p-toluenesulfonate (10.3 g, 24.3 mmol) and DMAP (0.34 g, 2.8 mmol) was dissolved in dichloromethane (100 mL) and stirred 5 days at room temperature. The mixture was diluted with dichloromethane and washed with 1 M HCl (2×), saturated $NaHCO_3$ and brine, then filtered through cotton and concentrated to give 1,1-dimethyl-2-oxo-2-phenylethyl 2-(1,3-dioxo-1,3-dihydro-2H-isoindol-2-yl)acetate.

To a 0° C. suspension of unpurified 1,1-dimethyl-2-oxo-2-phenylethyl 2-(1,3-dioxo-1,3-dihydro-2H-isoindol-2-yl)acetate (4.4 g) in DMF (40 mL) was added a suspension of NaH (1.0 g of 60% dispersion, washed with hexanes) in DMF (10 mL). The mixture was stirred at 0° C. for 2 h, then diluted with EtOAc/ether (1:1) and 1 M HCl. The layers were separated and the organic phase was washed with water and brine, dried over $MgSO_4$ and concentrated. The residue was dissolved in toluene (50 mL), treated with PPTS (100 mg) and heated to reflux with a Dean-Stark trap for 3 h. The solution was cooled, diluted with EtOAc (100 mL) and washed with water and brine. The organic phase was dried over $MgSO_4$ and concentrated. Purification by flash chromatography (30–50% EtOAc/hexanes) provided 2-(5,5-dimethyl-2-oxo-4-phenyl-2,5-dihydro-3-furanyl)-1H-isoindole-1,3(2H)-dione, and 3-amino-5,5-dimethyl-4-phenyl-2(5H)-furanone.

To a 0° C. solution of 2-(5,5-dimethyl-2-oxo4-phenyl-2,5-dihydro-3-furanyl)-1H-isoindole-1,3(2H)-dione (0.90 g, 2.7 mmol) in THF (40 mL) and MeOH (30 mL) was added hydrazine hydrate (1 mL). The mixture was stirred overnight then diluted with EtOAc and washed with saturated $NH_4Cl$. The organic phase was concentrated, then dissolved in dichloromethane, washed with brine, filtered through cotton and concentrated. This material was combined with the 0.29 g from the previous step and purified by flash chromatography (25% EtOAc/hexanes) to provide 3-amino-5,5-dimethyl-4-phenyl-2(5H)-furanone.

A mixture of 3-amino-5,5-dimethyl-4-phenyl-2(5H)-furanone (175 mg, 0.86 mmol), methyl 2-bromo-4-methylpentanoate (360 mg, 1.73 mmol) and cesium carbonate (310 mg, 0.95 mmol) in DMF (4 mL) was heated to 130° C. for 18 h. The mixture was cooled, diluted with EtOAc and washed with water (2×) and brine, then dried over $MgSO_4$ and concentrated. Purification by flash chromatography (20% EtOAc/hexanes) provided methyl 2-[(5,5-dimethyl-2-oxo-4-phenyl-2,5-dihydro-3-furanyl)amino]-4-methylpentanoate.

To a solution of methyl 2-[(5,5-dimethyl-2-oxo-4-phenyl-2,5-dihydro-3-furanyl)amino]-4-methylpentanoate (64 mg, 0.19 mmol) in MeOH (3 mL) was added 1 M LiOH (1 mL). The solution was stirred for 22 h, then partitioned between ethyl acetate and 1 M HCl. The organic phase was washed with brine, dried over $MgSO_4$ and concentrated. The resulting acid was coupled with aminoacetonitrile hydrochloride under the conditions described previously (HATU, $Et_3N$, DMF) and purified by flash chromatography to give N-(cyanomethyl)-2-[(5,5-dimethyl-2-oxo4-phenyl-2,5-dihydro-3-furanyl)amino]-4-methylpentanamide.

MS (+APCI) m/z 356 (M+1, 5), 312(15), 272(100), 226 (50).

Example 8

Synthesis of N-(Cyanomethyl)-4-Methyl2-[(5-Phenyl-4H-1,2,4-Triazol-3-yl)Sulfanyl]Pentanamide 5-Phenyl-4H-1,2,4-triazole-3-thiol (296 mg, 1.67 mmoles) in 5 mL of DMF was treated with sodium hydride (67 mg, 60% oil dispersion, 1.76 mmoles) and stirred for 30 minutes. Methyl 2-bromo-4-methylpentanoate (275 μL, 1.67 mmoles) was added in one portion and the reaction was stirred overnight. The reaction was diluted with diethyl ether, water and sat. aq. bicarbonate. The phases were separated and the organic phase was washed with 2 portions of 1.2 N hydrochloric acid and then brine. The organic phase was dried over anhydrous sodium sulfate and concentrated under reduced pressure to afford a residue which was purified by flash chromatography to give methyl 4-methyl-2-[(5-phenyl-4H-1,2,4-triazol-3-yl)sulfanyl]pentanoate.

Methyl 4-methyl-2-[(5-phenyl-4H-1,2,4-triazol-3-yl)sulfanyl]pentanoate (473 mg, 1.54 mmoles) in a mixture of water (2 mL), methanol (2 mL) and tetrahydrofuran (4 mL) was treated with lithium hydroxyde monohydrate (193 mg, 4.6 mmoles) until disappearance of the starting material was observed by TLC. The reaction was diluted with 1.2 N hydrochloric acid until pH 1. The aqueous phase was extracted 3 times with dichloromethane. The organic phase was concentrated under reduced pressure to yield a crude residue of 4-methyl-2-[(5-phenyl-4H-1,2,4-triazol-3-yl)sulfanyl]pentanoic acid which was used as such in the next reaction.

To a solution of the crude 4-methyl-2-[(5-phenyl-4H-1,2,4-triazol-3-yl)sulfanyl]pentanoic acid in DMF (10 mL) was added aminoacetonitrile hydrochloride (427 mg, 4.62 mmoles) and HATU (1.76 g, 4.62 mmoles). After stirring for 30 seconds, triethylamine (1.3 mL, 9.24 mmoles) was added in one portion. The reaction was stirred overnight, diluted with ethyl acetate and water. The organic phase was separated and washed twice with 1.2 N hydrochloric acid, brine and dried over magnesium sulfate. After concentration under reduced pressure, N-(cyanomethyl)-4-methyl-2-[(5-phenyl-4H-1,2,4-triazol-3-yl)sulfanyl]pentanamide was obtained. MS (−APCI): 328.2 $[M-1]^-$.

Example 9

Synthesis of N-(Cyanomethyl)-1-{[4'-(1-Piperazinyl)[1,1'-Biphenyl]-2-yl]Sulfanyl}Cyclohexanecarboxamide To a solution of 715 mg (3.2 mmol) of methyl 1-bromocyclohexane-1-carboxylate (J. Med. Chem. 1970, 13, 317) in MeOH (5 mL) was added diisopropylethylamine (0.9 mL, 5.2 mmol) and 2-bromobenzenethiol (0.55 mL, 4.7 mmol). The solution was heated to 65° C. under nitrogen for 2 h, then cooled and partitioned between ethyl acetate and 1 M HCl. The organic phase was washed twice with 1 M NaOH and brine, then dried over $MgSO_4$ and concentrated. Purification by flash chromatography (10% EtOAc/hexanes) gave methyl 1-[(2-bromophenyl)sulfanyl]cyclohexanecarboxylate.

To a solution of methyl 1-[(2-bromophenyl)sulfanyl]cyclohexanecarboxylate (89 mg, in MeOH (3 mL) was added 1 M NaOH (1 mL). The mixture was stirred at room temperature for 2 days, then at 65° C. for 6 h. The mixture was then concentrated and the residue was partitioned between ethyl acetate and 1 M HCl. The organic phase was washed with brine, dried over MgSO₄ and concentrated to give 1-[(2-bromophenyl)sulfanyl]cyclohexanecarboxylic acid.

To a mixture of 1-[(2bromophenyl)sulfanyl]cyclohexanecarboxylic acid (77 mg, 0.24 mmol), HATU (99 mg, 0.26 mmol) and aminoacetonitrile hydrochloride (33 mg, 0.35 mmol) in DMF (3 mL) was added Et₃N (0.1 mL, 0.72 mmol). The mixture was stirred overnight, then partitioned between ethyl acetate and 1 M HCl. The organic phase was washed with water, 1 M NaOH and brine, then dried over MgSO₄ and concentrated to give 1-[(2-bromophenyl)sulfanyl]-N-(cyanomethyl)cyclohexanecarboxamide.

To a mixture of 4-(4-{[(triisopropylsilyl)oxy]carbonyl}-1-piperazinyl)phenylboronic acid (114 mg, 0.28 mmol), 1-[(2-bromophenyl)sulfanyl]-N-(cyanomethyl)cyclohexanecarboxamide (78 mg, 0.22 mmol), and milled K₂CO₃ (54 mg, 0.39 mmol) was added toluene (5 mL). A solution of Pd₂(dba)₃(14 mg, 0.015 mmol) and PPh₃ (28 mg, 0.11 mmol) in 1 mL toluene was added, and the mixture was heated overnight at 100° C. under nitrogen. The mixture was cooled and concentrated. Purification by flash chromatography (10% ethyl acetate/dichloromethane) provided triisopropylsilyl 4-{2'-[(1-{[(cyanomethyl)amino]carbonyl}cyclohexyl)sulfanyl][1,1'-biphenyl]-4-yl})-1-piperazinecarboxylate.

To a 0° C. solution of triisopropylsilyl 4-{2'-[(1-{[(cyanomethyl)amino]carbonyl}-cyclohexyl)sulfanyl][1,1'-biphenyl]-4yl}-1-piperazinecarboxylate (35 mg, 0.055 mmol) in THF (8 mL) was added TBAF (1 M in THF, 0.08 mL). The solution was stirred at 0° C. for 20 min, then partitioned between EtOAc and saturated aq. NaHCO₃. The organic phase was washed with water and brine, then dried over MgSO₄ and concentrated and placed under vacuum for 6 h to give N-(cyanomethyl)-1-{[4'-(1-piperazinyl)[1,1 '-biphenyl]-2-yl]sulfanyl}cyclohexanecarboxamide. MS (+APCI) m/z 435 (M+1, 40), 351 (100), 318 (45).

Example 10

Synthesis of N¹-(Cyanomethyl)-N²-[3-(4-Piperazin-1-ylphenyl)Isoxazol-4-yl]Leucinamide To a -78° C. solution of 1-(4-bromophenyl)-4-(tert-butoxycarbonyl)piperazine (9.98 g, 29.2 mmol, prepared as described in Example 1) in TI (70 mL) and toluene (70 mL) was added nBuLi (1.6 M in hexanes, 19 mL, 30.4 mmol) at a rate to maintain an internal temperature below -65° C. The resulting solution was stirred 15 min, then treated with DMF (5 mL). The mixture was stirred 30 min at -78° C., then allowed to warm to 0° C., quenched with saturated ammonium chloride and extracted with ethyl acetate. The organic phase was washed with brine, dried over MgSO₄ and concentrated. The crude material was crystalized from dichloromethane/ether/hexanes to give 4-[4-(tert-butoxycarbonyl)-1-piperazinyl]benzaldehyde. The filtrates were purified by flash chromatography (30% ethyl acetate/hexanes to 60% ethyl acetate/hexanes) to provide an additional 2.16 g of the desired product.

To a suspension of 4-[4-(tert-butoxycarbonyl)-1-piperazinyl]benzaldehyde (7.62 g, 26.2 mmol) and potassium carbonate (2.0 g, 14.5 mmol) in ethanol (100 mL) was added a saturated aqueous solution of hydroxylamine hydrochloride (2.78 g, 40 mmol). The resulting suspension was stirred at 50° C. overnight. The solid was filtered and the filtrate was concentrated by half. Water (50 mL) was added and the slurry was filtered to give 4-[4-(tert-butoxycarbonyl)-1-piperazinyl]benzoxime.

To a suspension of N-chlorosuccinimide (0.49 g, 3.7 mmol) in chloroform (15 mL) was added two drops of pyridine followed by 4-[4-(tert-butoxycarbonyl)-1-piperazinyl] benzoxime (1.03 g, 3.45 mmol). The mixture was stirred for 1 h, at which time an additional portion of N-chlorosuccinimide (0.18 g, 1.3 mmol) was added. The mixture was stirred an additional hour, then methyl 3-(p-nitrobenzoyloxy)acrylate (1.0 g, 4 mmol, see J. Heterocylic Chem 2000, 37, 75) was added in a single portion. Triethylamine (1.25 mL, 9 mmol) was added dropwise, and the mixture was stirred 3 h at room temperature. The crude reaction was diluted with dichloromethane and washed sequentially with water, pH 3.5 phosphate buffer, and 1 M NaOH. Purification by flash chromatography (35% to 70% ethyl acetate/hexanes) provided 538 mg of methyl 3-(4-[4-(tert-butoxycarbonyl)piperazin-1-yl]phenyl)isoxazole-4-carboxylate.

This material was dissolved in methanol, treated with 1 M LiOH and stirred overnight. The resulting solution was concentrated and partitioned between ethyl acetate and pH 3.5 phosphate buffer. The organic phase was washed with brine and dried over MgSO₄ to give 3-(4-[4-(tert-butoxycarbonyl)piperazin-1-yl]phenyl)isoxazole-4-carboxylic acid.

To a suspension of 3-(4-piperazin-1-ylphenyl)isoxazole-4-carboxylic acid (2.24 g, 6.0 mmol) in toluene (80 mL), was added triethylamine (0.85 mL, 6.1 mmol) followed by diphenylphosphoryl azide (1.45 mL, 6.7 mmol). The resulting solution was warmed to 50° C. for 1 h, then trichloroethanol (2.5 mL, 26 mmol) was added. The solution was heated to 100° C. for 6 h and then cooled and partitioned between ether and water. The organic phase was washed with brine and dried over MgSO₄. Purification by flash chromatography (5% to 10% ethyl acetate/dichloromethane) provided 2.23 g of 2,2,2-trichloroethyl 3-(4-[4-(tert-butoxycarbonyl)piperazin-1-yl]phenyl)isoxazol-4-ylcarbamate.

To a room temperature solution of 2,2,2-trichloroethyl 3-(4-piperazin-1-ylphenyl)isoxazol-4-ylcarbamate (1.63 g, 3.13 mmol) in DMF (20 mL) was added a suspension of sodium hydride (0.13 g of 60% dispersion washed with hexanes, 3.25 mmol) in DMF. The mixture was stirred 20 min, then methyl 2-bromo-4-methyl pentanoate (1.5 g, 7.2 mmol) was added and the solution stirred overnight. The reaction mixture was poured into water and extracted with 1:1 ether/ethyl acetate. The organic phase was washed with water and brine and concentrated. Purification by flash chromatography (30% to 60% ethyl acetate/hexanes) afforded 1.01 g of methyl N-(3-{4-[4-(tert-butoxycarbonyl)piperazin-1-yl]phenyl}isoxazol-4-yl)-N-[(2,2,2-trichloroethoxy)carbonyl]leucinate.

This reaction could also be carried out using then methyl (R)-2-bromo-4-methyl pentanoate (Syn Comm 1992, 22, 2187) to provide methyl N-(3-{4-[4-(tert-butoxycarbonyl)piperazin-1-yl]phenyl}isoxazol-4-yl)-N-[(2,2,2-trichloroethoxy)carbonyl]-(S)-leucinate.

To a solution of methyl N-(3-{4-[4-(tert-butoxycarbonyl)piperazin-1-yl]phenyl}isoxazol-4-yl)-N-[(2,2,2-trichloroethoxy)carbonyl]leucinate (1.0 g, 1.55 mmol) in THF (20 mL) was added acetic acid (10 mL) and zinc dust (2.8 g, 42.8 mmol). The mixture was sonicated for 1 min, then stirred 1.5 h at room temperature. The solids were filtered through celite and the filtrate was co-evaporated with heptane. The residue was dissolved in ethyl acetate and washed with aqueous NaHCO₃ and brine and concentrated. The residue was dissolved in methanol (25 mL) and 2 M LiOH (5 mL) was added. The mixture was stirred overnight at room temperature, then diluted with ethyl acetate and washed with pH 3 phosphate buffer. The organic phase was washed with brine and dried over MgSO$_4$, and concentrated to give 710 mg of N-(3-{4-[4-(tert-butoxycarbonyl)piperazin-1-yl]phenyl}isoxazol-4-yl)leucine.

To a 0° C. solution of N-(3-{4-[4-(tert-butoxycarbonyl)piperazin-1-yl]phenyl}isoxazol-4-yl)leucine (46 mg, 0.10 mmol), aminoacetonitrile hydrochloride (21 mg, 0.23 mmol) and HATU. (140 mg, 0.36 mmol) in DMF (3 mL) was added triethylamine (0.06 mL, 0.43 mmol). The solution was stirred 1 h, then partitioned between ether and pH 3.5 phosphate buffer. The organic phase was washed with brine and concentrated. Purification by flash chromatography (40% to 60% ethyl acetate/hexanes) gave 15.5 mg of $N^1$-(cyanomethyl)-$N^2$-[3-(4-[4-(tert-butoxycarbonyl)piperazin-1-yl]phenyl)isoxazol-4-yl]leucinamide.

To a room temperature solution of $N^1$-(cyanomethyl)-$N^2$-[3-(4-[4-(tert-butoxycarbonyl)piperazin-1-yl]phenyl)isoxazol-4-yl]leucinamide (15.5 mg, 0.031 mmol) in THF (2 mL) was added 8 equivalents of methanesulfonic acid (10% solution in dichloromethane) over 28 h. The reaction mixture was quenched with aqueous NaHCO$_3$ solution and extracted with dichloromethane (3×). The organic phase was filtered through cotton and evaporated. Purification by flash chromatography (2% to 15% methanol/dichloromethane+0.5% ammonium hydroxide) gave 3.8 mg of $N^1$-(cyanomethyl)-$N^2$-[3-(4-piperazin-1-ylphenyl)isoxazol-4-yl]leucinamide. MS (+ESI): 397.4 [M+1]$^+$.

Example 11

Synthesis of $N^1$-(Cyanomethyl)-$N^2$-(1-Phenyl-1H-Tetraazol-5-yl)-L-Leucinamide A suspension of 5-chloro-1-phenyl-1H-tetrazole (2.80 g, 15.5 mmol), L-leucine (3.36 g, 25.6 mmol) and potassium carbonate (6.43 g, 46.5 mmol) in isopropanol (20 mL) was heated to reflux for 3 h. The mixture was cooled and partitioned between ethyl acetate and 1 M HCl. The organic phase was washed with brine and concentrated. Purification by flash chromatography on silicic acid (50% ethyl acetate/hexanes) provided 1.57 g of N-(1-phenyl-1H-tetraazol-5-yl)-L-leucine.

To a solution of N-(1-phenyl-1H-tetraazol-5-yl)-L-leucine (100 mg, 0.36 mmol), aminoacetonitrile hydrochloride (62 mg, 0.68 mmol) and PyBOP (230 mg, 0.44 mmol) in DMF (3 mL) was added triethylamine (0.2 mL, 1.4 mmol). The solution was stirred 36 h, then partitioned between ethyl acetate and pH 3 phosphate buffer. The organic phase was washed with brine and concentrated. Purification by flash chromatography (60% to 90% ethyl acetate/hexanes) gave 62 mg of $N^1$-(cyanomethyl)-$N^2$-(1-phenyl-1H-tetraazol-5-yl)-L-leucinamide. MS (+APCI): 313.9 [M+1]$^+$.

Example 12

Synthesis of $N^1$-(Cyanomethyl)-$N^2$-(4-{4-[2-(Dimethylamino)Ethyl]Phenyl}Thien-3-yl)-L-Leucinamide To a suspension of 4-bromophenylacetic acid (2.0 g, 9.3 mmol) and PyBOP (4.8 g, 9.3 mmol) in DMF (15 mL) was added dimethylamine (2 M solution in THF, 12 mL, 24 mmol). The solution was stirred overnight, then diluted with ether and washed with 1 M HCl, saturated aqueous NaHCO$_3$ and brine to give 1.15 g 2-(4-bromophenyl)-N,N-dimethylacetamide.

To a suspension of LiAlH$_4$ in ether (5 mL) was added a solution of 2-(4-bromophenyl)-N,N-dimethylacetamide (1.1 g, 4.5 mmol) in 5:1 ether/THF (12 mL), giving a small exotherm. The mixture was stirred at room temperature for 3 h, refluxed overnight then cooled to 0° C. Water (0.5 mL) was added dropwise and the mixture stirred vigourously for 3 h, then poured into 1 M NaOH and extracted with ether. The organic phase was washed with brine and dried over MgSO$_4$. Purification by flash chromatography (4% to 8% MeOH/dichloromethane+0.5% ammonium hydroxide) provided 132 mg of 2-(4-bromophenyl)-N,N-dimethylethanamine.

To a −78° C. solution of 2-(4-bromophenyl)-N,N-dimethylethanamine (132 mg, 0.58 mmol) in THF (4 mL) was added nBuLi (1.5 M in hexanes, 0.41 mL, 0.61 mmol). The solution was stirred for 10 min, then treated with triisopropyl borate (0.17 mL, 0.73 mmol). The reaction was stirred 5 min at −78° C., then warmed to room temperature and quenched with methanol. The reaction was concentrated, and the residue was evaporated from MeOH (4×) to give lithium trimethyl-4-[2-(dimethylamino)ethyl]phenylborate.

A mixture of the total sample of crude lithium trimethyl-4-[2-(dimethylamino)ethyl]phenylborate, PdCl$_2$(dppf) (11 mg, 0.013 mmol) and $N^2$-(4-bromothien-3-yl)-$N^1$-(cyanomethyl)-L-leucinamide (0.24 mmol, prepared by the method given in example 1, using 3,4-dibromothiophene as the starting material) in DMF (2 mL) was heated to 80° C. 2 M Sodium carbonate (0.5 mL, 1 mmol) was added and the reaction mixture was stirred at 100° C. for 2 h and then cooled and partitioned between aqueous NaHCO$_3$ and ethyl acetate. The organic phase was washed with brine, dried over MgSO$_4$ and evaporated. Purification by flash chromatography (4% to 10% MeOH/dichloromethane+0.5% ammonium hydroxide) provided 58 mg of $N^1$-(cyanomethyl)-$N^2$-(4-{4-[2-(dimethylamino)ethyl]phenyl}thien-3-yl)-L-leucinamide. $^1$H NMR (500 MHz, d$_6$-acetone) δ 8.2 (br, 1H), 7.43 (d, 2H), 7.31 (d, 2H), 7.23 (s, 1H), 7.22 (s, 1H), 6.06 (br, 1H), 4.20 (m, 2H), 3.82, (m, 1H), 2.78 (m, 2H), 2.52 (m, 2H), 2.21 (s, 6H), 1.75 (m, 1H), 1.64 (m, 2H), 0.91 (d, 3H), 0.88 (d, 3H).

Example 13

Synthesis of $N^1$-(Cyanomethyl)-$N^2$-[4-(4-Piperazin-1-ylphenyl)Isothiazol-3-yl]-L-Leucinamide To a 10° C. solution of L-leucine (126.4 g, 963 mmol) in 10 N NaOH (97 mL) and water (200 mL) was added simultaneously from two dropping funnels over 1 h 3,3'-dithiodipropionyl dichloride (117 g, 475 mmol, see J. Heterocyclic Chem. 1971, 8, 571) and 10 N NaOH (100 mL), while maintaining the internal temperature at <20° C. with an ice-bath. The resulting liquid was filtered to remove a precipitate, and the filtrate was cooled in an icebath. Concentrated HCl (90 mL) was added dropwise, giving a thick slurry which separated to give a gum. The aqueous phase was decanted and the gum was dissolved in MeOH and evaporated 4× from toluene. The residue was dissolved in MeOH (1L), treated with acetyl chloride (5 mL) and heated to reflux for 4 h. The mixture was cooled and concentrated to give an oil which was dissolved in ethyl acetate and dried over MgSO$_4$. Evaporation of the solvent provided 197 g of N,N'-bis-((1S)-1-carbomethoxy-3-methylbutyl)-3,3'dithiodipropionamide.

To a 80° C. solution of N,N'-bis-(1-(S)-carbomethoxy-3-methylbutyl)-3,3'dithiodipropionamide (104 g, 424 mmol) in toluene (1 L), was added a stream of chlorine gas (194 g, 1.47 mol) over 15 h. The solution was cooled and washed with water (2×1 L), and brine and dried over MgSO$_4$. Purification by flash chromatography (50% ethyl acetate/hexanes) provided methyl (2S)-4-methyl-2-(3-oxoisothiazol-2(3H)-yl)pentanoate.

A solution of methyl (2S)-4-methyl-2-(3-oxoisothiazol-2(3H)-yl)pentanoate (0.98 g, 4.27 mmol) in POCl$_3$ (3 mL) was stirred for 2 h at room temperature. The mixture was diluted with ether and decanted (2×). The residue was dissolved in acetonitrile, cooled to 0° C. and treated with a stream of NH3 gas for 5 min. The resulting precipitate was filtered and the filtrate concentrated to give an oil. This oil was dissolved in dichloromethane, washed with saturated aqueous NaHCO$_3$ and brine, filtered through cotton and evaporated. Purification by flash chromatography (25% ethyl acetate/hexanes) provided 160 mg of methyl N-isothiazol-3-yl-L-leucinate.

To a solution of methyl N-isothiazol-3-yl-L-leucinate (160 mg, 0.70 mmol) in dichloromethane (3 mL) and acetic acid (0.5 mL) was added bromine (0.04 mL, 0.78 mmol). The solution was stirred for 45 min, then diluted with dichloromethane and washed with saturated aqueous NaHCO$_3$ and brine, filtered through cotton and evaporated to give 220 mg of methyl N-(4-bromoisothiazol-3-yl)-L-leucinate.

Ester hydrolysis and coupling with aminoacetonitrile as described in example 4 provided N$^2$-(4-bromoisothiazol-3-yl)-N$^1$-(cyanomethyl)-L-leucinamide. N$^2$-(4-bromoisothiazol-3-yl)-N$^1$-(cyanomethyl)-L-leucinamide was then treated with 4-[4-(tert-butoxycarbonyl)-1-piperazinyl]phenylboronic acid (prepared as described in Example 1) as described in Example 1 to afford, after BOC removal with methanesulfonic acid as described in Example 10, N$^1$-(cyanomethyl)-N$^2$-[4-(4-piperazin-1-ylphenyl)isothiazol-3-yl]-L-leucinamide. MS (+ESI): 413.2 [M+1]$^+$.

Example 14

Synthesis of N$^1$-(Cyanomethyl)-N$^2$-[4-(4-Piperazin-1-ylphenyl)Isothiazol-5-yl]Leucinamide Diphenylphosphonic azide (0.88mL, 4.0 mmol) was added dropwise to a mixture of isothiazole-5-carboxylic acid (500 mg, 3.90 mmol) and triethylamine (0.57 mL, 4.1 mmol) in toluene (10 mL) at rt and the resulting turbid, yellow solution was heated at 60° C. for 1 h. 2,2,2-Trichloroethanol (0.56 mL, 5.8 mmol) was introduced and the temperature was raised to 100° C. for an additional 3 h. The mixture was then cooled to rt, poured into water, extracted with ethyl acetate (3×) and the combined organics were washed with saturated sodium chloride aqueous solution and dried (MgSO$_4$). Concentration in vacuo and flash chromatography of the residue on silica gel eluting with a mixture of ethyl acetate and hexanes (1:3) provided 553 mg of 2,2,2-trichloroethylisothiazol-5-ylcarbamate as a faint yellow powder.

A solution of 2,2,2-trichloroethylisothiazol-5-ylcarbamate (253 mg, 0.918 mmol), triphenylphosphine (266 mg, 1.01 mmol) and methyl 2-hydroxy-4-methylpentanoate (151 mg, 1.03 mmol) in N,N-dimethylformamide (2.0 mL) at 0° C. was treated dropwise with diisopropylazodicarboxylate (200 µL, 1.02 mmol) and stirred at rt for 5 h. The mixture was then poured into water and extracted with a 1:1 mixture of ether and ethyl acetate (3×). The combined organics were washed with water and saturated sodium chloride solution, dried (Na$_2$SO$_4$) and concentrated. Flash chromatography of the residue on silica gel eluting with a mixture of ethyl acetate and, hexanes (1:3) gave 260 mg of methyl N-isothiazol-5-yl-N-[(2,2,2-trichloroethoxy)carbonyl]leucinate as a faint-yellow oil.

Bromine (85 µL, 1.7 mmol) was added to a solution of methyl N-isothiazol-5-yl-N-[(2,2,2-trichloroethoxy)carbonyl]leucinate (150 mg, 0.370 mmol) in dichloromethane (2.0 mL) over powdered potassium bicarbonate (370 mg, 3.7 mmol) with rapid stirring at rt for 5 h. Excess bromine was quenched by the addition of 1 M aqueous NaHSO$_3$ solution and the mixture was partitioned between water and ether. The layers were separated and the aqueous phase was extracted with additional ether (2×). The extracts were combined, dried (Na$_2$SO$_4$) and concentrated to give 172 mg of methyl N-(4-bromoisothiazol-5-yl)-N-[(2,2,2-trichloroethoxy)carbonyl]leucinate as a yellow oil.

A 1.0 M aqueous solution of KH$_2$PO$_4$ (1.8 mL) was added dropwise over several minutes to zinc dust (1.13 g, 17.8 mmol) and methyl N-(4-bromoisothiazol-5-yl)-N-[(2,2,2-trichloroethoxy)carbonyl]leucinate (172 mg, 0.356 mmol) in THF (3.2 mL) with rapid stirring at rt for 30 min. The slurry was diluted with ethyl acetate and filtered (Celite), and the filtrate was washed with water, then saturated sodium chloride solution and dried (Na$_2$SO$_4$). Solvent removal in vacuo afforded 180 mg of methyl N-(4-bromoisothiazol-5-yl)leucinate as a yellow oil.

A solution composed of methyl N-(4-bromoisothiazol-5-yl)leucinate (98 mg, 0.32 mmol) in methanol (1.5 mL) at 0° C. was treated with a 2.0 M solution of lithium hydroxide (1.0 mL, 2.0 mmol). The mixture was stirred rapidly at rt for 6 h and then recooled to 0° C. prior to acidification to pH 5.5with 2.0 M hydrochloric acid in water. The reaction vessel contents were poured into water, extracted with ethyl acetate (3×) and the combined organics were washed with saturated sodium chloride solution and dried (Na$_2$SO$_4$). Concentration in vacuo gave 92 mg of N-(4-bromoisothiazol-5-yl)leucine as a yellow powder.

Triethylamine (0.16 mL, 1.1 mmol) was added dropwise to a solution of N-(4-bromoisothiazol-5-yl)leucine (92 mg, 0.31 mmol), aminoacetonitrile hydrochloride (58 mg, 0.63 mmol) and benzotriazol-1-yl-oxytripyrrolidinophosphonium hexafluorophosphate (180 mg, 0.35 mmol) in N,N-dimethylformamide (1.0 mL) at 0° C. After stirring at rt for 3 h, the reaction vessel contents were poured into water and extracted with a 1:1 mixture of ether and ethyl acetate (3×). The combined extracts were washed with saturated sodium bicarbonate solution, then with saturated sodium chloride solution, and dried (Na$_2$SO$_4$). Concentration under reduced pressure and flash chromatography of the residue on silica gel eluting with a mixture of ethyl acetate and hexanes (2:3) afforded 91 mg of N$^2$-(4-bromoisothiazol-5-yl)-N$^1$-(cyanomethyl)leucinamide as a colorless foam.

A mixture of N$^2$-(4-bromoisothiazol-5-yl)-N$^1$-(cyanomethyl)leucinamide (91 mg, 0.27 mmol), 4-[4-(tert-butoxycarbonyl)piperazin-1-yl]phenylboronic acid (100 mg, 0.33 mmol, prepared as described in Example 1), PdCl$_2$(dppf) (5 mg, 0.006 mmol) and 2.0 M Na$_2$CO$_3$ aqueous solution (0.17 mL, 0.34 mmol) were heated to 85° C. in N,N-dimethylformamide (0.80 mL) under a nitrogen atmosphere for a total of 8 h. During this period additional catalyst (5 mg) was introduced at the 2 h, 4 h and 6 h time points. The reaction mixture was then cooled to rt, diluted with water and extracted with ethyl acetate (3×). The combined extracts were washed with saturated sodium chloride solution, dried (Na$_2$SO$_4$) and concentrated. Flash chromatography of the residue on silica eluting with a mixture of acetone and benzene (1:4) afforded 63 mg of N$^1$-(cyanomethyl)-N$^2$-[4-

(4-(tert-butoxycarbonyl)piperazin-1-ylphenyl)isothiazol-5-yl]leucinamide as a faint-tan foam.

Methanesulfonic acid (16 μL, 0.24 mmol) was added dropwise over 5 min to a stirred solution of $N^1$-(cyanomethyl)-$N^2$-[4-(4-(tert-butoxycarbonyl)piperazin-1-ylphenyl) isothiazol-5-yl]leucinamide (63 mg, 0.12 mmol) in THF (0.21 mL) at rt. Stirring was continued for 1 h before additional methanesulfonic acid (16 μL, 0.24 mmol) was introduced in the same manner with stirring for 1 h. A final portion of methanesulfonic acid (8 μL, 0.12 mmol) was added dropwise over 3 min and the mixture was stirred at rt for 8 h. The reaction was quenched by the careful addition of an excess of saturated sodium bicarbonate solution. Extraction with ethyl acetate (3×), drying of the combined organics ($Na_2SO_4$) and concentration in vacuo gave 48 mg of $N^1$-(cyanomethyl)-$N^2$-[4-(4-piperazin-1-ylphenyl) isothiazol-5-yl]leucinamide as a tan foam. MS (+ESI): 413.2 $[M+1]^+$.

Example 15

Synthesis of $N^1$-(Cyanomethyl)-$N^2$-[5-Methyl-4-(4-Piperazin-1-ylphenyl)Isoxazol-3-yl]Leucinamide To a mixture of 3-amino-4-bromo-5-methylisoxazole (2.58 g, 14.6 mmol) and DMAP (893 mg, 7.3 mmol) in 60 mL dichloromethane at −78° C. was added pyridine (6 ml, 74.1 mmol) followed by 2,2,2-trichloroethyl chloroformate (8 ml, 58 mmol). The reaction was allowed to warm to room temperature while stirring over ca. 4 hours. Ice water was added, the aqueous phase neutralized with saturated aq. $NaHCO_3$, and the product extracted with ether (3×), dried over $Na_2SO_4$ and concentrated in vacuo. The crude product was purified by flash chromatography (20% ethyl acetate/hexane) to afford 2,2,2-trichloroethyl 4-bromo-5-methyl-isoxazol-3-ylcarbamate.

To a dry degassed DMF solution (50 mL) of 2,2,2-trichloroethyl 4-bromo-5-methylisoxazol-3-ylcarbamate (2.67 g, 7.58 mmol), DL methyl leucate (2.31 g, 15.8 mmol), and triphenyl phosphine (4.11 g, 15.7 mmol) was added diisopropyl azodicarboxylate (3.1 ml, 15.7 mmol) at 0° C. over 2 hours. The reaction was allowed to warm to room temperature while stirring overnight. Water was added and the product was extracted with ether (2×) then ethyl acetate (2×), dried over $Na_2SO_4$ and concentrated in vacuo. The crude product was purified by flash chromatography (20% ethyl acetate/hexane) to afford methyl N-(4-bromo-5-methylisoxazol-3-yl)-N-[(2,2,2-trichloroethoxy)carbonyl]leucinate.

To a dry THF solution (20 mL) of methyl N-(4-bromo-5-methylisoxazol-3-yl)-N-[(2,2,2-trichloroethoxy)carbonyl] leucinate (1.19 g, 2.47 mmol) and activated zinc (10.1 g, 154 mmol) was added ca. 10 mL of 1 M $KH_2PO_4$ (10 mmol) at 0° C. The mixture was stirred for 1.5 hours, filtered through celite, washed with 150 mL ethyl acetate, and concentrated to a small volume. The mixture was then partitioned between ethyl acetate and saturated aqueous sodium bicarbonate, washed with brine, dried over sodium sulphate and concentrated in vacuo. The crude product was purified by flash chromatography (20% ethyl acetate/hexane) to afford methyl N-(4-bromo-5-methylisoxazol-3-yl)leucinate.

A methanol solution (25 mL) of methyl N-(4-bromo-5-methylisoxazol-3-yl)leucinate (602 mg, 1.97 mmol) and 2 M LiOH (10 ml, 20 mmol) was stirred for 50 minutes at room temperature. Ice water and aq. 10% HCl was added and the product was extracted with ethyl acetate (3×), dried over $Na_2SO_4$ and concentrated in vacuo to afford N-(4-bromo-5-methylisoxazol-3-yl)leucine which was used as is in the next step.

To N-(4-bromo-5-methylisoxazol-3-yl)leucine (841 mg, 2.90 mmol), aminoacetonitrile hydrochloride (674 mg, 7.30 mmol), PyBOP (1.73 g, 3.33 mmol) in dry degassed DMF (60 mL) was added triethylamine (1.4 mL, 10.0 mmol) dropwise. The reaction mixture was stirred for 15 hours at room temperature. Aqueous sat. $NaHCO_3$ was added and the product was extracted with diethyl ether (2×) and ethyl acetate (2×). The combined organic extracts were washed with brine, dried over sodium sulphate, and concentrated in vacuo. The crude product was purified by flash chromatography (60% ethyl acetate/hexane) to yield $N^2$-(4-bromo-5-methylisoxazol-3-yl)-$N^1$-(cyanomethyl)leucinamide.

$N^2$-(4-bromo-5-methylisoxazol-3-yl)-$N^1$-(cyanomethyl) leucinamide was treated with 4-[4-(tert-butoxycarbonyl)-1-piperazinyl]phenylboronic acid (prepared as described in Example 1) as described in Example 1 to afford, after BOC removal with methanesulfonic acid as described in Example 1, $N^1$-(cyanomethyl)-$N^2$-[5-methyl-4-(4-piperazin-1-ylphenyl)isoxazol-3-yl]leucinamide. MS (+APCI): 411.4 $[M+1]^+$ Example 16

Synthesis of N-(Cyanomethyl)-$N^2$-[1-Methyl-4-(4-Piperazin-1-ylphenyl)-1H-Pyrazol-3-yl]Leucinamide To a solution of 3-amino-4-bromo-1-methylpyrazole (2.69 g, 15.28 mmol) and DMAP (6.16 g, 50.45 mmol) in $CH_2Cl_2$ (100 mL) at 0° C. under dry nitrogen was added 2,2,2-trichloroethyl chloroformate (4.7 mL, 33.62 mmol) dropwise. The reaction mixture was warmed to rt and stirred for 1 hour. The reaction was quenched with water and the product extracted with EtOAc (2×), dried over $Na_2SO_4$, concentrated in vacuo and purified by flash chromatography over silica gel (EtOAc/Hex, 25/75, then 3/7 and 1/1) to afford bis(2,2,2-trichloroethyl) 4-bromo-1-methyl-1H-pyrazol-3-ylimidodicarbonate.

To bis(2,2,2-trichloroethyl) 4-bromo-1-methyl-1H-pyrazol-3-ylimidodicarbonate (5.73 g, 10.87 mmol) in THF (50 mL) was added dropwise an aqueous potassium hydroxide solution (2.0 M, 5.7 mL, 11.4 mmol) and the reaction was stirred at rt for 30 minutes. An additional aliquot of aqueous potassium hydroxide (2.0 M, 1.4 mL, 2.8 mmol) was added and the reaction stirred for ½ hour. The reaction was quenched with aqueous saturated ammonium chloride, water was added, the product extracted with $Et_2O$ (2×), dried over $Na_2SO_4$, concentrated in vacuo and purified by flash chromatography over silica gel (EtOAc/Hex, 1/1) to afford 2,2,2-trichloroethyl 4-bromo-1-methyl-1H-pyrazol-3-ylcarbamate.

To D/L-leucic acid (7.58 g, 57.36 mmol) in MeOH/$H_2O$ (9:1, 100 mL) was added a 20% solution of $Cs_2CO_3$ in water until the pH reached 7.0. The reaction mixture was concentrated in vacuo to dryness, DMF was added and concentrated in vacuo to dryness again. The solid was suspended in DMF (100 mL) at 0° C., 4-methoxybenzyl chloride (7.8 mL, 51.6 mmol) was added dropwise and the reaction mixture stirred overnight. The mixture was added to water and the product extracted with $Et_2O$, dried over $Na_2SO_4$, concentrated in vacuo and purified by flash chromatography over silica gel (EtOAc/Hex, 2/8, then 3/7) to afford 4-methoxybenzyl 2-hydroxy-4-methylpentanoate.

To 2,2,2-trichloroethyl 4-bromo-1-methyl-1H-pyrazol-3-ylcarbamate (2.402 g, 6.83 mmol), 4-methoxybenzyl 2-hydroxy-4-methylpentanoate (3.45 g, 13.67 mmol) and triphenyl phosphine (3.58 g, 13.67 mmol) in dry DMF (50 mL) under dry nitrogen was added dropwise diisopropyl azodicarboxylate (2.7 mL, 13.67 mmol) over 45 minutes and the reaction mixture stirred for 2 days. Water was added and the product extracted with ether (2×), dried over $Na_2SO_4$, concentrated in vacuo and purified by flash chromatography over silica gel (EtOAc/Hex, 2/8) to afford 4-methoxybenzyl N-(4-bromo-1-methyl-1H-pyrazol-3-yl)-N-[(2,2,2-trichloroethoxy)carbonyl]leucinate.

To 4-methoxybenzyl N-(4-bromo-1-methyl-1H-pyrazol-3-yl)-N-[(2,2,2-trichloroethoxy)carbonyl]leucinate (1.72 g, 2.89 mmol) in dry THF (50 mL) was added activated zinc powder (1.89 g, 28.9 mmol) followed by an aqueous solution of $KH_2PO_4$ (1.0 M, 5.8 mL, 11.6 mmol) and the reaction mixture was stirred for ½ hour. Additional aliquots of activated zinc powder (950 mg, 14.45 mmol) and aqueous solution of $KH_2PO_4$ (1.0 M, 2.9 mL, 2.9 mmol) were added and the reaction mixture stirred for 1½ hour. The zinc powder was filtered off, rinsed with $Et_2O$ and water and the product extracted with ether (2×), dried over $Na_2SO_4$, concentrated in vacuo and purified by flash chromatography over silica gel (EtOAc/Hex, 25/75, then 3/7) to afford 4-methoxybenzyl N-(4-bromo-1-methyl-1H-pyrazol-3-yl)leucinate.

To 4-methoxybenzyl N-(4-bromo-1-methyl-1H-pyrazol-3-yl)leucinate (1.19 g, 2.89 mmol) in MeOH (60 mL) was added dropwise an aqueous LiOH solution (1.0 M, 14.5 mL, 14.5 mmol) and the reaction was stirred for ½ hour. The reaction was acidified (pH=4–5) with aqueous 10% HCl and the product extracted with EtOAc (3×), dried over $Na_2SO_4$, concentrated in vacuo and purified by flash chromatography over silica gel (Hex/EtOAc/AcOH, 70/29/1, then 50/49/1) to afford N-(4-bromo-1-methyl-1H-pyrazol-3-yl)leucine.

To N-(4-bromo-1-methyl-1H-pyrazol-3-yl)leucine (366 mg, 1.26 mmol), PyBOP (725 mg, 1.39 mmol), aminoacetonitrile hydrochloride (257 mg, 2.78 mmol) in dry DMF (15 mL) under dry nitrogen was added triethylamine (0.62 mL, 4.45 mmol) dropwise and the reaction stirred for 2½ hours. Aqueous sat. $NaHCO_3$ was added and the product extracted with $Et_2O$ (2×), dried over $Na_2SO_4$, concentrated in vacuo and purified by flash chromatography over silica gel (EtOAc/Hex, 6/4) to afford $N^2$-(4-bromo-1-methyl-1H-pyrazol-3-yl)-$N^1$-(cyanomethyl)leucinamide.

To $N^2$-(4-bromo-1-methyl-1H-pyrazol-3-yl)-$N^1$-(cyanomethyl)leucinamide (250 mg, 0.762 mmol), and 4-[4-(tert-butoxycarbonyl)-1-piperazinyl]phenylboronic acid (350 mg, 1.14 mmol, prepared as described in Example 1) in DMF (8 mL) under dry nitrogen was added aqueous sodium carbonate (2.0 M, 0.9 mL, 1.7 mmol) followed by the catalyst $PdCl_2$(dppf) (20 mg, 0.022 mmol). The reaction was heated to 90° C. for 0.5 hours and an additional aliquot of $PdCl_2$(dppf) (20 mg, 0.022 mmol) was added and the reaction mixture heated for 1½ hour during which time an additional aliquot of $PdCl_2$(dppf) (20 mg, 0.022 mmol) was added. Water was added and the product extracted with ether (2×), dried over $Na_2SO_4$, concentrated in vacuo and purified by flash chromatography over silica gel (EtOAc/Hex, 6/4 then 8/2) to afford $N^1$-(cyanomethyl)-$N^2$-(4-{4-[4-(tert-butoxycarbonyl)piperazin-1-yl]phenyl}-1-methyl-1H-pyrazol-3-yl)leucinamide.

To $N^1$-(cyanomethyl)-$N^2$-(4-{4-[4-(tert-butoxycarbonyl)piperazin-1-yl]phenyl}-1-methyl-1H-pyrazol-3-yl)leucinamide (144 mg, 0.283 mmol) in dry THF (0.5 mL) under dry nitrogen was gradually added a total of 5 equivalents of $MeSO_3H$ (100 μL, 1.42 mmol) over a period of 4 hours in portions of 1–2 equivalents at a time and the reaction mixture was stirred overnight. Aqueous sat. $NaHCO_3$ was added carefully and the product was extracted with EtOAc (2×), dried over $Na_2SO_4$, concentrated in vacuo, and purified by flash chromatography over silica gel ($NH_4OH$/MeOH/$CH_2Cl_2$, 1/9/90) to afford $N^1$-(cyanomethyl)-$N^2$-[1-methyl-4-(4-piperazin-1-ylphenyl)-1H-pyrazol-3-yl]leucinamide. MS (–ESI): 408.4 [M–1]$^-$.

Example 17

Synthesis of $N^1$-(Cyanomethyl)-$N^2$-[4-(4-Piperazin-1-ylphenyl)-1,2,5-Oxadiazol-3-yl]Leucinamide To a suspension of tert-butyl 4-(4-formylphenyl)piperazine-1-carboxylate (3.89 g, 13.41 mmol, prepared as described in Example 10) and $K_2CO3$ (1.02 g, 7.38 mmol) in EtOH (50 mL) was added hydroxylamine hydrochloride (1.4 g, 20.1 mmol) in water (saturated, approx. 2 mL) and the reaction mixture stirred overnight. The reaction was filtered, concentrated in vacuo, water was added and the product filtered to afford tert-butyl 4-{4-[(E)-(hydroxyimino)methyl]phenyl}piperazine-1-carboxylate.

To tert-butyl 4-{4-[(E)-(hydroxyimino)methyl]phenyl}piperazine-1-carboxylate (1.593 g, 5.22 mmol) in $CH_2Cl_2$ (25 mL) was gradually added Javex (approx. 10% NaOCl, 19.5 mL,.26.1 mmol) and the reaction mixture stirred for 1 hour. Potassium cyanide (3.4 g, 52.2 mmol) was added and the reaction stirred for 1 hour. The reaction was poured into brine and the product extracted with EtOAc (2×), dried over $Na_2SO_4$, concentrated in vacuo with silica gel (to pre-adsorb product on silica gel) and purified by flash chromatography over silica gel (EtOAc/Hex, 1/1) to afford tert-butyl 4-(4-[(Z)-cyano(hydroxyimino)methyl]phenyl}piperazine-1-carboxylate.

To tert-butyl 4-{4-[(Z)-cyano(hydroxyimino)methyl]phenyl}piperazine-1-carboxylate (1.39 g, 4.21 mmol) in EtOH (50 mL) was added an aqueous solution of pre-mixed hydroxylamine hydrochloride (440 mg, 6.32 mmol) and $NaHCO_3$ (535 mg, 6.32 mmol) in water (15 mL) and the reaction was refluxed overnight. An additional aliquot of hydroxylamine hydrochloride (440 mg, 6.32 mmol) and $NaHCO_3$ (535 mg, 6.32 mmol) in water (10 mL) was added and the reaction was refluxed for 2 hours. Aqueous NaOH (1.0 M, 42.1 mL) was added and the reaction was refluxed for 1 hour. An additional aliquot of NaOH (1.0 M, 21 mL) was added and the reaction was refluxed for 3 hours. After cooling to rt, the reaction mixture was poured into brine and the product extracted with EtOAc (2×), dried over $Na_2SO_4$, concentrated in vacuo, and purified by flash chromatography over silica gel (EtOAc/Hex, 4/6) to afford tert-butyl 4-[4-(4-amino-1,2,5-oxadiazol-3-yl)phenyl]piperazine-1-carboxylate.

To tert-butyl 4-[4-(4-amino-1,2,5-oxadiazol-3-yl)phenyl]piperazine-1-carboxylate (700 mg, 2.03 mmol) and DMAP (820 mg, 6.7 mmol) in 1,2-dichloroethane (50 mL) under dry nitrogen was added 2,2,2-trichloroethyl chloroformate (0.62 mL, 4.5 mmol) dropwise and the reaction was refluxed for ½ hour. An additional aliquot of DMAP (820 mg, 6.7 mmol) and 2,2,2-trichloroethyl chloroformate (0.62 mL, 4.5 mmol) were added and the reaction mixture was refluxed for 1 hour. Further aliquots of DMAP (820 mg, 6.7 mmol) and 2,2,2-trichloroethyl chloroformate (0.62 mL, 4.5 mmol) were added and the reaction mixture was refluxed for a total of 4 hours. After cooling to rt, the reaction was poured into aqueous 10% HCl and the product extracted with EtOAc (2×), dried over $Na_2SO_4$, concentrated in vacuo and purified by flash chromatography over silica gel (EtOAc/Hex, 3/7, then 1/1) to afford tert-butyl 4-[4-(4-{bis[(2,2,2-trichloroethoxy)carbonyl]amino}-1,2,5-oxadiazol-3-yl)phenyl]piperazine-1-carboxylate.

To tert-butyl 4-[4-(4-{bis[(2,2,2-trichloroethoxy)carbonyl]amino}-1,2,5-oxadiazol-3-yl)phenyl]piperazine-1-carboxylate (1.21 g, 1.74 mmol) in THF (25 mL) was added an aqueous solution of NaOH (1.0 M, 4.0 mL, 4.0 mmol) dropwise and the reaction mixture was stirred for 1 hour. The reaction was poured into brine and the product extracted with $Et_2O$ (2×), dried over $Na_2SO_4$, concentrated in vacuo and purified by flash chromatography over silica gel (EtOAc/Hex, 3/7) to afford tert-butyl 4-[4-(4-{[(2,2,2-trichloroethoxy)carbonyl]amino}-1,2,5-oxadiazol-3-yl)phenyl]piperazine-1-carboxylate.

To tert-butyl 4-[4-(4-{[(2,2,2-trichloroethoxy)carbonyl]amino}-1,2,5-oxadiazol-3-yl)phenyl]piperazine-1-carboxylate (485 mg, 0.932 mmol), methyl 2-hydroxy-4-methylpentanoate (275 mg, 1.87 mmol) and triphenyl phosphine (490 mg, 1.87 mmol) in dry DMF (15 mL) at 0° C. under dry nitrogen was added diisopropyl azodicarboxylate (0.375 mL, 1.87 mmol) dropwise over ½ hour and the reaction mixture stirred overnight at rt. The reaction was poured into water and the product extracted with $Et_2O$ (2×), dried over $Na_2SO_4$, concentrated in vacuo and purified by flash chromatography over silica gel (EtOAc/Hex, 2/8) to afford methyl N-(4-{4-[4-(tert-butoxycarbonyl)piperazin-1-yl]phenyl}-1,2,5-oxadiazol-3-yl)-N-[(2,2,2-trichloroethoxy)carbonyl]leucinate.

To methyl N-(4-{4-[4-(tert-butoxycarbonyl)piperazin-1-yl]phenyl}-1,2,5-oxadiazol-3-yl)-N-[(2,2,2-trichloroethoxy)carbonyl]leucinate (605 mg, 0.932 mmol) in THF (20 mL) was added activated zinc powder (610 mg, 9.32 mmol) and an aqueous solution of $KH_2PO_4$ (1.0 M, 1.8 mL, 1.8 mmol) dropwise. After 15 min an additional aliquot of aqueous $KH_2PO_4$ solution was added (1.0 M, 1.8 mL, 1.8 mmol) and the reaction mixture was stirred for 4 hours. The zinc powder was filtered off, rinsed with $Et_2O$ and water and the product extracted with ether (2×), dried over $Na_2SO_4$, concentrated in vacuo and purified by flash chromatography over silica gel (EtOAc/Hex, 25/5) to afford methyl N-(4-{4-[4-(tert-butoxycarbonyl)piperazin-1-yl]phenyl}-1,2,5-oxadiazol-3-yl)leucinate.

To methyl N-(4-{4-[4-(tert-butoxycarbonyl)piperazin-1-yl]phenyl}-1,2,5-oxadiazol-3-yl)leucinate (375 mg, 0.793 mmol) in MeOH (20 mL) was added an aqueous solution of LiOH (2.0 M, 2.0 mL, 4.0 mmol) and the reaction mixture was stirred for 2 hours. An additional aliquot of aqueous LiOH (2.0 M, 2.0 mL, 4.0 mmol) was added and the reaction mixture was stirred for 1 hour. The reaction was acidified (pH=4–5) with aqueous 10% HCl, brine was added and the product extracted with EtOAc (3×), dried over $Na_2SO_4$, concentrated in vacuo and purified by flash chromatography over silica gel (Hex/EtOAc/AcOH, 50/49/1) to afford N-(4-{4-[4-(tert-butoxycarbonyl)piperazin-1-yl]phenyl}-1,2,5-oxadiazol-3-yl)leucine.

To N-(4-{4-[4-(tert-butoxycarbonyl)piperazin-1-yl]phenyl}-1,2,5-oxadiazol-3-yl)leucine (350 mg, 0.763 mmol), PyBOP (440 mg, 0.84 mmol), aminoacetonitrile hydrochloride (155 mg, 1.68 mmol) in dry DMF (10 mL) under dry nitrogen was added triethylamine (0.38 mL, 2.67 mmol) dropwise and the reaction stirred for 2½ hours. Aqueous sat. $NaHCO_3$ was added and the product extracted with $Et_2O$ (2×), dried over $Na_2SO_4$, concentrated in vacuo and purified by flash chromatography over silica gel (EtOAc/Hex, 4/6) to afford $N^1$-(cyanomethyl)-$N^2$-(4-{4-[4-(tert-butoxycarbonyl)piperazin-1-yl]phenyl}-1,2,5-oxadiazol-3-yl)leucinamide.

To $N^1$-(cyanomethyl)-$N^2$-(4-{4-[4-(tert-butoxycarbonyl)piperazin-1-yl]phenyl}-1,2,5-oxadiazol-3-yl)leucinamide (170 mg, 0.33 mmol) in dry THF (1 mL) under dry nitrogen was gradually added a total of 6 equivalents of $MeSO_3H$ (120 µL, 2.0 mmol) over a period of 2 hours in portions of 2 equivalents at a time and the reaction mixture stirred overnight. Aqueous sat. $NaHCO_3$ was added carefully and the product extracted with EtOAc (2×), dried over $Na_2SO_4$, concentrated in vacuo and purified by flash chromatography over silica gel ($NH_4OH/MeOH/CH_2Cl_2$, 1/9/90) to afford $N^1$-(cyanomethyl)-$N^2$-[4-(4-piperazin-1-ylphenyl)-1,2,5-oxadiazol-3-yl]leucinamide.

MS (+APCI): 455.2 $[M+1]^+$.

Example 18

Synthesis of $N^1$-(Cyanomethyl)-$N^2$-[4-(4-Piperazin-1-ylphenyl)-1H-Pyrazol-3-yl]Leucinamide To 3-amino-4-bromopyrazole (10.9 g, 67.29 mmol) and DMAP (17.26 g, 141.31 mmol) in MeCN (250 mL) at −78° C. under dry nitrogen was added di-tert-butyl dicarbonate (16.15 g, 74.02 mmol) in MeCN (250 mL) and the reaction gradually warmed to rt and stirred for 3 hours. EtOAc was added and washed with aqueous 10% citric acid, aqueous sat. $NaHCO_3$ and water, dried over $Na_2SO_4$, concentrated in vacuo and purified by flash chromatography over silica gel (EtOAc/Hex, 3/7, then 1/1) to afford predominantly the more polar isomer whose structure was arbitrarily assigned as tert-butyl 3-amino-4-bromo-1H-pyrazole-1-carboxylate (the other possible isomer corresponds to tert-butyl 5-amino-4-bromo-1H-pyrazole-1-carboxylate).

To tert-butyl 3-amino4-bromo-1H-pyrazole-1-carboxylate (5.43 g, 20.73 mmol) and DMAP (8.36 g, 68.41 mmol) in $CH_2Cl_2$ (100 mL) at 0° C. under dry nitrogen was added 2,2,2-trichloroethyl chloroformate (6.3 mL, 45.61 mmol) dropwise and the reaction warmed to rt and stirred for 1 hour. Additional aliquots of DMAP (8.36 g, 68.41 mmol) and 2,2,2-trichloroethyl chloroformate (6.3 mL, 45.61 mmol) were added and the reaction mixture was stirred for 2 hours. $Et_2O$ was added and the reaction poured into aqueous 10% HCl, extracted with EtOAc (2×), dried over $Na_2SO_4$, concentrated in vacuo and purified by flash chromatography over silica gel (EtOAc/Hex, 2/8) to afford tert-butyl 3-{bis[(2,2,2-trichloroethoxy)carbonyl]amino}4bromo-1H-pyrazole-1-carboxylate.

To tert-butyl 3-{bis[(2,2,2-trichloroethoxy)carbonyl]amino}-4-bromo-1H-pyrazole-1-carboxylate (12.7 g, 20.73 mmol) in THF (200 mL) was added activated zinc powder (13.5 g, 207.3 mmol) followed by an aqueous solution of $KH_2PO_4$ (1.0 M, 41.5 mL, 41.5 mmol) dropwise and the reaction was stirred for 3 hours at rt. The zinc powder was filtered off, rinsed with $Et_2O$ and water, the aqueous phase extracted with $Et_2O$ (2×), and the combined organics dried over $Na_2SO_4$, concentrated in vacuo and purified by flash chromatography over silica gel (EtOAc/Hex, 2/8) to afford tert-butyl 4-bromo-3-{[(2,2,2-trichloroethoxy)carbonyl]amino }-1H-pyrazole-1-carboxylate.

To tert-butyl 4-bromo-3-{[(2,2,2-trichloroethoxy)carbonyl]amino}-1H-pyrazole-1-carboxylate (2.32 g, 5.3 mmol), 4-methoxybenzyl 2-hydroxy-4-methylpentanoate (2.02 g, 8.0 mmol, prepared as described in Example 16) and triphenyl phosphine (2.1 g, 8.0 mmol) in dry DMF (50 mL) at 0° C. under dry nitrogen was added diisopropyl azodicarboxylate (1.6 mL, 8.0 mmol) dropwise and the reaction was stirred overnight. The reaction was poured into water and the product extracted with $Et_2O$ (2×), dried over $Na_2SO_4$, concentrated in vacuo and purified by flash chromatography over silica gel (EtOAc/Hex, 2/8) to afford 4-methoxybenzyl N-[4-bromo-1-(tert-butoxycarbonyl)-1H-pyrazol-3-yl]—N-[(2,2,2-trichloroethoxy)carbonyl]leucinate.

To 4-methoxybenzyl N-[4-bromo-1-(tert-butoxycarbonyl)-1H-pyrazol-3-yl]-N-[(2,2,2-trichloroethoxy)carbonyl]leucinate (2.38 g, 3.54 mmol) in THF (40 mL) was added activated zinc powder (2.3 g, 35.4 mmol) and an aqueous solution of $KH_2PO_4$ (1.0 M, 14.2 mL, 14.2 mmol) dropwise. After 1 hour additional aliquots of activated zinc powder (2.3 g, 35.4 mmol) and aqueous $KH_2PO_4$ solution were added (1.0 M, 14.2 mL, 14.2 mmol) and the reaction mixture was stirred for 1 hour. The zinc powder was filtered off, rinsed with $Et_2O$ and water and the product extracted with ether (2×), dried over $Na_2SO_4$, concentrated in vacuo, and purified by flash chromatography over silica gel (EtOAc/Hex, 3/7) to afford 4-methoxybenzyl N-[4-bromo-1-(tert-butoxycarbonyl)-1H-pyrazol-3-yl]leucinate.

To 4-methoxybenzyl N-[4-bromo-1-(tert-butoxycarbonyl)-1H-pyrazol-3-yl]leucinate (1.45 g, 2.92 mmol), 4-[4-(tert-butoxycarbonyl)-1-piperazinyl]phenylboronic acid (1.117 g, 3.65 mmol, prepared as described in Example 1) and catalyst $PdCl_2$(dppf) (75 mg, 0.09 mmol) in DMF (30 mL) under dry nitrogen was added aqueous sodium carbonate (2.0 M, 3.3 mL, 6.6 mmol). The reaction was heated to 90° C. for 0.5 hour and an additional aliquot of $PdCl_2$(dppf) (20 mg, 0.022 mmol) was added and the reaction mixture was heated for 1½ hour. Water was added and the product extracted with ether (2×), dried over $Na_2SO_4$, concentrated in vacuo, and purified by flash chromatography over silica gel (EtOAc/Hex, 25/75) to afford 4-methoxybenzyl N-(1-(tert-butoxycarbonyl)-4-{4-[4-(tert-butoxycarbonyl)piperazin-1-yl]phenyl}-1H-pyrazol-3-yl)leucinate.

To 4-methoxybenzyl N-(1-(tert-butoxycarbonyl)4-{4-[4-(tert-butoxycarbonyl)piperazin-1-yl]phenyl}-1H-pyrazol-3-yl)leucinate (1.14 g, 1.68 mmol) in EtOH (30 mL) was added the catalyst palladium on carbon (10%, 500 mg) and the reaction was stirred under a hydrogen atmosphere overnight. After degassing with nitrogen, $CH_2Cl_2$ was added and the reaction mixture was filtered on celite, washed with EtOH, concentrated in vacuo and purified by flash chromatography over silica gel (AcOH/EtOAc/Hex, 1/49/50) to afford N-(1-(tert-butoxycarbonyl)-4-{4-[4-(tert-butoxycarbonyl)piperazin-1-yl]phenyl}-1H-pyrazol-3-yl)leucine.

To N-(1-(tert-butoxycarbonyl)-4-{4-[4-(tert-butoxycarbonyl)piperazin-1-yl]phenyl}-1H-pyrazol-3-yl)leucine (864 mg, 1.55 mmol), PyBOP (890 mg, 1.71 mmol), aminoacetonitrile hydrochloride (315 mg, 3.41 mmol) in dry DMF (40 mL) under dry nitrogen was added triethylamine (0.76 mL, 5.43 mmol) dropwise and the reaction was stirred for 4½ hours. Aqueous sat. $NaHCO_3$ was added and the product extracted with $Et_2O$ (2×), dried over $Na_2SO_4$, concentrated in vacuo and purified by flash chromatography over silica gel (EtOAc/Hex, 4/6) to afford $N^1$-(cyanomethyl)-$N^2$-(1-(tert-butoxycarbonyl)-4-{4-[4-(tert-butoxycarbonyl)piperazin-1-yl]phenyl}-1H-pyrazol-3-yl)leucinamide.

To $N^1$-(cyanomethyl)-$N^2$-(1-(tert-butoxycarbonyl)-4-{4-[4-(tert-butoxycarbonyl)piperazin-1-yl]phenyl}-1H-pyrazol-3-yl)leucinamide (163 mg, 0.274 mmol) in dry THF (0.5 mL) under dry nitrogen was gradually added a total of 5 equivalents of $MeSO_3H$ (100 μL, 1.37 mmol) over a period of 3 hours in portions of 1–2 equivalents at a time and the reaction mixture was stirred overnight. Aqueous sat. $NaHCO_3$ was added carefully and the product extracted with EtOAc (2×), dried over $Na_2SO_4$, concentrated in vacuo and purified by flash chromatography over silica gel $NH_4OH$/ MeOH/$CH_2Cl_2$, 1/9/90) to afford $N^1$-(cyanomethyl)-$N^2$-[4-(4-piperazin-1-ylphenyl)-1H-pyrazol-3-yl]leucinamide. MS (+ESI): 398.4 $[M+1]^+$.

Example 19

Synthesis of N-(Cyanomethyl)-$N^2$-[3-Methyl-4-(4-Piperzin-1-ylphenyl)Isoxazol-5-yl]Leucinamide To 5-amino-3-methylisoxazole (4.63 g, 47.2 mmol) in $CH_2Cl$/AcOH (9:1, 100 mL) was added bromine (2.65 mL, 51.9 mmol) dropwise and the reaction was stirred for 2 hours. Water and $Et_2O$ were added followed by aqueous sat. $NaHCO_3$, the product extracted with $Et_2O$ (2×), dried over $Na_2SO_4$, concentrated in vacuo, and purified by flash chromatography over silica gel (EtOAc/Hex, 3/7) to afford 4-bromo-3-methylisoxazol-5-amine.

To 4-bromo-3-methylisoxazol-5-amine (2.63 g, 14.85 mmol), 4-[4-(tert-butoxycarbonyl)-1-piperazinyl]phenylboronic acid (5.7 g, 18.57 mmol, prepared as described in Example 1) and catalyst $PdCl_2$(dppf) (365 mg, 0.45 mmol) in DMF (100 mL) under dry nitrogen was added aqueous sodium carbonate (2.0 M, 18.6 mL, 37 mmol). The reaction was heated to 95° C. for 1 hour and an additional aliquot of $PdCl_2$(dppf) (365 mg, 0.45 mmol) was added and the reaction mixture was heated overnight. Water was added and the product extracted with ether (2×), dried over $Na_2SO_4$, concentrated in vacuo, and purified by flash chromatography over silica gel (EtOAc/Hex, 4/6, then 1/1) to afford tert-butyl 4-[4-(5-amino-3-methylisoxazol-4-yl)phenyl]piperazine-1-carboxylate.

To tert-butyl 4-[4-(5-amino-3-methylisoxazol-4-yl)phenyl]piperazine-1-carboxylate (900 mg, 2.51 mmol) and DMAP (1.02 g, 8.3 mmol) in $CH_2Cl_2$ (25 mL) at 0° C. under dry nitrogen was added 2,2,2-trichloroethyl chloroformate (1.02 g, 8.3 mmol) dropwise and the reaction was warned to rt and stirred for 1 hour. Additional aliquots of DMAP (1.02 g, 8.3 mmol) and 2,2,2-trichloroethyl chloroformate (1.02 g, 8.3 mmol) were added and the reaction mixture was stirred for 2½ hours. $Et_2O$ was added and the reaction was poured into aqueous 10% HCl, extracted with $Et_2O$ (2×), dried over $Na_2SO_4$, concentrated in vacuo and purified by flash chromatography over silica gel (EtOAc/Hex, 3/7) to afford tert-butyl 4-[4-(3-methyl-5-{[(2,2,2-trichloroethoxy)carbonyl]amino}isoxazol-4-yl)phenyl]piperazine-1-carboxylate.

To tert-butyl 4-[4-(3-methyl-5-{[(2,2,2-trichloroethoxy)carbonyl]amino}isoxazol-4-yl)phenyl]piperazine-1-carboxylate (617 mg, 1.16 mmol), methyl 2-hydroxy-4-methylpentanoate (255 mg, 1.74 mmol) and triphenyl phosphine (460 mg, 1.74 mmol) in dry DMF (15 mL) at 0° C. under dry nitrogen was added diisopropyl azodicarboxylate (0.35 mL, 1.74 mmol) dropwise over ½ hour and the reaction mixture was stirred for 2 days at rt. The reaction was poured into water and the product extracted with $Et_2O$ (2×), dried over $Na_2SO_4$, concentrated in vacuo and purified by flash chromatography over silica gel (EtOAc/Hex, 25/75) to afford methyl N-(4-{4-[4-(tert-butoxycarbonyl)piperazin-1-yl]phenyl}-3-methylisoxazol-5-yl)-N-[(2,2,2-trichloroethoxy)carbonyl]leucinate.

To methyl N-(4-{4-[4-(tert-butoxycarbonyl)piperazin-1-yl]phenyl}-3-methylisoxazol-5-yl)-N-[(2,2,2-trichloroethoxy)carbonyl]leucinate (688 mg, 1.04 mmol) in THF (20 mL) was added activated zinc powder (686 mg, 10.4 mmol) and an aqueous solution of $KH_2PO_4$ (1.0 M, 5.2 mL, 5.2 mmol) dropwise. After ½ hour additional aliquots of activated zinc powder (686 mg, 10.4 mmol) and aqueous $KH_2PO_4$ solution were added (1.0 M, 5.2 mL, 5.2 mmol) and the reaction mixture was stirred for 1 hour. The zinc powder was filtered off, rinsed with Et$_2$O and water and the product extracted with ether (2×), dried over Na$_2$SO$_4$, concentrated iii vacuo and purified by flash chromatography over silica gel (EtOAc/Hex, 3/7) to afford methyl N-(4-{4-[4-(tert-butoxycarbonyl)piperazin-1-yl]phenyl}-3-methylisoxazol-5-yl)leucinate.

To methyl N-(4-{4-[4-(tert-butoxycarbonyl)piperazin-1-yl]phenyl}-3-methylisoxazol-5-yl)leucinate (450 mg, 0.926 mmol) in MeOH (15 mL) was added an aqueous solution of LiOH (2.0 M, 2.3 mL, 4.6 mmol) and the reaction mixture was stirred overnight. The reaction was acidified (pH=4–5) with aqueous 10% HCl, the product extracted with EtOAc (3×), dried over Na$_2$SO$_4$, concentrated in vacuo and purified by flash chromatography over silica gel (AcOH(EtOAc/Hex, 1/29/70) to afford N-(4-{4-[4-(tert-butoxycarbonyl)piperazin-1-yl]phenyl}-3-methylisoxazol-5-yl)leucine.

To N-(4-{4-[4-(tert-butoxycarbonyl)piperazin-1-yl]phenyl}-3-methylisoxazol-5-yl)leucine (415 mg, 0.879 mmol), PyBOP (505 mg, 0.97 mmol), aminoacetonitrile hydrochloride (179 mg, 1.93 mmol) in dry DMF (15 mL) under dry nitrogen was added triethylamine (0.44 mL, 3.1 mmol) dropwise and the reaction was stirred for 3 hours. Aqueous sat. NaHCO$_3$ was added and the product extracted with Et$_2$O (2×), dried over Na$_2$SO$_4$, concentrated in vacuo, and purified by flash chromatography over silica gel (EtOAc/Hex, 6/4) to afford N$^1$-(cyanomethyl)-N$^2$-(4-{4-[4-(tert-butoxycarbonyl)piperazin-1-yl]phenyl}-3-methylisoxazol-5-yl)leucinamide.

To N$^1$-(cyanomethyl)-N$^2$-(4-{4-[4-(tert-butoxycarbonyl)piperazin-1-yl]phenyl}-3-methylisoxazol-5-yl)leucinamide (210 mg, 0.411 mmol) in dry THF (0.5 mL) under dry nitrogen was gradually added a total of 5 equivalents of MesO$_3$H (100 μL, 1.37 mmol) over a period of 3 hours in portions of 1–2 equivalents at a time and the reaction mixture was stirred overnight. Aqueous sat. NaHCO$_3$ was added carefully and the product was extracted with EtOAc (2×), dried over Na$_2$SO$_4$, concentrated in vacuo and purified by flash chromatography over silica gel (NH$_4$OH/MeOH/CH$_2$Cl$_2$, 1/9/90) to afford N-(cyanomethyl)-N$^2$-[3-methyl-4-(4-piperazin-1-ylphenyl)isoxazol-5-yl]leucinamide. MS (−ESI): 409.7 [M−1]$^-$.

Example 20

Synthesis of N-(Cyanomethyl)-4-Methyl-2-{[4'-(Pyrrolidin-1-ylmethyl)-1,1'-Biphenyl-4-yl]Thio}Pentanamide 2-[(4-Bromophenyl)thio]-N-(cyanomethyl)-4-methylpentanamide (5.0 g, 14.6 mmol, prepared by the method described in Example 8, using 4-bromothiophenol as the starting material) was mixed with4,4,4',4',5,5,5',5'-octamethyl-2,2'-bi-1,3,2-dioxaborolane (4.46 g, 17.6 mmol) and potassium acetate (4.3 g, 43.8 mmol) in DMF (45 mL). The reaction flask was thoroughly degassed with dry nitrogen and PdCl$_2$dppf (358 mg, 0.44 mmol) was added. The reaction mixture was stirred at 80° C. for 18 h. Aqueous sat. NaHCO$_3$ was added and the product was extracted with EtOAc (3×), dried over MgSO$_4$, concentrated in vacuo, and purified by flash chromatography (30% EtOAc/hexanes) to give N-(cyanomethyl)-4-methyl-2-{[4-(4,4,5,5-tetramethyl-1,3,2-dioxaborolan-2-yl)phenyl]thio}pentanamide.

4-Bromobenzylamine hydrochloride (8.0 g, 36 mmol) was dissolved in dioxane (40 mL) and water (40 mL). Sodium hydroxide (10.8 mL of a 10 M aqueous solution, 108 mmol) and di(tert-butyl) dicarbonate (9.1 g, 43.2 mmol) were added. The reaction mixture was stirred until disappearance of the starting material was observed by TLC. The aqueous layer was acidified to pH 1, tert-butyl 4-bromobenzylcarbamate was extracted with EtOAc (3×), dried over MgSO$_4$, concentrated in vacuo, and used without any further purification.

N-(cyanomethyl)-4-methyl-2-{[4-(4,4,5,5-tetramethyl-1,3,2-dioxaborolan-2-yl)phenyl]thio}pentanamide (1.64 g, 4.22 mmol) and tert-butyl 4-bromobenzylcarbamate (1.33 g, 4.64 mmol) were mixed in DMF (12 mL). After addition of sodium carbonate (7.4 mL of a 2.0 M solution, 14.8 mmol), the reaction flask was thoroughly degassed with dry nitrogen. PdCl$_2$dppf (103 mg, 0.13 mmol) was added and the reaction mixture was heated at 80° C. for 4 h. Aqueous sat. NaHCO$_3$ was added, the product was extracted with EtOAc (3×), dried over MgSO$_4$, concentrated in vacuo, and purified by flash chromatography (40% EtOAc/hexanes) to afford tert-butyl {4'-[(1-{[(cyanomethyl)amino]carbonyl}-3-methylbutyl)thio]-1,1'-biphenyl-4-yl}methylcarbamate.

Tert-butyl {4'-[(1-{[(cyanomethyl)amino]carbonyl}-3-methylbutyl)thio]-1,1'-biphenyl-4-yl}methylcarbamate (1.75 g, 3.74 mmol) was dissolved in dioxane (15 mL). Methanesulfonic acid (485 μL, 7.5 mmol) was added and the reaction mixture was stirred for 18 h. Aqueous sat. NaHCO$_3$ was added and the product was extracted with EtOAc (3×), dried over MgSO$_4$, concentrated in vacuo, and purified by flash chromatography (95:3:2 dichloromethane/methanol/triethylamine) to yield 2-{[4'-(aminomethyl)-1,1'-biphenyl-4-yl]thio}-N-(cyanomethyl)-4-methylpentanamide.

2-{[4'-(Aminomethyl)-1,1'-biphenyl-4-yl]thio}-N-(cyanomethyl)-4-methylpentanamide (120 mg, 0.33 mmol) was mixed with cyclopentanone (234 μL, 2.64 mmol), sodium cyanoborohydride (25 mg, 0.40 mmol) and MgSO$_4$ (200 mg) and stirred for 18 h. Aqueous sat. NaHCO$_3$ was added, the product was extracted with EtOAc (3×), dried over MgSO$_4$, concentrated in vacuo, and purified by flash chromatography (100% EtOAc to 2% methanol/EtOAc) to afford N-(cyanomethyl)-4-methyl-2-{[4'-(pyrrolidin-1-ylmethyl)-1,1'-biphenyl4-yl]thio}pentanamide. MS (+APCI): 436.3 [M+1]$^+$.

Example 21

Synthesis of N$^1$-(Cyanomethyl)-N$^2$-{4-[4-(N,N-Dimethylglycyl)Phenyl]Isothiazol-3-yl}Leucinamide N$^2$-(4-bromoisothiazol-3-yl)-N$^1$-(cyanomethyl)leucinamide (100 mg, 0.30 mmol, prepared as described in Example 13) was submitted to a Suzuki coupling with 4-acetylphenylboronic acid (99 mg, 0.60 mmoles) as described in Example 1 to afford N$^2$-[4-(4-acetylphenyl)isothiazol-3-yl]-N$^1$-(cyanomethyl)leucinamide which was purified by flash chromatography (30% to 55% EtOAc/hexanes).

N$^2$-[4-(4-acetylphenyl)isothiazol-3-yl]-N$^1$-(cyanomethyl)leucinamide (100 mg, 0.27 mmol) was reacted with phenyltrimethylammonium tribromide (100 mg, 0.27 mmol) in THF (0.30 mL) for 48 h. Aqueous sat. NaHCO$_3$ was added and the product was extracted with EtOAc (3×), dried over MgSO$_4$, concentrated in vacuo, and purified by flash chromatography (30 to 65% EtOAc/hexanes) to yield N$^2$-{4-[4-(bromoacetyl)phenyl]isothiazol-3-yl }-N'-(cyanomethyl)leucinamide.

N$^2$-{4-[4-(bromoacetyl)phenyl]isothiazol-3-yl}-N$^1$-(cyanomethyl)leucinamide (29 mg, 0.064 mmol) was dissolved in DMF (0.6 mL) and dimethylamine (0.13 mL of a 2 M solution in THF, 0.26 mmol) was added. The reaction mixture was stirred until disappearance of the starting material was observed by TLC (~1 h). Aqueous sat. NaHCO$_3$ was added, the product was extracted with EtOAc (3×), dried over MgSO$_4$, concentrated in vacuo and purified by flash chromatography with dichloromethane, methanol and ammonium hydroxide to yield N$^1$-(cyanomethyl)-N$^2$-{4-[4-(N,N-dimethylglycyl)phenyl]isothiazol-3-yl} leucinamide. MS (+ESI): 414.4 [M+1]$^+$.

Example 22

Synthesis of N-(Cyanomethyl)-3-(1-Methylcyclopropyl)-2-[(4'-Piperazin-1-yl-1,1'-Biphenyla-yl)thio] Propanamide To an ice cold solution of ethyl 4-methyl-4-pentenoate (1.11 g, 7.8 mmol) in 0.5 M diazomethane in Et$_2$O, was added palladium(II) acetate by portionwise addition (4 portions of 5 mg each were added in 15 min intervals). A total of 4 portions were added. The reaction mixture was filtered on a pad of celite and concentrated under 60 mm Hg with gentle warming. This crude product was treated a second time with diazomethane and palladium(II) acetate, filtered and concentrated. The resulting oil was filtered on a pad of florisil (60–100 mesh), washed with Et$_2$O (2×10 mL), concentrated under 60 mm Hg to give ethyl 3-(1-methylcyclopropyl)propanoate as a colorless oil.

Ethyl 3-(1-methylcyclopropyl)propanoate was converted to ethyl 2-bromo-3-(1-methylcyclopropyl)propanoate according to the literature procedure, Hernanz, D.; Camps, F.; Guerrero, A.; Delgado, A. *Tetrahedron Asymmetry* 1995, 6(9), 2291–2298.

To an ice cold solution of 4-bromothiophenol (455 mg, 2.4 mmol) in DRY (3 mL) was added sodium hydride (101 mg of 60% oil disp., 2.5 mmol). The resulting suspension was stirred at 0° C. for 30 min. A solution of ethyl 2-bromo-3-(1-methylcyclopropyl)propanoate (465 mg, 2.0 mmol) in DMF (2 mL) was added dropwise and the resulting mixture was stirred at room temperature for 2 hours. The reaction mixture was partitioned between EtOAc and water. The organic layer was dried over Na$_2$SO$_4$ and concentrated in vacuo. The crude product was purified by flash chromatography using Et$_2$O in hexane to afford ethyl 2-[(4-bromophenyl)thio]-3-(1-methylcyclopropyl)propanoate.

To an ice cold solution of ethyl 2-[(4-bromophenyl)thio]-3-(1-methylcyclopropyl)propanoate (457 mg, 1.3 mmol) in TBF (8 mL) and MeOH (3 mL) was added a 1.0 N aq. solution of LiOH (2 mL, 2.0 mmol) dropwise. The resulting mixture was stirred at room temperature for 18 h and partitioned between EtOAc and water+1.0 N HCl (5 mL). The organic layer was dried over Na$_2$SO$_4$ and concentrated in vacuo to give 2-[(4-bromophenyl)thio]-3-(1-methylcyclopropyl)propanoic acid.

To an ice cold solution of 2-[(4-bromophenyl)thio]-3-(1-methylcyclopropyl)propanoic acid (417 mg, 1.3 mmol), HATU (652 mg, 1.7 mmol), 2-aminoacetonitrile hydrochloride (171 mg, 1.8 mmol) in DMF (5 mL) was added N,N-diisopropylethylamine (0.68 mL, 3.9 mmol) dropwise. The resulting mixture was stirred at room temperature for 18 h and partitioned between EtOAc and water. The organic layer was dried over Na$_2$SO$_4$ and concentrated in vacuo. The crude product was purified by flash chromatography using EtOAc in hexane to afford 2-[(4-bromophenyl)thio]-N-(cyanomethyl)-3-(1-methylcyclopropyl)propanamide.

Using the procedure described in Example 1 where (2S)-2-(4-bromoanilino)-N-(cyanomethyl)-4-methylpentanamide is substituted for 2-[(4-bromophenyl)thio]-N-(cyanomethyl)-3-(1-methylcyclopropyl)propanamide, tert-butyl 4-[4'-({2-[(cyanomethyl)amino]-1-[(1-methylcyclopropyl) methyl]-2-oxoethyl}thio)-1,1'-biphenyl-4-yl]piperazine-1-carboxylate was obtained as a white solid.

Using the procedure described in Example 1 where tert-butyl 4-{4'-[((1S)-1-{[(cyanomethyl)amino]carbonyl}-3-methylbutyl)amino][1,1'-biphenyl]-4-yl}-1-piperazinecarboxylate is substituted for tert-butyl 4-[4'-({2-[(cyanomethyl)amino]-1-[(1-methylcyclopropyl)methyl]-2-oxoethyl}thio)-1,1'-biphenyl-4-yl]piperazine-1-carboxylate, N-(cyanomethyl)-3-(1-methylcyclopropyl)-2-[(4'-piperazin-1-yl-1,1'-biphenyl-4-yl)thio]propanamide was obtained after crystallization in EtOAc and hexane (1:2) as a beige solid. MS (+ESI): 435.2 [M+1]$^+$.

Example 23

Synthesis of N$^1$-(Cyanomethyl)-N$^2$-[3-Methyl-4-(4-Piperazin-1-ylphenyl)Isothiazol-5-yl]-L-Leucinamide To a solution of L-leucic acid (1.33 g, 10 mmol) in methanol (20 mL) was added 12 N HCl (0.2 mL, 2.4 mmol) and the solution was refluxed for 3 h. After cooling to room temperature, the reaction mixture was concentrated in vacuo. The crude product was purified by flash chromatography using EtOAc in hexane to afford methyl (2S)-2-hydroxy-4-methylpentanoate as a colorless oil.

To a solution of methyl (2S)-2-hydroxy-4-methylpentanoate (1.0 g, 6.8 mmol), triphenylphosphine (1.96 g, 7.5 mmol) and 4-nitrobenzoic acid (2.26 g, 13.5 mmol) in THF (14 mL) was added dropwise diethylazodicarboxylate over 30 min. The resulting mixture was stirred at room temperature for 18 h and partitioned between EtOAc and water. The organic layer was dried over Na$_2$SO$_4$ and concentrated in vacuo. The crude product was purified by flash chromatography using EtOAc in hexane to afford (1R)-1-(methoxycarbonyl)-3-methylbutyl 4-nitrobenzoate as a yellow oil.

To a solution of (1R)-1-(methoxycarbonyl)-3-methylbutyl 4-nitrobenzoate (1.59 g, 5.4 mmol) in methanol (15 mL) was added a freshly prepared solution of 1.5 M sodium methoxide in methanol (0.5 mL, 0.75 mmol). The resulting mixture was stirred at room temperature for 1 h, aqueous ammonium acetate (30 mL of 25% w/v) was added and the mixture was extracted with EtOAc. The organic layer was dried over Na$_2$SO$_4$ and concentrated in vacuo. The crude product was purified by flash chromatography using EtOAc in hexane to afford methyl (2R)-2-hydroxy-4-methylpentanoate as a colorless oil.

To a cold (−78° C.) solution of 5-amino-3-methylisothiazole hydrochloride (21.2 g, 127 mmol), pyridine (68 mL, 841 mmol) and DMAP (4.62 g, 38 mmol) in CH$_2$Cl$_2$ (420 mL) was slowly added trichloroethylchloroformate (31 mL, 224 mmol) over a period of 15 min. The reaction mixture was stirred at −78° C. for 30 min and then warmed to room temperature for 1 h. The mixture was partitioned between EtOAc and water, the organic layer was dried over MgSO$_4$ and concentrated in vacuo. The crude product was disolved in Et$_2$O (800 mL), charcoal was added and the resulting black suspension was boiled for 15 min and allowed to stand at room temperature for 18 h. The charcoal was removed by filtration on a pad of celite and the filtrate was concentrated in vacuo. The crude product was crystallized from a hot mixture of Et$_2$O/hexane (1:1, 600 mL) to yield 2,2,2-trichloroethyl 3-methylisothiazol-5-ylcarbamate as a light yellow solid.

To an ice cold solution of 2,2,2-trichloroethyl 3-methylisothiazol-5-ylcarbamate (20.6 g, 71.1 mmol), methyl (2R)-2-hydroxy-4-methylpentanoate (15.9 g, 109 mmol) and triphenylphosphine (28.9 g, 110 mmol) in DMF (260 mL) was slowly added over 15 min diisopropylazodicarboxylate (21.7 mL, 110 mmol). The resulting brown solution was stirred at room temperature for 30 min and then heated to 60° C. for 18 h. The reaction mixture was allowed to cool to room temperature and it was partitioned between EtOAc and water. The organic layer was dried over $Na_2SO_4$ and concentrated in vacuo. The crude product was purified twice by flash chromatography using EtOAc in hexane to afford methyl N-(3-methylisothiazol-5-yl)-N-[(2,2,2-trichloroethoxy)carbonyl]-L-leucinate as a yellow syrup.

To a solution of methyl N-(3-methylisothiazol-5-yl)-N-[(2,2,2-trichloroethoxy)carbonyl]-L-leucinate (28.5 g, 68 mmol) in $CH_2Cl_2$ (250 mL) and AcOH (125 mL) was added bromine (8.5 mL, 165 mmol). The resulting red solution was stirred at room temperature for 4 h. A further aliquot of bromine (8.5 mL, 165 mmol) was added and the resulting solution was stirred at room temperature for 18 h. The reaction mixture was partitioned between EtOAc and water+aqueous $NaHSO_3$ until the decolorization was complete. The organic layer was dried over $Na_2SO_4$ and concentrated in vacuo. The crude product was purified by flash chromatography using EtOAc in hexane to afford methyl N-(4-bromo-3-methylisothiazol-5-yl)-N-[(2,2,2-trichloroethoxy)carbonyl]-L-leucinate as a yellow syrup.

To a solution of methyl N-(4-bromo-3-methylisothiazol-5-yl)-N-[(2,2,2-trichloroethoxy)carbonyl]-L-leucinate (24.2 g, 48.8 mmol) in TBF (350 mL) and AcOH (90 mL) was added zinc dust (18.0 g, 275 mmol). The resulting grey suspension was sonicated for 30 min and then stirred at room temperature for 2 h. The reaction mixture was filtered on a pad of celite and concentrated in vacuo. The resulting residue was partitioned between EtOAc and water. The organic layer was dried over $Na_2SO_4$ and concentrated in vacuo. The crude product was purified by flash chromatography using $Et_2O$ in hexane to afford methyl N-(4-bromo-3-methylisothiazol-5-yl)-L-leucinate as a colorless oil which solidified upon standing for 1 h at room temperature under high vacuum to give a white solid.

To an ice cold solution of methyl N-(4-bromo-3-methylisothiazol-5-yl)-L-leucinate (11.7 g, 36.4 mmol) in methanol (300 mL) was slowly added over 10 min a 2.0 M aqueous lithium hydroxide solution (75 mL, 150 mmol). The resulting cloudy solution was stirred at room temperature for 3 hours. Most of the methanol was removed under reduced pressure and the resulting aqueous suspension was partitioned between EtOAc and water+90 ml of 10% HCl. The organic layer was washed once with water, dried over $Na_2SO_4$ and concentrated in vacuo to give N-(4-bromo-3-methylisothiazol-5-yl)-L-leucine as a white solid.

To an ice cold solution of N-(4-bromo-3-methylisothiazol-5-yl)-L-leucine (9.83 g, 32 mmol), PyBOP (18.6 g, 35.7 mmol) and 2-aminoacetonitrile hydrochloride (6.5 g, 70.3 mmol) in DMF (250 mL) was slowly added over 5 min triethylamine (15.6 mL, 112 mmol). The resulting suspension was stirred at room temperature for 18 h. The reaction mixture was partitioned between EtOAc and half-saturated $NaHCO_3$. The organic layer was washed once with water, dried over $Na_2SO_4$ and concentrated in vacuo. The crude product was purified by flash chromatography using EtOAc in hexane to give a colorless syrup. This syrup was disolved in $Et_2O$, washed once with 3% HCl and once with diluted $NaHCO_3$, dried over $Na_2SO_4$ and concentrated in vacuo to give $N^2$-(4-bromo-3-methylisothiazol-5-yl)-$N^1$-(cyanomethyl)-L-leucinamide as a white foam.

Using the procedure described in Example 1 where (2S)-2-(4-bromoanilino)-N-(cyanomethyl)-4-methylpentanamide is substituted for $N^2$-(4-bromo-3-methylisothiazol-5-yl)-N'-(cyanomethyl)-L-leucinamide, tert-butyl (4-{5-[((1S)-1-{[(cyanomethyl)amino]carbonyl}-3-methylbutyl)amino]-3-methylisothiazol-4-yl}phenyl)-1-piperazinecarboxylate was obtained as a colorless gum.

Using the procedure described in Example 1 where tert-butyl 4-{4'-[((1S)-1-{[(cyanomethyl)amino]carbonyl}-3-methylbutyl)amino][1,1'-biphenyl]-4-yl}-1-piperazinecarboxylate was substituted for tert-butyl ({5-[(1(S)-1-{[(cyanomethyl)amino]carbonyl}-3-methylbutyl)amino]-3-methylisothiazol-4-yl}phenyl)-1-piperazinecarboxylate, N-(cyanomethyl)-$N^2$-[3-methyl-4-(4-piperazin-1-ylphenyl) isothiazol-5-yl]-L-leucinamide was obtained as a white foam. MS (+ESI): 427.2 $[M+1]^+$.

Example 24

Synthesis of N-(Cyanomethyl)-$N^2$-(4-{4-[4-(2-Hydroxyethyl)Piperazin-1-yl]Phenyl}-3-Methylisothazol-5-yl)-L-Leucinamide A solution of $N^1$-(cyanomethyl)-$N^2$-[3-methyl-4-(4-piperazin-1-ylphenyl)isothiazol-5-yl]-L-leucinamide (113 mg, 0.26 mmol, prepared as described in Example 23), 2-bromoethanol (32 µL, 0.45 mmol) and triethylamine (64 µL, 0.64 mmol) in $CH_3CN$ (1.0 mL) was heated at 85° C. for 9 h. The reaction mixture was allowed to cool to room temperature and it was partitioned between EtOAc and water. The organic layer was dried over $Na_2SO_4$ and concentrated in vacuo. The crude product was purified by flash chromatography using MeOH in $CH_2Cl_2$ to afford the title compound as a beige foam. MS (+ESI): 471.2 $[M+1]^+$.

Example 25

Synthesis of N-(Cyanomethyl)-1-[4'-(1-Piperazinyl) [1,1'-Biphenyl]-3-yl]-2-Piperidinecarboxamide A mixture of pipecolic acid (1.55 g, 12.0 mmol), 1,3-dibromobenzene (1.6 mL, 13.2 mmol), CuI (0.56 g, 2.9 mmol) and $K_2CO_3$ (3.0 g, 21.7 mmol) in 14 mL of DMA was degassed, then heated to 95° C. for 23 h. The mixture was cooled and partitioned between ether and water. The organic layer was extracted with 1 M NaOH, and the combined aqueous layers were acidified with 6N HCl and extracted with EtOAc. The organic phase was washed with brine, dried over $MgSO_4$ and concentrated to give 3 g of an oil. This material was combined with HATU (2.1 g, 5.5 mmol) and aminoacetonitrile hydrochloride (0.85 g, 9.2 mmol) in DMF (3 mL), then treated with $Et_3N$ (2.0 mL, 14 mmol). The mixture was stirred for 30 min and then partitioned between ethyl acetate and water. The organic phase was washed with 1 M NaOH, 1 M HCl (3×) and brine, then dried over $MgSO_4$ and concentrated. Purification by flash chromatography (40% EtOAc/hexanes) gave 1-(3-bromophenyl)-N-(cyanomethyl)-2-piperidinecarboxamide.

A mixture of 1-(3-bromophenyl)-N-(cyanomethyl)-2-piperidinecarboxamide (209 mg, 0.65 mmol), 4-[4-(tert-butoxycarbonyl)-1-piperazinyl]phenylboronic acid (219 mg, 0.71 mmol), and $PdCl_2(dppf)$ (41 mg, 0.05 mmol) in DMF (4 mL) was heated to 60° C. 2N $Na_2CO_3$ (0.65 mL, 1.3 mmol) was added dropwise, and the mixture was heated to 85° C. overnight. The mixture was cooled and partitioned between water and ethyl acetate. The organic layer was washed with 1 M NaOH and brine, then dried over $MgSO_4$ and concentrated. Purification by flash chromatography (50% EtOAc/hexanes) gave tert-butyl 4-[3'-(2-{[(cyanomethyl)amino]carbonyl}-1-piperidinyl)[1,1'-biphenyl]-4-yl]-1-piperazinecarboxylate.

To a solution of tert-butyl 4-[3'-(2-{[(cyanomethyl)amino]carbonyl}-1-piperidinyl)[1,1'-biphenyl]-4-yl]-1-piperazinecarboxylate (249 mg, 0.51 mmol) in dioxane (5 mL) was added methanesulfonic acid (0.1 mL, 1.5 mmol). The mixture was stirred overnight, then partitioned between EtOAc and 1 M NaOH. The organic phase was washed with brine and dried over $MgSO_4$. Purification by flash chromatography (5% MeOH/dichloromethane with 0.5% $NH_4OH$) gave N-(cyanomethyl)-1-[4'-(1-piperazinyl)[1,1'-biphenyl]-3-yl]-2-piperidinecarboxamide.

MS (+APCI) m/z 404 (M+1, 100), 320 (15).

Example 26

Synthesis of 1-(4-Chloro-1,1'-Biphenyl-3-yl)-N-(Cyanomethyl)Piperidine-2-Carboxamide To a suspension of 1-(3-bromophenyl)-N-(cyanomethyl)-2-piperidinecarboxamide (2.25 g, 6.98 mmol, prepared as described in example 25) in 70 mL of isopropyl alcohol was added N-chlorosuccinimide (1.02 g, 7.68 mmol). The suspension was heated to 60° C. and the resultant solution was stirred at 60° C. for 2 h. The mixture was cooled and partitioned between ethyl acetate and brine. The aqueous layer was extracted with ethyl acetate (3 ×) and the combined organic layers were dried over $Na_2SO_4$ and concentrated. Purification by flash chromatography (50% $Et_2O$/hexanes) yielded 1-(5-bromo-2-chlorophenyl)-N-(cyanomethyl)piperidine-2-carboxamide (faster eluting compound) and 1-(3-bromo-4-chlorophenyl)-N-(cyanomethyl)piperidine-2-carboxamide (slower eluting compound).

A mixture of 1-(5-bromo-2-chlorophenyl)-N-(cyanomethyl)piperidine-2-carboxamide (125 mg, 0.35 mmol), phenylboronic acid (64 mg, 0.53 mmol), $PdCl_2(dppf)$ (29 mg, 0.035 mmol) and 2 N $Na_2CO_3$ (0.5 mL, 1.1 mmol) in DMF (3.5 mL) was degassed and then heated to 110° C. for 4 h. The mixture was cooled and partitioned between water and ethyl acetate. The aqueous layer was extracted with ethyl acetate (3×) and the combined organic layers were dried over $Na_2SO_4$ and concentrated. Purification by flash chromatography (50% $Et_2O$/hexanes) afforded 1-(4-chloro-1,1'-biphenyl-3-yl)-N-(cyanomethyl)piperidine-2-carboxamide.

MS (+ESI): 354.1 [M+1]$^+$

Example 27

Synthesis of (4S)-1-(4-Chloro-4'-Piperazin-1-yl-1,1'-Biphenyl-3-yl)-N-(Cyanomethyl)-4-Methyl-L-Prolinamide To di(tert-butyl) (2S,4S)-4-methylpyrrolidine-1,2-dicarboxylate (Ref: *J. Amer. Chem. Soc.*, 1996, 118, 36, 8700–8706, 2.4 g, 8.42 mmol) in $CH_2Cl_2$ (15 mL) was added TFA (15 mL) and the reaction was stirred for 2 hours. The reaction was concentrated in vacuo and re-dissolved in $CH_2Cl_2$ (15 mL), TFA (15 mL) was added and the reaction was stirred for 1 hour. The reaction was concentrated in vacuo to afford (4S)-4-methyl-L-proline trifluoroacetate and used directly in the next step.

To (4S)-4-methyl-L-proline trifluoroacetate (2.92 g, 8.17 mmol), 1,4-dibromobenzene (2.9 g, 12.27 mmol), potassium carbonate (3.95 g, 28.6 mmol), and copper iodide (315 mg, 1.64 mmol) was added dry DMF (30 mL) under dry nitrogen. The reaction flask was thoroughly degassed with dry nitrogen and heated at 95° C. for 3 days. Water and hexane were added and the organic phase was separated and discarded (to remove excess 1,4-dibromobenzene). The pH of the aqueous phase was adjusted to 3 with aqueous 10% HCl and the product extracted with EtOAc (2×), dried over $Na_2SO_4$, concentrated in vacuo and purified by flash chromatography over silica gel (AcOH/EtOAc/Hex, 0.5/49.5/50) to afford (4S)-1-(3-bromophenyl)-4-methyl-L-proline.

To (4S)-1-(3-bromophenyl)-4-methyl-L-proline (1.35 g, 4.75 mmol), PyBOP (2.72 g, 5.23 mmol), aminoacetonitrile hydrochloride (968 mg, 10.46 mmol) in dry DMW (30 mL) under dry nitrogen was added triethylamine (2.35 mL, 16.63 mmol) dropwise and the reaction was stirred overnight. Aqueous sat. $NaHCO_3$ was added and the product extracted with $Et_2O$ (2×), dried over $Na_2SO_4$, concentrated in vacuo and purified by flash chromatography over silica gel (EtOAc/Hex, 35/75, then 4/6) to afford (4S)-1-(3-bromophenyl)-N-(cyanomethyl)-4-methyl-L-prolinamide.

To a hot (60° C.) solution of (4S)-1-(3-bromophenyl)-N-(cyanomethyl)-4-methyl-L-prolinamide (630 mg, 1.96 mmol) in isopropyl alcohol (20 mL) was added N-chlorosuccinimide and the reaction mixture was stirred at 60° C. for 2 hours. The reaction was concentrated in vacuo and the product purified by flash chromatography over silica gel (MTBE/Hex, 1/1, then 6/4, then 8/2) to afford (4S)-1-(5-bromo-2-chlorophenyl)-N-(cyanomethyl)-4-methyl-L-prolinamide.

To (4S)-1-(5-bromo-2-chlorophenyl)-N-(cyanomethyl)-4-methyl-L-prolinamide (40 mg, 0.112 mmol),4-[4-(tert-butoxycarbonyl)-1-piperazinyl]phenylboronic acid (42 mg, 0.135 mmol, prepared as described in Example 1) and catalyst $PdCl_2(dppf)$ (5 mg, 0.0034 mmol) in DMF (2 mL) under dry nitrogen was added aqueous sodium carbonate (2.0 M, 0.17 mL, 0.336 mmol). The reaction was heated to 95° C. for 1 hour and an additional aliquot of $PdCl_2(dppf)$ (365 mg, 0.45 mmol) was added and the reaction mixture was heated for 3 hours. Water was added and the product extracted with ether (3×), dried over $Na_2SO_4$, concentrated in vacuo and purified by flash chromatography over silica gel (EtOAc/Hex, 4/6) to afford (4S)-1-{4'-[4-(tert-butoxycarbonyl)piperazin-1-yl]-4-chloro-1,1'-biphenyl-3-yl}-N-(cyanomethyl)-4-methyl-L-prolinamide.

To (4S)-1-{4'-[4-(tert-butoxycarbonyl)piperazin-1-yl]-4-chloro-1,1'-biphenyl-3-yl}-N-(cyanomethyl)-4-methyl-L-prolinamide (66 mg, 0.123 mmol) in dry TBF (0.25 mL) under dry nitrogen was gradually added a total of 3 equivalents of $MeSO_3H$ (30 mL, 0.39 mmol) over a period of 1 hour in portions of 1–2 equivalents at a time and the reaction mixture was stirred overnight. Aqueous sat. $NaHCO_3$ was added carefully and the product was extracted with EtOAc (2×), dried over $Na_2SO_4$, concentrated in vacuo and purified by flash chromatography over silica gel (HOH/MeOH/$CH_2Cl_2$, 1/9/90) to afford (4S)-1-(4-chloro-4'-piperazin-1-yl-1,1'-biphenyl-3-yl)-N-(cyanomethyl)-4-methyl-L-prolinamide. MS (-APCI): 436.2 [M−1]$^-$.

Using similar experimental procedures as described above, the following compounds were synthesized.

| NAME | CHARACTERIZATION |
| --- | --- |
| $N^1$-(cyanomethyl)-$N^2$-{4-[4-(4-methylpiperazin-1-yl)phenyl]thien-3-yl}-L-leucinamide | MS (+APCI): 426.2 [M + 1]$^+$ |
| (4S)-1-(3-bromophenyl)-N-(cyanomethyl)-4-methyl-L-prolinamide | MS (+ESI): 322.1/324.2 [M + 1]+ |

-continued

| NAME | CHARACTERIZATION |
|---|---|
| (4S)-N-(cyanomethyl)-4-methyl-1-(4'-piperazin-1-yl-1,1'-biphenyl-3-yl)-L-prolinamide | MS (+APCI): 404.4 [M + 1]+ |
| (4S)-N-(1-cyanocyclopropyl)-4-methyl-1-(4'-piperazin-1-yl-1,1'-biphenyl-3-yl)-L-prolinamide | MS (+APCI): 430.3 [M + 1]+ |
| $N^1$-(cyanomethyl)-$N^2$-[4-(4-piperazin-1-ylphenyl)isothiazol-3-yl]-L-leucinamide | MS (+ESI): 413.2 [M + 1]+ |
| $N^1$-(cyanomethyl)-$N^2$-(4-{4-[(dimethylamino)methyl]phenyl}thien-3-yl)-L-leucinamide | MS (+ESI): 385.3 [M + 1]+ |
| $N^1$(cyanomethyl)-$N^2$-[4-(4-{[(2-hydroxyethyl)amino]methyl}phenyl)thien-3-yl]-L-leucinamide | MS (+ESI): 401.5 [M + 1]+ |
| $N^1$-(cyanomethyl)-$N^2$-{4-[4-(morpholin-4-ylmethyl)phenyl]thien-3-yl}-L-leucinamide | MS (+ESI): 427.2 [M + 1]+ |
| $N^2$-(4-{4-[(benzylamino)methyl]phenyl}thien-3-yl)-$N^1$-(cyanomethyl)-L-leucinamide | MS (+ESI): 447.1 [M + 1]+ |
| $N^2$-[4-(4-tert-butylphenyl)thien-3-yl]-$N^1$-(cyanomethyl)-L-leucinamide | MS (+APCI): 384.2 [M + 1]+ |
| $N^1$-(cyanomethyl)-$N^2$-[4-(4-isopropylphenyl)thien-3-yl]-L-leucinamide | MS (+APCI): 370.1 [M + 1]+ |
| $N^1$-(cyanomethyl)-$N^2$-[3-(4-piperazin-1-ylphenyl)isoxazol-4-yl]leucinamide | MS (+ESI): 397.4 [M + 1]+ |
| $N^1$-(cyanomethyl)-$N^2$-[3-(4-piperazin-1-ylphenyl)isoxazol-4-yl]-L-leucinamide | [a]D = +23 (c 1.95, CH2Cl2) |
| $N^1$-(cyanomethyl)-$N^2$-[3-(4-piperazin-1-ylphenyl)isoxazol-4-yl]-D-leucinamide | [a]D = −16 (c 1.93, CH2Cl2) |
| $N^1$-(cyanomethyl)-$N^2$-(4-{4-[2-(dimethylamino)ethyl]phenyl}thien-3-yl)-L-leucinamide | see experimental |
| $N^1$-(1-cyanocyclopropyl)-$N^2$-[3-(4-piperazin-1-ylphenyl)isoxazol-4-yl]-L-leucinamide | MS (+ESI): 423.3 [M + 1]+ |
| $N^1$-(cyanomethyl)-$N^2$-{3-[4-(4-isopropylpiperazin-1-yl)phenyl]isoxazol-4-yl}-L-leucinamide | MS (+ESI): 439.4 [M + 1]+ |
| $N^2$-[4-(3-bromo-4-piperazin-1-ylphenyl)-3-methylisothiazol-5-yl]-$N^1$-(cyanomethyl)leucinamide | MS (+ESI): 505.3/507.3 [M + 1]+ |
| $N^1$-(cyanomethyl)-$N^2$-{4-[4-(4-isopropylpiperazin-1-yl)phenyl]isothiazol-3-yl}-L-leucinamide | MS (+ESI): 455.3 [M + 1]+ |
| $N^2$-[4-(3-bromo-4-piperazin-1-ylphenyl)isothiazol-3-yl]-$N^1$-(cyanomethyl)-L-leucinamide | MS (+ESI): 491.4/493.1 [M + 1]+ |
| $N^2$-[4-(4-bromophenyl)isothiazol-3-yl]-$N^1$-(cyanomethyl)-L-leucinamide | MS (+ESI): 407.1/409.2 [M + 1]+ |
| $N^1$-(cyanomethyl)-$N^2$-(1-phenyl-1H-tetraazol-5-yl)-L-leucinamide | MS (+APCI): 313.9 [M + 1]+ |
| $N^1$-(cyanomethyl)-$N^2$-(1-phenyl-1H-tetraazol-5-yl)-L-leucinamide | MS (+APCI): 491.1 [M + 1]+ |
| $N^1$-(cyanomethyl)-$N^2$-[4-(4-iodophenyl)-3-methylisothiazol-5-yl]-L-leucinamide | MS (+ESI): 469.1 [M + 1]+ |
| $N^1$-(cyanomethyl)-$N^2$-(3-methyl-4-phenylisothiazol-5-yl)-L-leucinamide | MS (+APCI): 343.0 [M + 1]+ |
| $N^2$-[4-(1,1'-biphenyl-4-yl)-3-methylisothiazol-5-yl]-$N^1$-(cyanomethyl)-L-leucinamide | MS (+APCI): 419.1 [M + 1]+ |
| (4S)-1-(1,1'-biphenyl-3-yl)-N-(cyanomethyl)-4-methyl-L-prolinamide | MS (+ESI): 320.2 [M + 1]+ |
| (4S)-1-(4-chloro-1,1'-biphenyl-3-yl)-N-(cyanomethyl)-4-methyl-L-prolinamide | MS (+ESI): 354.2/356.2 [M + 1]+ |
| (4S)-N-(cyanomethyl)-1-[3-(3,3-dimethylbut-1-ynyl)phenyl]-4-methyl-L-prolinamide | MS (+APCI): 324.1 [M + 1]+ |
| (4S)-N-(cyanomethyl)-1-[3-(3-hydroxy-3-methylbut-1-ynyl)phenyl]-4-methyl-L-prolinamide | MS (+APCI): 326 [M + 1]+ |
| N-(cyanomethyl)-1-(1-phenyl-1H-tetraazol-5-yl)piperidine-2-carboxamide | MS (+APCI): 312.0 [M + 1]+ |
| (4S)-1-(5-bromo-2-chlorophenyl)-N-(cyanomethyl)-4-methyl-L-prolinamide | MS (+ESI): 356.0/358.0/360.0 [M + 1]+ |
| (4S)-1-(3-bromo-4-chlorophenyl)-N-(cyanomethyl)-4-methyl-L-prolinamide | MS (+ESI): 356.0/358.0/360.0 [M + 1]+ |
| (4S)-1-(6-chloro-1,1'-biphenyl-3-yl)-N-(cyanomethyl)-4-methyl-L-prolinamide | MS (+ESI): 354.2 [M + 1]+ |
| $N^1$-(cyanomethyl)-$N^2$-[4-(4-piperazin-1-ylphenyl)isothiazol-5-yl]leucinamide | MS (+ESI): 413.2 [M + 1]+ |
| $N^1$-(cyanomethyl)-$N^2$-[3-methyl-4-(4-pyridin-3-ylphenyl)isothiazol-5-yl]-L-leucinamide | MS (+APCI): 420.1 [M + 1]+ |
| $N^1$-(cyanomethyl)-$N^2$-[3-methyl-4-(4-pyridin-4-ylphenyl)isothiazol-5-yl]-L-leucinamide | MS (+APCI): 420.1 [M + 1]+ |
| $N^1$-(cyanomethyl)-$N^2$-{3-methyl-4-[4-(1-trityl-1H-imidazol-5-yl)phenyl]isothiazol-5-yl}-L-leucinamide | MS (+ESI) 651.2 [M + 1]+ |
| $N^1$-(cyanomethyl)-$N^2$-{4-[4-(1H-imidazol-5-yl)phenyl]-3-methylisothiazol-5-yl}-L-leucinamide | MS (+ESI) 409.3 [M + 1]+ |
| $N^1$-(cyanomethyl)-$N^2$-{3-methyl-4-[4-(1-trityl-1H-imidazol-2-yl)phenyl]isothiazol-5-yl}-L-leucinamide | MS (+ESI) 651.2 [M + 1]+ |
| $N^1$-(cyanomethyl)-$N^2$-[4-(4-hydroxyphenyl)-3-methylisothiazol-5-yl]-L-leucinamide | MS (+ESI) 359.0 [M + 1]+ |
| $N^1$-(cyanomethyl)-$N^2$-{3-methyl-4-[4-(1-oxidopyridin-4-yl)phenyl]isothiazol-5-yl}-L-leucinamide | MS (+ESI) 436.1 [M + 1]+ |
| 2-{[4'-(aminomethyl)-1,1'-biphenyl-4-yl]thio}-N-(cyanomethyl)-4-methylpentanamide | MS (+ESI): 368.2 [M + 1]+ |
| 2-(1,1'-biphenyl-4-ylthio)-N-(cyanomethyl)-4-methylpentanamide | MS (+APCI): 339.3 [M + 1]+ |
| N-(cyanomethyl)-2-{[4'-(hydroxymethyl)-1,1'-biphenyl-4-yl]thio}-4-methylpentanamide | MS (+APCI): 369.0 [M + 1]+ |
| N-(cyanomethyl)-4-methyl-2-[(4'-piperidin-1-yl-1,1'-biphenyl-4-yl)thio]pentanamide | MS (+APCI): 422.2 [M + 1]+ |
| 2-({4'-[(benzylamino)methyl]-1,1'-biphenyl-4-yl}thio)-N-(cyanomethyl)-4-methylpentanamide | MS (+APCI): 458.3 [M + 1]+ |
| N-(cyanomethyl)-2-({4'-[(cyclopropylamino)methyl]-1,1'-biphenyl-4-yl}thio)-4-methylpentanamide | MS (+APCI): 408.4 [M + 1]+ |
| N-(cyanomethyl)-4-methyl-2-[(4'-{[(1-methylpiperidin-4-yl)amino]methyl}-1,1'-biphenyl-4-yl)thio]pentanamide | MS (+APCI): 465.3 [M + 1]+ |
| N-(cyanomethyl)-2-({4'-[(dicyclobutylamino)methyl]-1,1'-biphenyl-4-yl}thio)-4-methylpentanamide | MS (+APCI): 476.2 [M + 1]+ |
| N-(cyanomethyl)-2-({4'-[(dicyclopentylamino)methyl]-1,1'-biphenyl-4-yl}thio)-4-methylpentanamide | MS (+APCI): 504.3 [M + 1]+ |
| N-(cyanomethyl)-2-({4'-[(cyclopentylamino)methyl]-1,1'-biphenyl-4-yl}thio)-4-methylpentanamide | MS (+APCI): 436.3 [M + 1]+ |
| N-(cyanomethyl)-4-methyl-2-[(4-piperazin-1-ylphenyl)thio]pentanamide | MS (+APCI): 347.1 [M + 1]+ |
| N-(cyanomethyl)-2-[(3',5'-difluoro-1,1'-biphenyl-4-yl)thio]-4-methylpentanamide | MS (−ESI): 373.3 [M − 1]− |
| 2-{[4-(5-chlorothien-2-yl)phenyl]thio}-N-(cyanomethyl)-4-methylpentanamide | MS (−ESI): 376.9 [M − 1]− |
| N-(cyanomethyl)-4-methyl-2-{[4'-(trifluoromethyl)-1,1'-biphenyl-4-yl]thio}pentanamide | MS (−ESI): 405.3 [M − 1]− |
| N-(cyanomethyl)-4-methyl-2-[(3'-methyl-1,1'-biphenyl-4-yl)thio]pentanamide | MS (−ESI): 351.6 [M − 1]− |
| N-(cyanomethyl)-4-methyl-2-[(4-quinolin-5-ylphenyl)thio]pentanamide | MS (−APCI): 388.3 [M − 1]− |
| 2-{[4-(1-benzothien-3-yl)phenyl]thio}-N-(cyanomethyl)-4-methylpentanamide | MS (−ESI): 393.3 [M − 1]− |
| N-(cyanomethyl)-4-methyl-2-[(4-quinolin-8-ylphenyl)thio]pentanamide | MS (−APCI): 388.3 [M − 1]− |
| 2-[(4'-cyano-1,1'-biphenyl-4-yl)thio]-N-(cyanomethyl)-4-methylpentanamide | MS (−APCI): 362.2 [M − 1]− |
| N-(cyanomethyl)-4-methyl-2-{[4-(1H-pyrazol-3-yl)phenyl]thio}pentanamide | MS (−ESI): 327.1 [M − 1]− |
| N-(cyanomethyl)-2-[(5'-fluoro-2'-methoxy- | MS (−ESI): 385.1 |

| NAME | CHARACTERIZATION |
|---|---|
| 1,1'-biphenyl-4-yl)thio]-4-methylpentanamide | [M − 1]− |
| 2-{[4-(1-benzothien-7-yl)phenyl]thio}-N-(cyanomethyl)-4-methylpentanamide | MS (−ESI): 392.9 [M − 1]− |
| N-(cyanomethyl)-4-methyl-2-[(4-quinolin-6-ylphenyl)thio]pentanamide | MS (−ESI): 388.1 [M − 1]− |
| N-(cyanomethyl)-2-[(3'-fluoro-4'-piperazin-1-yl-1,1'-biphenyl-4-yl)thio]-4-methylpentanamide | MS (+ESI): 441.4 [M + 1]+ |
| N-(cyanomethyl)-2-{[4'-(4-ethylpiperazin-1-yl)-1,1'-biphenyl-4-yl]thio}-4-methylpentanamide | MS (+ESI): 451.3 [M + 1]+ |
| N-(cyanomethyl)-2-[(3'-ethyl-4'-piperazin-1-yl-1,1'-biphenyl-4-yl)thio]-4-methylpentanamide | MS (+ESI): 451.3 [M + 1]+ |
| N-(cyanomethyl)-4-methyl-2-[(4-{2-[(4-propylpiperazin-1-yl)carbonyl]-1H-indol-5-yl}phenyl)thio]pentanamide | MS (+APCI): 532.3 [M + 1]+ |
| N-(cyanomethyl)-4-methyl-2-[(4-{2-[(4-methylpiperazin-1-yl)carbonyl]-1H-indol-5-yl}phenyl)thio]pentanamide | MS (+ESI): 504.4 [M + 1]+ |
| N-(cyanomethyl)-4-methyl-2-({4-[2-(piperazin-1-ylcarbonyl)-1H-indol-5-yl]phenyl}thio)pentanamide | MS (+ESI): 490.3 [M + 1]+ |
| N-(cyanomethyl)-2-{[4'-(4-methoxypiperidin-4-yl)-1,1'-biphenyl-4-yl]thio}-4-methylpentanamide | MS (+ESI): 420.3 [M + 1]+ |
| N-(cyanomethyl)-4-methyl-2-{[4-(2-piperazin-1-ylpyrimidin-5-yl)phenyl]thio}pentanamide | MS (+ESI): 425.6 [M + 1]+ |
| N-(cyanomethyl)-4-methyl-2-{[4'-piperazin-1-yl-2'-(trifluoromethyl)-1,1'-biphenyl-4-yl]thio}pentanamide | MS (+ESI): 491.2 [M + 1]+ |
| N1-(cyanomethyl)-N2-[4-(2-piperazin-1-ylpyrimidin-5-yl)isothiazol-3-yl]-L-leucinamide | MS (+ESI): 415.1 [M + 1]+ |
| N1-(cyanomethyl)-N2-{4-[4-piperazin-1-yl-2-(trifluoromethyl)phenyl]isothiazol-3-yl}-L-leucinamide | MS (+ESI): 481.2 [M + 1]+ |
| N-(cyanomethyl)-1-{[4'-(4-ethylpiperazin-1-yl)-1,1'-biphenyl-4-yl]thio}cyclohexanecarboxamide | MS (+ESI): 463.2 [M + 1]+ |
| N-(cyanomethyl)-2-{[4'-(2,6-dimethylpiperazin-1-yl)-1,1'-biphenyl-4-yl]thio}-4-methylpentanamide | MS (+ESI): 451.2 [M + 1]+ |
| N-(cyanomethyl)-2-({4-[5-(2-hydroxyethyl)-4-methyl-1,3-thiazol-2-yl]phenyl}thio)-4-methylpentanamide | MS (+ESI): 404.5 [M + 1]+ |
| N1-(cyanomethyl)-N2-{4-[4-(1,4-diazepan-1-yl)phenyl]isothiazol-3-yl}-L-leucinamide | MS (+ESI): 427.2 [M + 1]+ |
| N1-(cyanomethyl)-N2-{4-[4-(3,5-dimethylpiperazin-1-yl)phenyl]isothiazol-3-yl}-L-leucinamide | MS (+ESI): 441.7 [M + 1]+ |
| N1-(cyanomethyl)-N2-{4-[4-(N,N-dimethylglycyl)phenyl]isothiazol-3-yl}-L-leucinamide | MS (+ESI): 414.4 [M + 1]+ |
| N1-(cyanomethyl)-N2-(4-{4-[(2,6-dimethylpiperidin-1-yl)acetyl]phenyl}isothiazol-3-yl)-L-leucinamide | MS (+ESI): 482.3 [M + 1]+ |
| N1-(cyanomethyl)-N2-{4-[4-(N,N-dimethylglycyl)phenyl]-3-methylisothiazol-5-yl}-L-leucinamide | MS (+ESI): 428.2 [M + 1]+ |
| N2-{4-[4-(1-amino-1-methylethyl)phenyl]isothiazol-3-yl}-N1-(cyanomethyl)-L-leucinamide | MS (+ESI): 386.2 [M + 1]+ |
| N2-[4-(4-acetylphenyl)-3-methylisothiazol-5-yl]-N1-(cyanomethyl)-L-leucinamide | MS (+ESI): 385.2 [M + 1]+ |
| N2-(4-{4-[(tert-butylamino)sulfonyl]phenyl}-3-methylisothiazol-5-yl)-N1-(cyanomethyl)-L-leucinamide | MS (+ESI): 478.3 [M + 1]+ |
| N1-(cyanomethyl)-N2-{3-methyl-4-[4-(piperazin-1-ylsulfonyl)phenyl]isothiazol-5-yl}-L-leucinamide | MS (+ESI): 491.3 [M + 1]+ |
| N1-(cyanomethyl)-N2-{3-methyl-4-[4-(methylsulfonyl)phenyl]isothiazol-5-yl}-L-leucinamide | MS (+ESI): 421.5 [M + 1]+ |
| N2-{4-[4-(aminosulfonyl)phenyl]-3-methylisothiazol-5-yl}-N1-(cyanomethyl)-L-leucinamide | MS (+ESI): 422.4 [M + 1]+ |
| N1-(cyanomethyl)-N2-[4-(2-fluoro-4-piperazin-1-ylphenyl)-3-methylisothiazol-5-yl]-L-leucinamide | MS (+ESI): 445.1 [M + 1]+ |
| 2-[(4'-acetyl-1,1'-biphenyl-4-yl)thio]-N-(cyanomethyl)-4-methylpentanamide | MS (−APCI): 379.2 [M − 1]− |
| N-(cyanomethyl)-3-(1-methylcyclopropyl)-2-[(4'-piperazin-1-yl-1,1'-biphenyl-4-yl)thio]propanamide | MS (+ESI): 435.2 [M + 1]+ |
| N1-(cyanomethyl)-N2-[4-(3-fluoro-4-piperazin-1-ylphenyl)thien-3-yl]-L-leucinamide | MS (+ESI): 430.1 [M + 1]+ |
| N1-(cyanomethyl)-N2-{4-[3-(hydroxymethyl)phenyl]thien-3-yl}-L-leucinamide | MS (+ESI): 358.5 [M + 1]+ |
| N2-(2-bromo-4-{3-[(dimethylamino)methyl]phenyl}thien-3-yl)-N1-(cyanomethyl)-L-leucinamide | MS (+ESI): 463.0, 465.1 [M + 1]+ |
| N1-(cyanomethyl)-N2-(4-{3-[(dimethylamino)methyl]phenyl}thien-3-yl)-L-leucinamide | MS (+ESI): 385.5 [M + 1]+ |
| N1-(cyanomethyl)-N2-{4-[3-fluoro-4-(hydroxymethyl)phenyl]thien-3-yl}-L-leucinamide | MS (+ESI): 376.4 [M + 1]+, 358.3 [M − OH]+ |
| N1-(cyanomethyl)-N2-{4-[4-(4-hydroxypiperidin-4-yl)phenyl]thien-3-yl}-L-leucinamide | MS (+ESI): 427.4 [M + 1]+, 409.5 [M − OH]+ |
| N1-(cyanomethyl)-N2-(4-{4-[(dimethylamino)methyl]-3-fluorophenyl}thien-3-yl)-L-leucinamide | MS (+ESI): 403.4 [M + 1]+ |
| 4-(4-{4-[1-(Cyanomethyl-carbamoyl)-3-methyl-butylamino]-thiophen-3-yl}-2-fluoro-benzyl)-piperazine-1-carboxylic acid tert-butyl ester | MS (+ESI): 544.1 [M + 1]+ |
| N1-(cyanomethyl)-N2-{4-[3-fluoro-4-(piperazin-1-ylmethyl)phenyl]thien-3-yl}-L-leucinamide | MS (+ESI): 444.4 [M + 1]+ |
| N1-(cyanomethyl)-N2-{4-[4-(pyrrolidin-1-ylmethyl)phenyl]thien-3-yl}-L-leucinamide | MS (+ESI): 411.7 [M + 1]+ |
| N1-(cyanomethyl)-N2-[3-methyl-4-(4-piperazin-1-ylphenyl)isothiazol-5-yl]-L-leucinamide | MS (+ESI): 427.2 [M + 1]+ |
| N1-(cyanomethyl)-N2-{4-[4-(4-isopropylpiperazin-1-yl)phenyl]-3-methylisothiazol-5-yl}-L-leucinamide | MS (+ESI): 469.3 [M + 1]+ |
| 6-{5-[1-(Cyanomethyl-carbamoyl)-3-methyl-butylamino]-3-methyl-isothiazol-4-yl}-napthalene-2-carboxylic acid methyl ester | MS (+ESI): 451.3 [M + 1]+ |
| N1-(cyanomethyl)-N2-(3-methyl-4-{4-[4-(2,2,2-trifluoroethyl)piperazin-1-yl]phenyl}isothiazol-5-yl)-L-leucinamide | MS (+ESI): 509.2 [M + 1]+ |
| N1-(cyanomethyl)-N2-{3-methyl-4-[4-(4-propylpiperazin-1-yl)phenyl]isothiazol-5-yl}-L-leucinamide | MS (+ESI): 469.3 [M + 1]+ |
| N2-{4-[4-(4-acetylpiperazin-1-yl)phenyl]-3-methylisothiazol-5-yl}-N1-(cyanomethyl)-L-leucinamide | MS (+ESI): 469.1 [M + 1]+ |
| N1-(cyanomethyl)-N2-{3-methyl-4-[4-(4-(methylsulfonyl)piperazin-1-yl]phenyl}isothiazol-5-yl)-L-leucinamide | MS (+ESI): 505.1 [M + 1]+ |
| N2-{4-[4-(4-tert-butylpiperazin-1-yl)phenyl]-3-methylisothiazol-5-yl}-N1-(cyanomethyl)-L-leucinamide | MS (+ESI): 483.3 [M + 1]+, 427.3 [M − t-Bu]+ |
| N1-(cyanomethyl)-N2-(4-{4-[(1S,4S)-2,5-diazabicyclo[2.2.1]hept-2-yl]phenyl}-3-methylisothiazol-5-yl)-L-leucinamide | MS (+ESI): 439.3 [M + 1]+ |
| N1-(cyanomethyl)-N2-{4-[6-(hydroxymethyl)-2-naphthyl]-3-methylisothiazol-5-yl}-L-leucinamide | MS (+ESI): 423.1 [M + 1]+ |
| N1-(cyanomethyl)-N2-(4-{4-[4-(2-hydroxyethyl)piperazin-1-yl]phenyl}-3-methylisothiazol-5-yl)-L-leucinamide | MS (+ESI): 471.2 [M + 1]+ |

| NAME | CHARACTERIZATION |
|---|---|
| N¹-(cyanomethyl)-N²-{4-[4-(4-cyclopropylpiperazin-1-yl)phenyl]-3-methylisothiazol-5-yl}-L-leucinamide | MS (+ESI): 467.2 [M + 1]⁺ |
| N¹-(cyanomethyl)-N²-(4-{4-[4-(2-methoxyethyl)piperazin-1-yl]phenyl}-3-methylisothiazol-5-yl)-L-leucinamide | MS (+ESI): 485.2 [M + 1]⁺ |
| N¹-(cyanomethyl)-N²-(4-{4-[4-(2-fluoroethyl)piperazin-1-yl]phenyl}-3-methylisothiazol-5-yl)-L-leucinamide | MS (+ESI): 473.2 [M + 1]⁺ |
| N¹-(cyanomethyl)-N²-(4-{6-[(dimethylamino)methyl]-2-naphthyl}-3-methylisothiazol-5-yl)-L-leucinamide | MS (+ESI): 450.2 [M + 1]⁺ |
| N¹-(cyanomethyl)-N²-{3-methyl-4-[6-(pyrrolidin-1-ylmethyl)-2-naphthyl]isothiazol-5-yl}-L-leucinamide | MS (+ESI): 476.1 [M + 1]⁺ |
| N¹-(cyanomethyl)-N²-(4-{4-[4-(2-hydroxypropyl)piperazin-1-yl]phenyl}-3-methylisothiazol-5-yl)-L-leucinamide | MS (+ESI): 485.1 [M + 1]⁺ |
| N¹-(cyanomethyl)-N²-(4-{4-[4-(2-hydroxy-2-methylpropyl)piperazin-1-yl]phenyl}-3-methylisothiazol-5-yl)-L-leucinamide | MS (+ESI): 499.1 [M + 1]⁺ |
| N²-(4-{4-[4-(2-anilino-2-oxoethyl)piperazin-1-yl]phenyl}-3-methylisothiazol-5-yl)-N¹-(cyanomethyl)-L-leucinamide | MS (+ESI): 560.2 [M + 1]⁺ |
| N²-(4-{4-[4-(2-amino-2-oxoethyl)piperazin-1-yl]phenyl}-3-methylisothiazol-5-yl)-N¹-(cyanomethyl)-L-leucinamide | MS (+ESI): 484.1 [M + 1]⁺ |
| N-(cyanomethyl)-4-methyl-2-[(4-piperazin-1-ylbenzyl)thio]pentanamide | MS (+ESI) 361.2 [M + 1]⁺ |
| N-(cyanomethyl)-2-{[(4'-piperazin-1-yl-1,1'-biphenyl-4-yl)methyl]thio}pentanamide | MS (−ESI) 435.1 [M − 1]⁻ |
| N-(cyanomethyl)-2-{[4-(1H-imidazol-4-yl)phenyl]thio}-4-methylpentanamide | MS (+APCI) 329.3 [M + 1]⁺ |
| (2R)-N-(cyanomethyl)-4-methyl-2-[(4'-piperazin-1-yl-1,1'-biphenyl-4-yl)thio]pentanamide | MS (−ESI) 421.1 [M − 1]⁻ |
| (2S)-N-(cyanomethyl)-4-methyl-2-[(4'-piperazin-1-yl-1,1'-biphenyl-4-yl)thio]pentanamide | MS (−ESI) 421.1 [M − 1]⁻ |
| N-(cyanomethyl)-1-[(4'-piperazin-1-yl-1,1'-biphenyl-4-yl)thio]cyclohexanecarboxamide | MS (−ESI) 433.5 [M − 1]⁻ |
| N-(cyanomethyl)-4-methyl-2-[(4'-{[2-(trimethylsilyl)ethyl]sulfonyl}-1,1'-biphenyl-4-yl)thio]pentanamide | MS (−ESI) 501.1 [M − 1]⁻ |
| N¹-(cyanomethyl)-N²-{3-methyl-4-[4-(4-methylmorpholin-2-yl)phenyl]isothiazol-5-yl}-L-leucinamide | MS (+ESI): 442.5 [M + 1]⁺ |
| N¹-(cyanomethyl)-N²-[3-methyl-4-(4-morpholin-4-ylphenyl)isothiazol-5-yl]-L-leucinamide | MS (+ESI): 428.1 [M + 1]⁺ |
| 1-(5-bromo-2-chlorophenyl)-N-(cyanomethyl)piperidine-2-carboxamide | MS (+ESI): 357.9 [M + 1]⁺ |
| 1-(3-bromo-4-chlorophenyl)-N-(cyanomethyl)piperidine-2-carboxamide | MS (+ESI): 357.9 [M + 1]⁺ |
| 1-(4-chloro-1,1'-biphenyl-3-yl)-N-(cyanomethyl)piperidine-2-carboxamide | MS (+ESI): 354.1 [M + 1]⁺ |
| (4S)-1-(2-chlorophenyl)-N-(cyanomethyl)-4-methyl-L-prolinamide | MS (+APCI): 278.0 [M + 1]⁺ |
| N¹-(cyanomethyl)-N²-(4-phenylthien-3-yl)-L-leucinamide | MS (−ESI): 326.0 [M − 1]⁻ |
| N¹-(1-cyanocyclopropyl)-N²-[4-(4-piperazin-1-ylphenyl)thien-3-yl]-L-leucinamide | MS (−APCI): 436.4 [M − 1]⁻ |
| N¹-(cyanomethyl)-N²-[1-methyl-4-(4-piperazin-1-ylphenyl)-1H-pyrazol-3-yl]leucinamide | MS (−ESI): 408.4 [M − 1]⁻ |
| N¹-(cyanomethyl)-N²-[3-methyl-4-(4-piperazin-1-ylphenyl)isothiazol-5-yl]leucinamide | MS (+ESI): 428.0 [M + 1]⁺ |
| N¹-(cyanomethyl)-N²-[4-(4-piperazin-1-ylphenyl)-1,2,5-oxadiazol-3-yl]leucinamide | MS (+APCI): 455.2 [M + 1]⁺ |
| N¹-(cyanomethyl)-N²-[4-(4-piperazin-1-ylphenyl)-1H-pyrazol-3-yl]leucinamide | MS (+ESI): 398.4 [M + 1]⁺ |
| N¹-(cyanomethyl)-N²-[3-methyl-4-(4-piperazin-1-ylphenyl)isoxazol-5-yl]leucinamide | MS (−ESI): 409.7 [M − 1]⁻ |
| 2-{[4-(4-chlorophenyl)-1,2,3-thiadiazol-5-yl]thio}-N-(cyanomethyl)-4-methylpentanamide | MS (+APCI): 381.0 [M + 1]⁺ |
| N-(cyanomethyl)-4-methyl-2-[(3-methyl-1-phenyl-1H-pyrazol-5-yl)thio]pentanamide | MS (+ESI): 343.2 [M + 1]⁺ |
| 2-[(4-bromo-3-methyl-1-phenyl-1H-pyrazol-5-yl)thio]-N-(cyanomethyl)-4-methylpentanamide | MS (+APCI): 422.8 [M + 1]⁺ |
| (4S)-1-(6-chloro-4'-piperazin-1-yl-1,1'-biphenyl-3-yl)-N-(cyanomethyl)-4-methyl-L-prolinamide | MS (−APCI): 436.2 [M − 1]⁻ |
| 1-(3-bromophenyl)-N-(cyanomethyl)-D-prolinamide | MS (−APCI): 306.1 [M − 1]⁻ |
| (4S)-1-(4-chloro-4'-piperazin-1-yl-1,1'-biphenyl-3-yl)-N-(cyanomethyl)-4-methyl-L-prolinamide | MS (−APCI): 436.2 [M − 1]⁻ |
| N-(cyanomethyl)-1-(4'-piperazin-1-yl-1,1'-biphenyl-3-yl)-D-prolinamide | MS (−APCI): 340.0.2 [M − 1]⁻ |
| 1-(5-bromo-2-chlorophenyl)-N-(cyanomethyl)-D-prolinamide | MS (−APCI): 340.0.2 [M − 1]⁻ |
| 1-(3-bromo-4-chlorophenyl)-N-(cyanomethyl)-D-prolinamide | MS (−APCI): 340.0.2 [M − 1]⁻ |
| (4S)-1-[4-chloro-4'-(hydroxymethyl)-1,1'-biphenyl-3-yl]-N-(cyanomethyl)-4-methyl-L-prolinamide | MS (−ESI): 382.0 [M − 1]⁻ |
| (4S)-1-(2-chloro-1,1'-biphenyl-3-yl)-N-(cyanomethyl)-4-methyl-L-prolinamide | MS (−ESI): 352.0 [M − 1]⁻ |
| (4S)-1-{4-chloro-4'-[(dimethylamino)methyl]-1,1'-biphenyl-3-yl}-N-(cyanomethyl)-4-methyl-L-prolinamide | MS (+ESI): 411.1 [M + 1]⁺ |
| N¹-(cyanomethyl)-N²-[5-methyl-4-(4-piperazin-1-ylphenyl)isoxazol-3-yl]leucinamide | MS (+APCI): 411.4 [M + 1]⁺ |
| N¹-(cyanomethyl)-N²-(4-{4-[(methylamino)methyl]phenyl}thien-3-yl)-L-leucinamide | MS (+APCI): 371.2 [M + 1]⁺ |
| N²-(4-{4-[(tert-butylamino)methyl]phenyl}thien-3-yl)-N¹-(cyanomethyl)-L-leucinamide | MS (+ESI): 413.3 [M + 1]⁺ |
| N¹-(cyanomethyl)-N²-[4-(4-{[(2,2,2-trifluoroethyl)amino]methyl}phenyl)thien-3-yl]-L-leucinamide | MS (+ESI): 439.2 [M + 1]⁺ |
| N¹-(cyanomethyl)-N²-(4-{4-[1-(methylamino)ethyl]phenyl}thien-3-yl)-L-leucinamide | MS (+ESI): 385.3 [M + 1]⁺ |
| N¹-(cyanomethyl)-N²-(4-{4-[(isopropylamino)methyl]phenyl}thien-3-yl)-L-leucinamide | MS (+ESI): 400.2 [M + 1]⁺ |
| N¹-(cyanomethyl)-N²-[4-(4-{[(cyclopropylmethyl)amino]methyl}phenyl)thien-3-yl]-L-leucinamide | MS (+ESI): 411.5 [M + 1]⁺ |
| N¹-(cyanomethyl)-N²-(4-{4-[1-(isopropylamino)ethyl]phenyl}thien-3-yl)-L-leucinamide | MS (−APCI): 411.5 [M − 1]⁻ |
| N¹-(cyanomethyl)-N²-[4-(4-{[(2S)-2-(hydroxymethyl)pyrrolidin-1-yl]methyl}phenyl)thien-3-yl]-L-leucinamide | MS (+ESI): 441.4 [M + 1]⁺ |
| N¹-(cyanomethyl)-N²-[4-(4-{[(3-pyrrolidin-1-ylpropyl)amino]methyl}phenyl)thien-3-yl]-L-leucinamide | MS (+ESI): 468.3 [M + 1]⁺ |
| N¹-(cyanomethyl)-N²-{4-[4-(1H-imidazol-1-ylmethyl)phenyl]thien-3-yl}-L-leucinamide | MS (+ESI): 408.2 [M + 1]⁺ |
| N¹-(cyanomethyl)-N²-{4-[6-(4-methylpiperazin-1-yl)pyridin-3-yl]thien-3-yl}-L-leucinamide | MS (+ESI): 427.4 [M + 1]⁺ |
| N¹-(cyanomethyl)-N²-[4-(6-piperazin-1-ylpyridin-3-yl)thien-3-yl]-L-leucinamide | MS (+ESI): 413.1 [M + 1]⁺ |
| 1-(4-chloro-1,1'-biphenyl-3-yl)-N-(cyanomethyl)-D-prolinamide | MS (+ESI): 340.1 [M + 1]⁺ |
| (4S)-1-[4-chloro-4'-(methylthio)-1,1'-biphenyl-3-yl]-N-(cyanomethyl)-4-methyl-L-prolinamide | MS (+ESI): 402.0 [M + 1]⁺ |
| (4S)-1-[4-chloro-4'-(methylsulfonyl)-1,1'- | MS (+ESI): 434.1 |

-continued

| NAME | CHARACTERIZATION |
|---|---|
| biphenyl-3-yl]-N-(cyanomethyl)-4-methyl-L-prolinamide | [M + 1]+ |
| N-(cyanomethyl)-1-(2-phenyl-1,3-thiazol-4-yl)-L-prolinamide | MS (+ESI): 313.3 [M + 1]+ |
| (4S)-N-(cyanomethyl)-4-methyl-1-(2-phenyl-1,3-thiazol-4-yl)-L-prolinamide | MS (+ESI): 327.3 [M + 1]+ |
| (2S)-N-(cyanomethyl)-4-methyl-2-{[4'-(1-piperazinyl)[1,1'-biphenyl]-4-yl]amino}pentanamide | MS (+ESI): 406.9 [M + 1]+ |
| (2S)-N-(cyanomethyl)-4-methyl-2-{[4'-(1-piperazinyl)[1,1'-biphenyl]-3-yl]amino}pentanamide | MS (+ESI): 406.9 [M + 1]+ |
| 1-(3-bromoanilino)-N-(cyanomethyl)cyclohexanecarboxamide | MS (+ESI): 337 [M + 1]+ |
| (2S)-N-(cyanomethyl)-4-methyl-2-{[4'-(1-piperazinyl)[1,1'-biphenyl]-2-yl]amino}pentanamide | MS (−ESI): 404.5 [M − 1]− |
| (2S)-N-(cyanomethyl)-4-methyl-2-({4'-[2-(4-methyl-1-piperazinyl)-1,3-thiazol-4-yl][1,1'-biphenyl]-3-yl}amino)pentanamide | MS (+ESI): 503.3 [M + 1]+ |
| (2S)-N-(cyanomethyl)-4-methyl-2-({4'-[2-(4-methyl-1-piperazinyl)-1,3-thiazol-4-yl][1,1'-biphenyl]-2-yl}amino)pentanamide | MS (+ESI): 503.3 [M + 1]+ |
| N-(cyanomethyl)-4-methyl-2-({3-[4-(1-piperazinyl)phenyl]-2-pyridinyl}oxy)pentanamide | MS (+ESI): 408.9 [M + 1]+ |
| (2S)-N-(cyanomethyl)-4-methyl-2-({5-[4-(1-piperazinyl)phenyl]-2-pyridinyl}amino)pentanamide | MS (+ESI): 407.2 [M + 1]+ |
| 2-([1,1'-biphenyl]-4-ylmethoxy)-N-(cyanomethyl)-4-methylpentanamide | MS (−APCI): 335.3 [M − 1]− |
| N-(cyanomethyl)-4-methyl-2-[(5-phenyl-4H-1,2,4-triazol-3-yl)sulfanyl]pentanamide | MS (−APCI): 328.2 [M − 1]− |
| N-(cyanomethyl)-4-methyl-2-{[4'-(1-piperazinyl)[1,1'-biphenyl]-4-yl]sulfonyl}pentanamide | MS (+ESI): 455.2 [M + 1]+ |
| N-(cyanomethyl)-4-methyl-2-{[4'-(1-piperazinyl)[1,1'-biphenyl]-3-yl]sulfonyl}pentanamide | MS (+ESI): 455.2 [M + 1]+ |
| N-(cyanomethyl)-4-methyl-2-{[4'-(1-piperazinyl)[1,1'-biphenyl]-2-yl]sulfonyl}pentanamide | MS (+APCI): 455.2 [M + 1]+ |
| N-(cyanomethyl)-4-methyl-2-{[4'-(1-piperazinyl)[1,1'-biphenyl]-3-yl]sulfanyl}pentanamide | MS (−APCI): 421.2 [M − 1]− |
| N-(cyanomethyl)-4-methyl-2-{[4'-(1-piperazinyl)[1,1'-biphenyl]-2-yl]sulfanyl}pentanamide | MS (−APCI): 421.2 [M − 1]− |
| 1-[(2-bromophenyl)sulfanyl]-N-(cyanomethyl)cyclohexanecarboxamide | 1H NMR (400 MHz, d6 acetone) d 7.96(br, 1H), 7.68(m, 1H), 7.50(m, 1H), 7.31(m, 1H), 7.24 (m, 1H), 4.21(m, 2H), 2.14(m, 2H), 1.80(m, 2H), 1.70(m, 2H), 1.42 (m, 4H). |
| N-(cyanomethyl)-4-methyl-2-({5-[4-(1-piperazinyl)phenyl]-2-pyrimidinyl}amino)pentanamide | MS (−ESI): 406.4 [M − 1]− |
| 2-[4-(4-bromophenyl)-1-piperazinyl]-N-(cyanomethyl)-4-methylpentanamide | MS (−ESI): 391.2 [M − 1]− |
| N-(cyanomethyl)-4-methyl-2-{[4'-(1-piperazinyl)[1,1'-biphenyl]-4-yl]sulfanyl}pentanamide | MS (−ESI): 421.7 [M − 1]− |
| N-(cyanomethyl)-1-{[4'-(1-piperazinyl)[1,1'-biphenyl]-3-yl]amino}cyclohexanecarboxamide | MS (−ESI): 416.4 [M − 1]− |
| 1-[(3-bromophenyl)sulfanyl]-N-(cyanomethyl)cyclohexanecarboxamide | MS (+ESI) m/z 355 (M + 3, 85), 353(M + 1, 100), 269(85), 157(90) |
| N-(cyanomethyl)-1-{[4'-(1-piperazinyl)[1,1'-biphenyl]-2-yl]sulfanyl}cyclohexanecarboxamide | MS (+APCI) m/z 435 (M + 1, 40), 351(100), 318(45) |
| N-(cyanomethyl)-1-{[4'-(1-piperazinyl)[1,1'-biphenyl]-3-yl]sulfanyl}cyclohexanecarboxamide | MS (+APCI) m/z 435 (M + 1, 100), 351(15) |
| triisopropylsilyl 4-[3'-(1- | MS (−APCI): 605.6 |
| {[(cyanomethyl)amino]carbonyl}-3-methylbutoxy)[1,1'-biphenyl]-4-yl]-1-piperazinecarboxylate | [M − 1]− |
| triisopropylsilyl 4-[4'-(1-{[(cyanomethyl)amino]carbonyl}-3-methylbutoxy)[1,1'-biphenyl]-4-yl]-1-piperazinecarboxylate | MS (−APCI): 605.6 [M − 1]− |
| N-(cyanomethyl)-1-{[4'-(1-piperazinyl)[1,1'-biphenyl]-4-yl]amino}cyclohexanecarboxamide | MS (+ESI): 416.1 [M + 1]+ |
| N-(cyanomethyl)-4-methyl-2-{[4'-(1-piperazinyl)[1,1'-biphenyl]-3-yl]oxy}pentanamide | MS (−ESI): 405.3 [M − 1]− |
| N-(cyanomethyl)-4-methyl-2-{[4'-(1-piperazinyl)[1,1'-biphenyl]-4-yl]oxy}pentanamide | MS (−ESI): 405.3 [M − 1]− |
| N-(cyanomethyl)-1-{[4'-(1-piperazinyl)[1,1'-biphenyl]-2-yl]amino}cyclohexanecarboxamide | MS (+APCI): 418.3 [M + 1]+ |
| N-(cyanomethyl)-4-methyl-2-{[4'-(1-piperazinyl)[1,1'-biphenyl]-2-yl]oxy}pentanamide | 1H NMR (500 MHz, d6 acetone) d 8.08–7.95 (br, 1H); 7.52(d, 2H); 7.35 (d, 1H); 7.25(t, 1H); 7.1–6.9(m, 4H); 4.62–4.52 (m, 1H); 4.2(br, 2H); 3.85(br, 1H); 3.2(br, 4H); 3.0(br, 4H); 1.85–1.6(m, 3H); 0.88–0.73 (m, 6H) |
| N-(cyanomethyl)-4-methyl-2-{[4'-(1-piperazinyl)[1,1'-biphenyl]-2-yl]methyl}pentanamide | MS (−ESI): 403.5 [M − 1]− |
| 1-(3-bromophenyl)-N-(cyanomethyl)-2-piperidinecarboxamide | MS (+ESI) m/z 324 (M + 3, 100), 322(M + 1, 90), 240(20), 238(20) |
| N-(cyanomethyl)-4-methyl-2-{[4'-(1-piperazinyl)[1,1'-biphenyl]-3-yl]methyl}pentanamide | MS (−ESI): 403.5 [M − 1]− |
| N-(cyanomethyl)-4-methyl-2-{[4'-(1-piperazinyl)[1,1'-biphenyl]-4-yl]methyl}pentanamide | MS (−ESI): 403.5 [M − 1]− |
| N-(cyanomethyl)-1-[4'-(1-piperazinyl)[1,1'-biphenyl]-3-yl]-2-piperidinecarboxamide | MS (+APCI) m/z 404 (M + 1, 100), 320 (15) |
| (2S)-N-(cyanomethyl)-4-methyl-2-({2-methyl-3-oxo-5-[4-(1-piperazinyl)phenyl]-2,3-dihydro-4-pyridazinyl}amino)pentanamide | MS (+APCI) m/z 438 (M + 1, 100), 163 (15) |
| (2R,3S)-1-(3-bromophenyl)-N-(cyanomethyl)-3-methyl-2-piperidinecarboxamide | MS (+APCI) m/z 338 (M + 3, 95), 336(M + 1, 100), 254(40) |
| (2S)-N-(cyanomethyl)-4-methyl-2-({[4'-(1-piperazinyl)[1,1'-biphenyl]-3-yl]methyl}amino)pentanamide | MS (+APCI): 420.3 [M + 1]+ |
| (2S)-N-(cyanomethyl)-4-methyl-2-({[4'-(1-piperazinyl)[1,1'-biphenyl]-4-yl]methyl}amino)pentanamide | MS (+APCI): 420.3 [M + 1]+ |
| tert-butyl 4-{3'-[(1-{[(cyanomethyl)amino]carbonyl}-3-methylbutoxy)methyl][1,1'-biphenyl]-4-yl}-1-piperazinecarboxylate | MS (−ESI): 519.6 [M − 1]− |
| tert-butyl 4-{4'-[(1-{[(cyanomethyl)amino]carbonyl}-3-methylbutoxy)methyl][1,1'-biphenyl]-4-yl}-1-piperazinecarboxylate | MS (−ESI): 519.6 [M − 1]− |
| tert-butyl 4-{2'-[(1-{[(cyanomethyl)amino]carbonyl}-3-methylbutoxy)methyl][1,1'-biphenyl]-4-yl}-1-piperazinecarboxylate | MS (−ESI): 519.3 [M − 1]− |
| 1-[1,1'-biphenyl]-3-yl-N-(cyanomethyl)-2-piperidinecarboxamide | MS (+APCI) m/z 320 (M + 1, 100), 236(25) |
| N-(cyanomethyl)-1-[3-(2-naphthyl)phenyl]-2-piperidinecarboxamide | MS (+APCI) m/z 370 (M + 1, 100), 286(35) |
| N-(cyanomethyl)-4-methyl-2-{[4'-(1-piperazinyl)[1,1'-biphenyl]-2-yl]methoxy}pentanamide | 1H NMR (400 MHz, d6 acetone) d 7.8(br, 1H); 7.55(br, 1H); 7.35(br, 2H); 7.25(br, 3H); 7.0 (br, 2H); 4.6(m, 1H); |

-continued

| NAME | CHARACTERIZATION |
|---|---|
| | 4.45(m, 1H); 4.2(br, 2H); 3.87(br, 1H); 3.2 (br, 4H); 2.95(br, 4H); 2.6(br, 1H); 1.78(br, 1H); 1.6(br, 1H); 1.49 (br, 1H); 0.92–0.80(m, 6H) |
| N-(cyanomethyl)-4-methyl-2-{[4'-(1-piperazinyl)[1,1'-biphenyl]-3-yl]methoxy}pentanamide | MS (−APCI): 419.5 [M − 1]− |
| N-(cyanomethyl)-4-methyl-2-{[4'-(1-piperazinyl)[1,1'-biphenyl]-4-yl]methoxy}pentanamide | MS (−APCI): 419.5 [M − 1]− |
| N-(cyanomethyl)-2-[(5,5-dimethyl-2-oxo-4-phenyl-2,5-dihydro-3-furanyl)amino]-4-methylpentanamide | MS (+APCI) m/z 356 (M + 1, 5), 312(15), 272 (100), 226(50) |
| (2S)-N-(cyanomethyl)-4-methyl-2-({4-[4-(1-piperazinyl)phenyl]-3-thienyl}amino)pentanamide | MS (+ESI): 412.0 [M + 1]+ |

PHARMACEUTICAL COMPOSITION

As a specific embodiment of this invention, 100 mg of (2S)-N-(cyanomethyl)-4-methyl-2-{[4'-(1-piperazinyl)[1,1'-biphenyl]-4-yl]amino}pentanamide, is formulated with sufficient finely divided lactose to provide a total amount of 580 to 590 mg to fill a size 0, hard-gelatin capsule.

Cathepsin K Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; and DTT, 2.5 mM) and 25 μL of human cathepsin K (0.1 nM) in assay buffer solution. The assay solutions were mixed for 5–10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Compounds of the invention were tested by the above-described assay and observed to exhibit cathepsin K inhibitory activity.

Cathepsin L Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; and DTT, 2.5 mM) and 25 μL of human cathepsin L (1.5 nM) in assay buffer solution. The assay solutions were mixed for 5–10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Compounds of the invention were tested by the above-described assay and observed to exhibit cathepsin L inhibitory activity.

Cathepsin B Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; and DTT, 2.5 mM) and 25 μL of human cathepsin B (2.5 nM) in assay buffer solution. The assay solutions were mixed for 5–10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Compounds of the invention were tested by the above-described assay and observed to exhibit cathepsin B inhibitory activity.

Cathepsin S Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; and DTT, 2.5 mM) and 25 μL of human cathepsin S (4 nM) in assay buffer solution. The assay solutions were mixed for 5–10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Compounds of the invention were tested by the above-described assay and observed to exhibit cathepsin S inhibitory activity.

What is claimed is:

1. A compound of the formula:

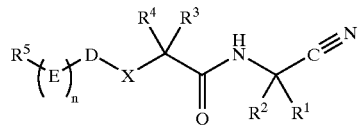

wherein $R^1$ is hydrogen, $C_{1-6}$ alkyl or $C_{2-6}$ alkenyl wherein said alkyl and alkenyl groups are optionally substituted with halo;

$R^2$ is hydrogen, $C_{1-6}$ alkyl or $C_{2-6}$ alkenyl wherein said alkyl and alkenyl groups are optionally substituted with halo;

or $R^1$ and $R^2$ can be taken together with the carbon atom to which they are attached to form a $C_{3-8}$ cycloalkyl ring wherein said ring system is optionally substituted with $C_{1-6}$ alkyl, hydroxyalkyl or halo;

$R^3$ is hydrogen, $C_{1-6}$ alkyl or $C_{2-6}$ alkenyl wherein said alkyl and alkenyl groups are optionally substituted with $C_{3-6}$ cycloalkyl or halo;

R$^4$ is hydrogen, C$_{1-6}$ alkyl or C$_{2-6}$ alkenyl wherein said alkyl and alkenyl groups are optionally substituted with C$_{3-6}$ cycloalkyl or halo;

or R$^3$ and R$^4$ can be taken together with the carbon atom to which they are attached to form a C$_{3-8}$ cycloalkyl ring, C$_{5-8}$ cycloalkenyl ring, or five to seven membered heterocyclyl wherein said cycloalkyl, cycloalkenyl and heterocyclyl groups are optionally substituted with C$_{1-6}$ alkyl, halo, hydroxyalkyl, hydroxy, alkoxy or keto;

X is selected from the group consisting of NH, NR$^6$, —NHSO$_2$—, O, —C(R$^7$)(R$^8$)O—, —OC(R$^7$)(R$^8$)—, —C(R$^7$)(R$^8$)C(R$^7$)(R$^8$)O—, S, SO$_2$, —C(R$^7$)(R$^8$)S—, —SC(R$^7$)(R$^8$)—, C(R$^7$)(R$^8$)SO$_2$, SO$_2$C(R$^7$)(R$^8$)—, —C(R$^7$)(R$^8$)—, —C(R$^7$)(R$^8$)N(R$^7$)—, —N(R$^7$)C(R$^7$)(R$^8$)—;

R$^6$ is C$_{1-6}$ alkyl;

or R$^6$ and R$^4$ can be taken together with any of the atoms to which they may be attached or are between them to form a 4–12 membered heterocyclyl ring system wherein said ring system, which may be monocyclic or bicyclic, is optionally substituted with C$_{1-6}$ alkyl, halo, hydroxyalkyl, hydroxy, keto, OR$^7$, SR$^7$ or N(R$^7$)$_2$;

R$^7$ is hydrogen or C$_{1-6}$ alkyl;

R$^8$ is hydrogen or C$_{1-6}$ alkyl;

D is aryl, heteroaryl, C$_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from hydrogen, halogen, C$_{1-10}$ alkyl, C$_{3-8}$ cycloalkyl, aryl, arylC$_{1-8}$ alkyl, amino, aminoC$_{1-8}$ alkyl, C$_{1-3}$ acylamino, C$_{1-3}$ acylamino C$_{1-8}$ alkyl, C$_{1-6}$ alkylamino, C$_{1-6}$ alkylamino C$_{1-8}$ alkyl, C$_{1-6}$ dialkylamino, C$_{1-6}$ dialkylamino-C$_{1-8}$ alkyl, C$_{1-4}$ alkoxy, C$_{1-4}$ alkoxyC$_{1-6}$ alkyl, hydroxycarbonyl, hydroxycarbonylC$_{1-6}$ alkyl, C$_{1-5}$ alkoxycarbonyl, C$_{1-3}$ alkoxycarbonyl C$_{1-6}$ alkyl, hydroxycarbonylC$_{1-6}$ alkyloxy, hydroxy, hydroxyC$_{1-6}$ alkyl, cyano, trifluoromethyl, oxo and C$_{1-5}$ alkylcarbonyloxy;

E is aryl, heteroaryl, C$_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from hydrogen, halogen, C$_{1-10}$ alkyl, C$_{3-8}$ cycloalkyl, aryl, arylC$_{1-8}$ alkyl, amino, aminoC$_{1-8}$ alkyl, C$_{1-3}$ acylamino, C$_{1-3}$ acylamino C$_{1-8}$ alkyl, C$_{1-6}$ alkylamino, C$_{1-6}$ alkylaminoC$_{1-8}$ alkyl, C$_{1-6}$ dialkylamino, C$_{1-6}$ dialkylamino-C$_{1-8}$ alkyl, C$_{1-4}$ alkoxy, C$_{1-4}$ alkoxy C$_{1-6}$ alkyl, hydroxycarbonyl, hydroxycarbonyl C$_{1-6}$ alkyl, C$_{1-5}$ alkoxycarbonyl, C$_{1-3}$ alkoxycarbonyl C$_{1-6}$ alkyl, hydroxycarbonyl C$_{1-6}$ alkyloxy, hydroxy, hydroxy C$_{1-6}$ alkyl, cyano, trifluoromethyl, oxo and C$_{1-5}$ alkylcarbonyloxy;

R$^5$ is hydrogen, C$_{1-6}$ alkyl, C$_{2-6}$ alkenyl, C$_{1-6}$ alkyloxy, halo, nitro, cyano, amino, aryl, heteroaryl, C$_{3-8}$ cycloalkyl, heterocyclyl, —C(O)OR$^7$, —C(O)OSi[CH(CH$_3$)$_2$]$_3$, —OR$^7$, —C(O)R$^7$, —R$^7$C(O)R$^9$, —C(O)R$^9$, —C(O)N(R$^7$)(R$^8$), —C(O)(R$^7$)N(R$^7$)(R$^8$), —SR$^7$, —SR$^9$, —R$^7$SR$^9$, —R$^9$, —C(R$^9$)$_3$, —C(R$^7$)(R$^8$)N(R$^9$)$_2$, —NR$^7$CONR$^7$S(O)$_2$R$^9$, —SO$_2$R$^7$, —SO$_2$R$^9$, —SO$_2$N(R$^7$)(R$^8$), —SO$_2$CH(R$^7$)(R$^8$), —OSO$_2$R$^7$, —N(R$^7$)C(O)NR$^7$R$^9$, —N(R$^7$)C(O)R$^7$, —N(R$^7$)C(O)OR$^7$, —N(R$^7$)SO$_2$R$^7$, —C(R$^7$)(R$^8$)NR$^7$C(R$^7$)(R$^8$)R$^9$, —C(R$^7$)(R$^8$)N(R$^7$)R$^9$, C(R$^7$)(R$^8$)N(R$^7$)(R$^8$), —C(R$^a$)(R$^b$)NR$^a$C(R$^a$)(R$^b$), —C(R$^a$)(R$^b$)N(R$^a$)(R$^b$), —C(R$^a$)(R$^b$)C(R$^a$)(R$^b$)N(R$^a$)(R$^b$), —C(O)C(R$^a$)(R$^b$)N(R$^a$)(R$^b$), C(O)C(R$^a$)(R$^b$)S(R$^a$)(R$^b$), C(R$^a$)(R$^b$)C(O)N(R$^a$)(R$^b$);

wherein the above R$^5$ groups can be optionally substituted on either the carbon or the heteroatom with one to five substituents independently selected from the group consisting of C$_{1-6}$ alkyl, aryl, halo, —OR$^7$, —O(aryl), —NO$_2$, —NH$_2$, —NHS(O)$_2$R$^6$, C(R$^7$)(R$^8$)N(R$^7$)(R$^8$), —C(R$^a$)(R$^b$)C(O)N(R$^a$)(R$^b$), —N(R$^7$)C(R$^7$)(R$^8$), —NH(CH$_2$)$_2$OH, —NHC(O)OR$^7$, Si(CH$_3$)$_3$, heterocyclyl and heteroaryl;

R$^9$ is selected from the group consisting of aryl, aryl(C$_{1-4}$) alkyl, heteroaryl, heteroaryl(C$_{1-4}$)alkyl, C$_{3-8}$cycloalkyl, C$_{3-8}$cycloalkyl(C$_{1-4}$)alkyl, and heterocyclyl(C$_{1-4}$)alkyl; and R$^a$ is hydrogen, C$_{1-6}$ alkyl, (C$_{1-6}$ alkyl)aryl, (C$_{1-6}$ alkyl) hydroxyl, hydroxyl, halo, aryl, heteroaryl, C$_{3-8}$ cycloalkyl, heterocyclyl, wherein said alkyl, aryl, heteroaryl, C$_{3-8}$ cycloalkyl and heterocyclyl can be optionally substituted on either the carbon or the heteroatom with C$_{1-6}$ alkyl or halo;

R$^b$ is hydrogen, C$_{1-6}$ alkyl, (C$_{1-6}$ alkyl)aryl, (C$_{1-6}$ alkyl) hydroxyl, hydroxyl, halo, aryl, heteroaryl, C$_{3-8}$ cycloalkyl, heterocyclyl,wherein said alkyl, aryl, heteroaryl, C$_{3-8}$ cycloalkyl and heterocyclyl can be optionally substituted on either the carbon or the heteroatom with C$_{1-6}$ alkyl or halo;

or R$^a$ and R$^b$ can be taken together with the carbon atom to which they are attached or are between them to form a C$_{3-8}$ cycloalkyl ring or C$_{3-8}$ heterocyclyl ring wherein said 3–8 membered ring system may be optionally substituted with C$_{1-6}$ alkyl and halo;

n is independently selected from an integer from one to two;

provided that when R$^1$ and R$^2$ are taken together with the carbon atom to which they are attached to form a C$_{3-8}$ cycloalkyl ring, n is independently selected from zero to two;

and provided that when R$^3$ and R$^4$ are taken together with the carbon atom to which they are attached to form a C$_{3-8}$ cycloalkyl ring, n is independently selected from zero to two;

and provided that when R$^4$ and R$^6$ are taken together with the carbon atom to which they are attached to form a C$_{3-8}$ cycloalkyl ring, n is independently selected from zero to two;

and the pharmaceutically acceptable salts and N-oxide derivatives thereof.

2. The compound of claim 1 wherein R$^3$ is C$_{1-4}$ alkyl, and R$^4$ is hydrogen; and the pharmaceutically acceptable salts and N-oxide derivatives thereof.

3. The compound of claim 1 wherein R$^1$ and R$^2$ can be taken together with the carbon atom to which they are attached to form a C$_{3-8}$ cycloalkyl ring wherein said ring system is optionally substituted with C$_{1-6}$ alkyl, hydroxyalkyl or halo; and the pharmaceutically acceptable salts and N-oxide derivatives thereof.

4. The compound of claim 1 wherein X is NR$^6$; R$^6$ and R$^4$ can be taken together with any of the atoms to which they may be attached or are between them to form a 4–8 membered heterocyclyl ring system wherein said ring system, which may be monocyclic or bicyclic, is optionally substituted with C$_{1-6}$ alkyl, halo, hydroxyalkyl, hydroxy, keto, OR$^7$, SR$^7$ or N(R$^7$)$_2$; n is an integer from zero to two; and the pharmaceutically acceptable salts and N-oxide derivatives thereof.

5. The compound of claim 4 wherein $R^6$ and $R^4$ can be taken together with any of the atoms to which they may be attached or are between them to form a 5 or 6 membered heterocyclyl ring system wherein said ring system is optionally substituted with $C_{1-6}$ alkyl, halo, hydroxyalkyl, hydroxy, keto, $OR^7$, $SR^7$ or $N(R^7)_2$; and the pharmaceutically acceptable salts and N-oxide derivatives thereof.

6. The compound of claim 5 selected from:
(4S)-1-(3-bromophenyl)-N-cyanomethyl)-4-methyl-prolinamide;
(4S)-N-(cyanomethyl)-4-methyl-1-(4'-piperazin-1-yl-1,1'-biphenyl-3-yl)-L-prolinamide;
(4S)-N-(1-cyanocyclopropyl)-4-methyl-1-(4'-piperazin-1-yl-1,1'-biphenyl-3-yl)-L-prolinamide;
(4S)-1-(1,1'-biphenyl-3-yl)-N-(cyanomethyl)-4-methyl-L-prolinamide;
(4S)-1-(4-chloro-1,1'-biphenyl-3-yl)-N-(cyanomethyl)-4-methyl-L-prolinamide;
(4S)-N-(cyanomethyl)-1-[3-(3,3-dimethylbut-1-ynyl)phenyl]-4-methyl-L-prolinamide;
(4S)-N-(cyanomethyl)-1-[3-(3-hydroxy-3-methylbut-1-ynyl)phenyl]-4-methyl-L-prolinamide;
N-(cyanomethyl)-1-(1-phenyl-1H-tetraazol-5-yl)piperidine-2-carboxamide;
(4S)-1-(5-bromo-2-chlorophenyl)-N-(cyanomethyl)-4-methyl-L-prolinamide;
(4S)-1-(3-bromo-4-chlorophenyl)-N-(cyanomethyl)-4-methyl-L-prolinamide;
(4S)-1-(6-chloro-1,1'-biphenyl-3-yl)-N-(cyanomethyl)-4-methyl-L-prolinamide;
1-(5-bromo-2-chlorophenyl)-N-(cyanomethyl)piperidine-2-carboxamide;
1-(3-bromo-4-chlorophenyl)-N-(cyanomethyl)piperidine-2-carboxamide;
1-(4-chloro-1,1'-biphenyl-3-yl)-N-(cyanomethyl)piperidine-2-carboxamide;
(4S)-1-(2-chlorophenyl)-N-(cyanomethyl)-4-methyl-L-prolinamide;
(4S)-1-(6-chloro-4'-piperazin-1-yl-1,1'-biphenyl-3-yl)-N-(cyanomethyl)-4-methyl-L-prolinamide;
1-(3-bromophenyl)-N-(cyanomethyl)-D-prolinamide;
(4S)-1-(4-chloro-4'-piperazin-1-yl-1,1'-biphenyl-3-yl)-N-(cyanomethyl)-4-methyl-L-prolinamide;
N-(cyanomethyl)-1-(4'-piperazin-1-yl 1,1'-biphenyl-3-yl)-D-prolinamide;
1-(5-bromo-2-chlorophenyl)-N-(cyanomethyl)-D-prolinamide;
1-(3-bromo-4-chlorophenyl)-N-(cyanomethyl)-D-prolinamide;
(4S)-1-[4-chloro-4'-(hydroxymethyl)-1,1'-biphenyl-3-yl]-N-(cyanomethyl)-4-methyl-L-prolinamide;
(4S)-1-(2-chloro-1,1'-biphenyl-3-yl)-N-(cyanomethyl)-4-methyl-L-prolinamide;
(4S)-1-{4-chloro-4'-[(dimethylamino)methyl]-1,1'-biphenyl-3-yl}-N-(cyanomethyl)-4-methyl-L-prolinamide;
1-(4-chloro-1,1'-biphenyl-3-yl)-N-(cyanomethyl)-D-prolinamide;
(4S)-1-[4-chloro-4'-(methylthio)-1,1'-biphenyl-3-yl]-N-(cyanomethyl)-4-methyl-L-prolinamide;
(4S)-1-[4-chloro-4'-(methylsulfonyl)-1,1'-biphenyl-3-yl]-N-(cyanomethyl)-4-methyl-L-prolinamide;
N-(cyanomethyl)-1-(2-phenyl-1,3-thiazol-4-yl)-L-prolinamide;
(4S)-N-(cyanomethyl)-4-methyl-1-(2-phenyl-1,3-thiazol-4-yl)-L-prolinamide;
(4S)-1-(4-chloro-4'-piperazin-1-yl-1,1'-biphenyl-3-yl)-N-(cyanomethyl)-4-hydroxy-L-prolinamide;
(4R)-1-(4-chloro-4'-piperazin-1-yl-1,1'-biphenyl-3-yl)-N-(cyanomethyl)-4-hydroxy-L-prolinamide;
1-(4-chloro-4'-piperazin-1-yl-1,1'-biphenyl-3-yl)-N-(cyanomethyl)-4-oxo-L-prolinamide;
(4S)-1-(4-chloro-4'-piperazin-1-yl-1,1'-biphenyl-3-yl)-N-(cyanomethyl)-4-fluoro-L-prolinamide; (4R)-1-(4-chloro-4'-piperazin-1-yl-1,1'-biphenyl-3-yl)-N-(cyanomethyl)-4-fluoro-L-prolinamide;
1-(4-chloro-4'-piperazin-1-yl-1,1'-biphenyl-3-yl)-N-(cyanomethyl)-4,4-difluoro-L-prolinamide;
(4S)-1-(4-chloro-4'-piperazin-1-yl-1,1'-biphenyl-3-yl)-N-(cyanomethyl)-4-methoxy-L-prolinamide;
(4R)-1-(4-chloro-4'-piperazin-1-yl-1,1'-biphenyl-3-yl)-N-(cyanomethyl)-4-methoxy-L-prolinamide;
(4S)-1-(4-chloro-4'-piperazin-1-yl-1,1'-biphenyl-3-yl)-N-(cyanomethyl)-4-(methylthio)-L-prolinamide;
(4R)-1-(4-chloro-4'-piperazin-1-yl-1,1'-biphenyl-3-yl)-N-(cyanomethyl)-4-(methylthio)-L-prolinamide;
(1R,2S,5S)-3-(4-chloro-4'-piperazin-1-yl-1,1'-biphenyl-3-yl)-N-(cyanomethyl)-3-azabicyclo[3.1.0]hexane-2-carboxamide;
(1S,2S,5R)-3-(4-chloro-4'-piperazin-1-yl-1,1'-biphenyl-3-yl)-N-(cyanomethyl)-3-azabicyclo[3.1.0]hexane-2-carboxamide;
N-(cyanomethyl)-1-[2-(4-piperazin-1-ylphenyl)cyclopropyl]-L-prolinamide;
(4S)-N-(cyanomethyl)-4-methyl-1-[2-(4-piperazin-1-ylphenyl)cyclopropyl]-L-prolinamide;
N-(cyanomethyl)-4,4-difluoro-1-[2-(4-piperazin-1-ylphenyl)cyclopropyl]-L-prolinamide;
(4S)-1-(1,3-benzothiazol-2-yl)-N-(cyanomethyl)-4-methyl-L-prolinamide;
(4S)-N-(cyanomethyl)-4-methyl-1-(1-methyl-5-piperazin-1-yl-1H-benzimidazol-2-yl)-L-prolinamide;
(4S)-1-(4-bromo-1-methyl-1H-benzimidazol-2-yl)-N-(cyanomethyl)-4-methyl-L-prolinamide;
(4S)-N-(cyanomethyl)-4-methyl-1-(1-naphthyl)-L-prolinamide;
(4S)-N-(cyanomethyl)-4-methyl-1-(2-naphthyl)-L-prolinamide;
(4S)-N-(cyanomethyl)-4-methyl-1-(5,6,7,8-tetrahydronaphthalen-2-yl)-L-prolinamide;
(4S)-N-(cyanomethyl)-4-methyl-1-(5,6,7,8-tetrahydronaphthalen-1-yl)-L-prolinamide;
(4S)-N-(cyanomethyl)-4-methyl-1-[5-methyl-2-(4-piperazin-1-ylphenyl)-1,3-thiazol-4-yl]-L-prolinamide;
N-(cyanomethyl)-1-[5-methyl-2-(4-piperazin-1-ylphenyl)-1,3-thiazol-4-yl]-L-prolinamide;
(4S)-N-(cyanomethyl)-4-methyl-1-[5-methyl-2-(3-piperazin-1-ylphenyl)-1,3-thiazol-4-yl]-L-prolinamide;
(4S)-N-(cyanomethyl)-4-methyl-1-(5-methyl-2,2'-bi-1,3-thiazol-4-yl)-L-prolinamide;
(3S)-N-(cyanomethyl)-2-[5-methyl-2-(4-piperazin-1-ylphenyl)-1,3-thiazol-4-yl]-2-azabicyclo[2.2.1]heptane-3-carboxamide;
(4S)-1-{4-chloro-4'-[(methylamino)carbonyl]-1,1'-biphenyl-3-yl}-N-(cyanomethyl)-4-methyl-L-prolinamide;
(4S)-1-(4-chloro-4'-{[(2-methoxyethyl)(methyl)amino]methyl}-1,1'-biphenyl-3-yl)-N-(cyanomethyl)-4-methyl-L-prolinamide;
(4S)-1-(4-chloro-4'-propionyl-1,1'-biphenyl-3-yl)-N-(cyanomethyl)-4-methyl-L-prolinamide;
(4S)-1-{4-chloro-4'-[(methylsulfonyl)amino]-1,1'-biphenyl-3-yl}-N-(cyanomethyl)-4-methyl-L-prolinamide;
(4S)-1-[4-chloro-4'-(2-pyrrolidin-1-ylethyl)-1,1'-biphenyl-3-yl]-N-(cyanomethyl)-4-methyl-L-prolinamide;

(4S)-1-{4-chloro-4'-[(methylamino)sulfonyl]-1,1'-biphenyl-3-yl}-N-(cyanomethyl)-4-methyl-L-prolinamide;
(4S)-1-{4-chloro4'-[(1-methyl-1H-315-imidazol-3-yl)methyl]-1,1'-biphenyl-3-yl}-N-(cyanomethyl)-4-methyl-L-prolinamide;
(4S)-1-[4-chloro-4'-(N,N-dimethylglycyl)-1,1'-biphenyl-3-yl]-N-(cyanomethyl)-4-methyl-L-prolinamide;
(4S)-1-[4-chloro-4'-(5-methyl-1,1-dioxido-1,2,5-thiadiazinan-2-yl)-1,1'-biphenyl-3-yl]-N-(cyanomethyl)-4-methyl-L-prolinamide;
(4S)-1-{4'-[1-(2-amino-2-oxoethyl)-4-hydroxypiperidin-4-yl]-4-chloro-1,1'-biphenyl-3-yl}-N-(cyanomethyl)-4-methyl-L-prolinamide;
(4S)-1-(4-chloro-4'-{[(1-methyl-1H-imidazol-2-yl)thio]methyl}-1,1'-biphenyl-3-yl)-N-(cyanomethyl)-4-methyl-L-prolinamide;
(4S)-1-{4-chloro-4'-[1-(2-hydroxyethyl)piperidin-4-yl]-1,1'-biphenyl-3-yl}-N-(cyanomethyl)-4-methyl-L-prolinamide;
(4S)-1-{2-chloro-5-[(1E,3E)-4-({2-[(2-fluoroethyl)amino]ethyl}amino)-1-methylhexa-1,3,5-trienyl]phenyl}-N-(cyanomethyl)-4-methyl-L-prolinamide;
(4S)-1-[4-chloro-4'-(2-oxoimidazolidin-1-yl)-1,1'-biphenyl-3-yl]-N-(cyanomethyl)-4-methyl-L-prolinamide;
(4S)-1-(4-chloro-4'-{1-[(methoxycarbonyl)amino]cyclopropyl}-1,1'-biphenyl-3-yl)-N-(cyanomethyl)-4-methyl-L-prolinamide;
(4S)-N-(cyanomethyl)-4methyl-1-[4-(4-piperazin-1-ylphenyl)-1,3-thiazol-2-yl]-L-prolinamide;
(4S)-N-(cyanomethyl)-4-methyl-1-[5-(4-piperazin-1-ylphenyl)-1,3-thiazol-2-yl]-L-prolinamide;
(4S)-N-(cyanomethyl)-4-methyl-1-[5-(4-piperazin-1-ylphenyl)isothiazol-3-yl]-L-prolinamide;
(4S)-N-(cyanomethyl)-4-methyl-1-[1-(4-piperazin-1-ylphenyl)-1H-pyrazol-3-yl]-L-prolinamide;
(4S)-N-(cyanomethyl)-4-methyl-1-[1-(4-piperazin-1-ylphenyl)-1H-pyrazol-4-yl]-L-prolinamide;
(4S)-N-(cyanomethyl)-4-methyl-1-[1-methyl-3-(4-piperazin-1-ylphenyl)-1H-pyrazol-5-yl]-L-prolinamide;
(4S)-N-(cyanomethyl)-4-methyl-1-[5-(4-piperazin-1-ylphenyl)-1,2,4-thiadiazol-3-yl]-L-prolinamide;
(4S)-N-(cyanomethyl)-4-methyl-1-[5-(4-piperazin-1-ylphenyl)-1,3,4-thiadiazol-2-yl]-L-prolinamide;
(4S)-N-(cyanomethyl)-4-methyl-1-[3-(4-piperazin-1-ylphenyl)-1,2,4-thiadiazol-5-yl]-L-prolinamide;
(4S)-N-(cyanomethyl)-4-methyl-1-[1-(4-piperazin-1-ylphenyl)-1H-1,2,4-triazol-3-yl]-L-prolinamide;
(4S)-N-(cyanomethyl)-4-methyl-1-[1-methyl-3-(4-piperazin-1-ylphenyl)-1H-1,2,4-triazol-5-yl]-L-prolinamide;
1-(3-bromophenyl)-N-(cyanomethyl)-2-piperidinecarboxamide;
N-(cyanomethyl)-1-[4'-(1-piperazinyl)[1,1'-biphenyl]-3-yl]-2-piperidinecarboxamide;
(2R,3S)-1-(3-bromophenyl)-N-(cyanomethyl)-3-methyl-2-piperidinecarboxamide;
1-[1,1'-biphenyl]-3-yl-N-(cyanomethyl)-2-piperidinecarboxamide;
N-(cyanomethyl)-1-[3-(2-naphthyl)phenyl]-2-piperidinecarboxamide;
N-(cyanomethyl)-1-(1-bromophenyl)piperidine-2-carboxamide;
1-{4'-[4-(tert-butyloxycarbonyl)piperazin-1-yl]-1,1'-biphenyl-4-yl}-N-(cyanomethyl)-piperidine-2-carboxamide;
1-[4'-(piperazin-1-yl)-1,1'-biphenyl-4-yl]-N-(cyanomethyl)-piperidine-2-carboxamide;
1-{3'-[4-(piperidin-1-yl)piperidin-1-yl]-1,1'-biphenyl-3-yl}-N-(cyanomethyl)-piperidine-2-carboxamide;
1-{3'-[2-(4-methylpiperazin-1-yl)thiazol-4-yl]-1,1'-biphenyl-3-yl}-N-(cyanomethyl)-piperidine-2-carboxamide;
1-{4'-[4-(morpholin-4-yl)piperidin-1-yl]-1,1'-biphenyl-3-yl}-N-(cyanomethyl)-piperidine-2-carboxamide;
1-{3'-(piperazin-1-yl)-1,1'-biphenyl-3-yl}-N-(cyanomethyl)-piperidine-2-carboxamide;
1-{4'-[2-(4-methylpiperazin-1-yl)thiazol-4-yl]1,1'-biphenyl-3-yl}-N-(cyanomethyl)-piperidine-2-carboxamide;
1-{3'-[4-(morpholin-4-yl)piperidin-1-yl]-1,1'-biphenyl-3-yl}-N-(cyanomethyl)-piperidine-2-carboxamide;
1-(4'-trifluoromethyl-1,1'-biphenyl-3-yl)-N-(cyanomethyl)-piperidine-2-carboxamide;
1-(2',3'difluoro-1,1'-biphenyl-3-yl)-N-(cyanomethyl)-piperidine-2-carboxamide;
1-{3'-[4-(tert-butyloxycarbonyl)piperazin-1-yl]-1,1'-biphenyl-4-yl}-N-(cyanomethyl)-piperidine-2-carboxamide;
1-[3'-(piperazin-1-yl)-1,1'-biphenyl-4-yl]-N-(cyanomethyl)-piperidine-2-carboxamide;
1-{4'-[4-(tert-butyloxycarbonyl)piperazin-1-yl]-1,1'-biphenyl-2-yl}-N-(cyanomethyl)-piperidine-2R-carboxamide;
N-(cyanomethyl)-1-(3-bromophenyl)piperidine-2R-carboxamide;
1-{3'-(piperazin-1-yl)-1,1'-biphenyl-3-yl}-N-(cyanomethyl)-piperidine-2R-carboxamide;
1-{3-[2-(4-morpholin-4-ylpiperazin-1-yl)thiazol-4-yl]-phenyl}-N-(cyanomethyl)-piperidine-2-carboxamide;
1-{3-[2-(piperazin-1-yl)thiazol-4-yl]-phenyl}-N-(cyanomethyl)-piperidine-2-carboxamide;
1-{3-[2-(4-methylhomopiperazin-1-yl)thiazol-4-yl]-phenyl}-N-(cyanomethyl)-piperidine-2-carboxamide;
N-(cyanomethyl)-1-(3-bromo-5-fluorophenyl)piperidine-2-carboxamide;
N-(cyanomethyl)-1-(3-bromo-6-fluorophenyl)piperidine-2-carboxamide;
N-(cyanomethyl)-1-(3-bromo-4-fluorophenyl)piperidine-2-carboxamide;
1-{5-fluoro-4'-[4-(tert-butyloxycarbonyl)piperazin-1-yl]-1,1'-biphenyl-3-yl}-N-(cyanomethyl)-piperidine-2-carboxamide;
1-[5-fluoro-4'-(piperazin-1-yl)-1,1'-biphenyl-3-yl]-N-(cyanomethyl)-piperidine-2-carboxamide;
1-{6-fluoro-4'-[4-(tert-butyloxycarbonyl)piperazin-1-yl]-1,1'-biphenyl-3-yl}-N-(cyanomethyl)-piperidine-2-carboxamide;
1-[6-fluoro-4'-(piperazin-1-yl)-1,1'-biphenyl-3-yl]-N-(cyanomethyl)-piperidine-2-carboxamide;
N-(cyanomethyl)-1-(6-bromopyridin-2-yl)piperidine-2-carboxamide;
1-[6-(4-piperazin-1-ylphenyl)pyridin-2-yl]-N-(cyanomethyl)-piperidine-2-carboxamide;
1-{6-[4-(4-tert-butoxycarbonylpiperazin-1-yl)phenyl]pyridin-2-yl}-N-(cyanomethyl)-piperidine-2-carboxamide;
1-{5-[4-(4-tert-butoxycarbonylpiperazin-1-yl)phenyl]pyridin-3-yl}-N-(cyanomethyl)-piperidine-2-carboxamide;
1-{4-fluoro-[4'-[4-(tert-butyloxycarbonyl)piperazin-1-yl]-1,1'-biphenyl-3-yl}-N-(cyanomethyl)-piperidine-2-carboxamide;
1-[4-fluoro-4'-(piperazin-1-yl)-1,1'-biphenyl-3-yl]-N-(cyanomethyl)-piperidine-2-carboxamide;

1-{5-[4-(piperazin-1-yl)phenyl]pyridin-3-yl}-N-(cyanomethyl)-piperidine-2-carboxamide;
and the pharmaceutically acceptable salts and N-oxide derivatives thereof.

7. The compound of claim 5 wherein D is aryl, heteroaryl, $C_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from $C_{1-6}$ alkyl, halo, —$OR^7$, haloalkyl, haloalkyloxy, cyano, amino, oxo, methylenedioxy, and nitro; and the pharmaceutically acceptable salts and N-oxide derivatives thereof.

8. The compound of claim 5 wherein E is aryl, heteroaryl, $C_{3-8}$ cycloalkyl or heterocyclyl wherein said aryl, heteroaryl, cycloalkyl and heterocyclyl groups, which may be monocyclic or bicyclic, are optionally substituted on either the carbon or the heteroatom with one to three substituents selected from $C_{1-6}$ alkyl, halo, —$OR^7$, haloalkyl, haloalkyloxy, cyano, amino, oxo, methylenedioxy, and nitro; and the pharmaceutically acceptable salts and N-oxide derivatives thereof.

9. The compound of claim 1 wherein X is NH;
D is an optionally substituted 5-membered ring heteroaryl wherein said heteroaryl can be substituted on either the carbon or the heteroatom with the group consisting of $C_{1-6}$ alkyl and halo;
E is selected from optionally substituted aryl, heteroaryl, $C_{3-8}$ cycloalkyl and heterocyclyl wherein said aryl, heteroaryl, cycloalkyl and heterocyclyl can be substituted with $C_{1-6}$ alkyl and halo;
and the pharmaceutically acceptable salts and N-oxide derivatives thereof.

10. The compound of claim 9 selected from:
N1-(cyanomethyl)-N2-{4-[4-(4-methylpiperazin-1-yl)phenyl]thien-3-yl}-L-leucinamide;
N1-(cyanomethyl)-N2-[4-(4-piperazin-1-ylphenyl)isothiazol-3-yl]-L-leucinamide;
N1-(cyanomethyl)-N2-(4-{4-[(dimethylamino)methyl]phenyl}thien-3-yl)-L-leucinamide;
N1(cyanomethyl)-N2-[4-(4-{[(2-hydroxyethyl)amino]methyl}phenyl)thien-3-yl]-L-leucinamide;
N1-(cyanomethyl)-N2-{4-[4-(morpholin-4-ylmethyl)phenyl]thien-3-yl}-L-leucinamide;
N2-(4-{4-[(benzylamino)methyl]phenyl}thien-3-yl)-N1-(cyanomethyl)-L-leucinamide;
N2-[4-(4-tert-butylphenyl)thien-3-yl]-N1-(cyanomethyl)-L-leucinamide;
N1-(cyanomethyl)-N2-[4-(4-isopropylphenyl)thien-3-yl]-L-leucinamide;
N1-(cyanomethyl)-N2-[3-(4-piperazin-1-ylphenyl)isoxazol-4-yl]leucinamide;
N1-(cyanomethyl)-N2-[3-(4-piperazin-1-ylphenyl)isoxazol-4-yl]-L-leucinamide;
N1-(cyanomethyl)-N2-[3-(4-piperazin-1-ylphenyl)isoxazol-4-yl]-D-leucinamide;
N1-(cyanomethyl)-N2-(4-{4-[2-(dimethylamino)ethyl]phenyl}thien-3-yl)-L-leucinamide;
N1-(1-cyanocyclopropyl)-N2-[3-(4-piperazin-1-ylphenyl)isoxazol-4-yl]-L-leucinamide;
N1-(cyanomethyl)-N2-{3-[4-(4-isopropylpiperazin-1-yl)phenyl]isoxazol-4-yl}-L-leucinamide;
N2-[4-(3-bromo-4-piperazin-1-ylphenyl)-3-methyl-isothiazol-5-yl]-N1-(cyanomethyl)leucinamide;
N1-(cyanomethyl)-N2-{4-[4-(4-isopropylpiperazin-1-yl)phenyl]isothiazol-3-yl}-L-leucinamide;
N2-[4-(3-bromo-4-piperazin-1-ylphenyl)isothiazol-3-yl]-N1-(cyanomethyl)-L-leucinamide;
N2-[4-(4-bromophenyl)isothiazol-3-yl]-N1-(cyanomethyl)-L-leucinamide;
N1-(cyanomethyl)-N2-(1-phenyl-1H-tetraazol-5-yl)-L-leucinamide;
N1-(cyanomethyl)-N2-(1-phenyl-1H-tetraazol-5-yl)-L-leucinamide;
N1-(cyanomethyl)-N2-[4-(4-iodophenyl)-3-methyl-isothiazol-5-yl]-L-leucinamide;
N1-(cyanomethyl)-N2-(3-methyl-4-phenylisothiazol-5-yl)-L-leucinamide;
N2-[4-(1,1'-biphenyl-4-yl)-3-methylisothiazol-5-yl]-N1-(cyanomethyl)-L-leucinamide;
N1-(cyanomethyl)-N2-[4-(4-piperazin-1-ylphenyl)isothiazol-5-yl]leucinamide;
N1-(cyanomethyl)-N2-[3-methyl-4-(4-pyridin-3-ylphenyl)isothiazol-5-yl]-L-leucinamide;
N1-(cyanomethyl)-N2-[3-methyl-4-(4-pyridin-4-ylphenyl)isothiazol-5-yl]-L-leucinamide;
N1-(cyanomethyl)-N2-{3-methyl-4-[4-(1-trityl-1H-imidazol-5-yl)phenyl]isothiazol-5-yl}-L-leucinamide;
N1-(cyanomethyl)-N2-{4-[4-(1H-imidazol-5-yl)phenyl]-3-methylisothiazol-5-yl}-L-leucinamide;
N1-(cyanomethyl)-N2-{3-methyl-4-[4-(1-trityl-1H-imidazol-2-yl)phenyl]isothiazol-5-yl}-L-leucinamide;
N1-(cyanomethyl)-N2-[4-(4-hydroxyphenyl)-3-methyl-isothiazol-5-yl]-L-leucinamide;
N1-(cyanomethyl)-N2-{3-methyl-4-[4-(1-oxidopyridin-4-yl)phenyl]isothiazol-5-yl}-L-leucinamide;
N1-(cyanomethyl)-N2-[4-(2-piperazin-1-ylpyridin-5-yl)isothiazol-3-yl]-L-leucinamide;
N1-(cyanomethyl)-N2-{4-[4-piperazin-1-yl-2-(trifluoromethyl)phenyl]isothiazol-3-yl}-L-leucinamide;
N1-(cyanomethyl)-N2-{4-[4-(1,4-diazepan-1-yl)phenyl]isothiazol-3-yl}-L-leucinamide;
N1-(cyanomethyl)-N2-{4-[4-(3,5-dimethylpiperazin-1-yl)phenyl]isothiazol-3-yl}-L-leucinamide;
N1-(cyanomethyl)-N2-{4-[4-(N,N-dimethylglycyl)phenyl]isothiazol-3-yl}-L-leucinamide;
N1-(cyanomethyl)-N2-(4-{4-[(2,6-dimethylpiperidin-1-yl)acetyl]phenyl}isothiazol-3-yl)-L-leucinamide;
N1-(cyanomethyl)-N2-{4-[4-(N,N-dimethylglycyl)phenyl]-3-methylisothiazol-5-yl}-L-leucinamide;
N2-{4-[4-(1-amino-1-methylethyl)phenyl]isothiazol-3-yl}-N1-(cyanomethyl)-L-leucinamide;
N2-[4-(4-acetylphenyl)-3-methylisothiazol-5-yl]-N1-(cyanomethyl)-L-leucinamide;
N2-(4-{4-[(tert-butylamino)sulfonyl]phenyl}-3-methyl-isothiazol-5-yl)-N1-(cyanomethyl)-L-leucinamide;
N1-(cyanomethyl)-N2-{3-methyl-4-[4-(piperazin-1-ylsulfonyl)phenyl]isothiazol-5-yl}-L-leucinamide;
N1-(cyanomethyl)-N2-{3-methyl-4-[4-(methylsulfonyl)phenyl]isothiazol-5-yl}-L-leucinamide;
N2-{4-[4-(aminosulfonyl)phenyl]-3-methylisothiazol-5-yl}-N1-(cyanomethyl)-L-leucinamide;
N1-(cyanomethyl)-N2-[4-(2-fluoro-4-piperazin-1-ylphenyl)-3-methylisothiazol-5-yl]-L-leucinamide;
N1-(cyanomethyl)-N2-[4-(3-fluoro-4-piperazin-1-ylphenyl)thien-3-yl]-L-leucinamide;
N1-(cyanomethyl)-N2-{4-[3-(hydroxymethyl)phenyl]thien-3-yl}-L-leucinamide;
N2-(2-bromo-4-{3-[(dimethylamino)methyl]phenyl}thien-3-yl)-N1-(cyanomethyl)-L-leucinamide;
N1-(cyanomethyl)-N2-(4-{3-[(dimethylamino)methyl]phenyl}thien-3-yl)-L-leucinamide;

N1-(cyanomethyl)-N2-{4-[3-fluoro-4-(hydroxymethyl)phenyl]thien-3-yl}-L-leucinamide;
N1-(cyanomethyl)-N2-{4-[4-(4-hydroxypiperidin-4-yl)phenyl]thien-3-yl}-L-leucinamide;
N1-(cyanomethyl)-N2-(4-{4-[(dimethylamino)methyl]-3-fluorophenyl}thien-3-yl)-L-leucinamide;
4-(4-{4-[1-(Cyanomethyl-carbamoyl)-3-methyl-butylamino]-thiophen-3-yl}-2-fluoro-benzyl)-piperazine-1-carboxylic acid tert-butyl ester;
N1-(cyanomethyl)-N2-{4-[3-fluoro-4-(piperazin-1-ylmethyl)phenyl]thien-3-yl}-L-leucinamide;
N1-(cyanomethyl)-N2-{4-[4-(pyrrolidin-1-ylmethyl)phenyl]thien-3-yl}-L-leucinamide;
N1-(cyanomethyl)-N2-[3-methyl-4-(4-piperazin-1-ylphenyl)isothiazol-5-yl]-L-leucinamide;
N1-(cyanomethyl)-N2-{4-[4-(4-isopropylpiperazin-1-yl)phenyl]-3-methylisothiazol-5-yl}-L-leucinamide;
6-{5-[1-(Cyanomethyl-carbamoyl)-3-methyl-butylamino]-3-methyl-isothiazol-4-yl}-napthalene-2-carboxylic acid methyl ester;
N1-(cyanomethyl)-N2-(3-methyl-4-{4-[4-(2,2,2-trifluoroethyl)piperazin-1-yl]phenyl}isothiazol-5-yl)-L-leucinamide;
N1-(cyanomethyl)-N2-{3-methyl-4-[4-(4-propylpiperazin-1-yl)phenyl]isothiazol-5-yl}-L-leucinamide;
N2-{4-[4-(4-acetylpiperazin-1-yl)phenyl]-3-methylisothiazol-5-yl}-N1-(cyanomethyl)-L-leucinamide;
N1-(cyanomethyl)-N2-(3-methyl-4-{4-[4-(methylsulfonyl)piperazin-1-yl]phenyl}isothiazol-5-yl)-L-leucinamide;
N2-{4-[4-(4-tert-butylpiperazin-1-yl)phenyl]-3-methylisothiazol-5-yl}-N1-(cyanomethyl)-L-leucinamide;
N2-(cyanomethyl)-N2-(4-{4-[(1S,4S)-2,5-diazabicyclo[2.2.1]hept-2-yl]phenyl}-3-methylisothiazol-5-yl)-L-leucinamide;
N1-(cyanomethyl)-N2-{4-[6-(hydroxymethyl)-2-naphthyl]-3-methylisothiazol-5-yl}-L-leucinamide;
N1-(cyanomethyl)-N2-(4-{4-[4-(2-hydroxyethyl)piperazin-1-yl]phenyl}-3-methylisothiazol-5-yl)-L-leucinamide
N1-(cyanomethyl)-N2-{4-[4-(4-cyclopropylpiperazin-1-yl)phenyl]-3-methylisothiazol-5-yl}-L-leucinamide;
N1-(cyanomethyl)-N2-(4-{4-[4-(2-methoxyethyl)piperazin-1-yl]phenyl}-3-methylisothiazol-5-yl)-L-leucinamide;
N1-(cyanomethyl)-N2-(4-{4-[4-(2-fluoroethyl)piperazin-1-yl]phenyl}-3-methylisothiazol-5-yl)-L-leucinamide;
N1-(cyanomethyl)-N2-(4-{6-[(dimethylamino)methyl]-2-naphthyl}-3-methylisothiazol-5-yl)-L-leucinamide;
N1-(cyanomethyl)-N2-{3-methyl-4-[6-(pyrrolidin-1-ylmethyl)-2-naphthyl]isothiazol-5-yl}-L-leucinamide;
N1-(cyanomethyl)-N2-(4-{4-[4-(2-hydroxypropyl)piperazin-1-yl]phenyl}-3-methylisothiazol-5-yl)-L-leucinamide;
N1-(cyanomethyl)-N2-(4-{4-[4-(2-hydroxy-2-methylpropyl)piperazin-1-yl]phenyl}-3-methylisothiazol-5-yl)-L-leucinamide;
N2-(4-{4-[4-(2-anilino-2-oxoethyl)piperazin-1-yl]phenyl}-3-methylisothiazol-5-yl)-N1-(cyanomethyl)-L-leucinamide;
N2-(4-{4-[4-(2-amino-2-oxoethyl)piperazin-1-yl]phenyl}-3-methylisothiazol-5-yl)-N1-(cyanomethyl)-L-leucinamide;
N1-(cyanomethyl)-N2-{3-methyl-4-[4-(4-methylmorpholin-2-yl)phenyl]isothiazol-5-yl}-L-leucinamide;
N1-(cyanomethyl)-N2-[3-methyl-4-(4-morpholin-4-ylphenyl)isothiazol-5-yl]-L-leucinamide;
N1-(cyanomethyl)-N2-(4-phenylthien-3-yl)-L-leucinamide;
N1-(1-cyanocyclopropyl)-N2-[4-(4-piperazin-1-ylphenyl)thien-3-yl]-L-leucinamide;
N1-(cyanomethyl)-N2-[1-methyl-4-(4-piperazin-1-ylphenyl)-1H-pyrazol-3-yl]leucinamide;
N1-(cyanomethyl)-N2-[3-methyl-4-(4-piperazin-1-ylphenyl)isothiazol-5-yl]leucinamide;
N1-(cyanomethyl)-N2-[4-(4-piperazin-1-ylphenyl)-1,2,5-oxadiazol-3-yl]leucinamide;
N1-(cyanomethyl)-N2-[4-(4-piperazin-1-ylphenyl)-1H-pyrazol-3-yl]leucinamide;
N1-(cyanomethyl)-N2-[3-methyl-4-(4-piperazin-1-ylphenyl)isoxazol-5-yl]leucinamide;
N1-(cyanomethyl)-N2-[5-methyl-4-(4-piperazin-1-ylphenyl)isoxazol-3-yl]leucinamide;
N1-(cyanomethyl)-N2-(4-{4-[(methylamino)methyl]phenyl}thien-3-yl)-L-leucinamide;
N2-(4-{4-[(tert-butylamino)methyl]phenyl}thien-3-y])-N1-(cyanomethyl)-L-leucinamide;
N1-(cyanomethyl)-N2-[4-(4-{[(2,2,2-trifluoroethyl)amino]methyl}phenyl)thien-3-yl]-L-leucinamide;
N1-(cyanomethyl)-N2-(4-{4-[1-(methylamino)ethyl]phenyl}thien-3-yl)-L-leucinamide;
N1-(cyanomethyl)-N2-(4-{4-[(isopropylamino)methyl]phenyl}thien-3-yl)-L-leucinamide;
N1-(cyanomethyl)-N2-[4-(4-{[(cyclopropylmethyl)amino]methyl}phenyl)thien-3-yl]-L-leucinamide;
N1-(cyanomethyl)-N2-(4-{4-[1-(isopropylamino)ethyl]phenyl}thien-3-yl)-L-leucinamide;
N1-(cyanomethyl)-N2-[4-(4-{[(2S)-2-(hydroxymethyl)pyrrolidin-1-yl]methyl}phenyl)thien-3-yl]-L-leucinamide;
N1-(cyanomethyl)-N2-[4-(4-{[(3-pyrrolidin-1-ylpropyl)amino]methyl}phenyl)thien-3-yl]-L-leucinamide;
N1-(cyanomethyl)-N2-{4-[4-(1H-imidazol-1-ylmethyl)phenyl]thien-3-yl}-L-leucinamide;
N1-(cyanomethyl)-N2-{4-[6-(4-methylpiperazin-1-yl)pyridin-3-yl]thien-3-yl}-L-leucinamide;
N1-(cyanomethyl)-N2-[4-(6-piperazin-1-ylpyridin-3-yl)thien-3-yl]-L-leucinamide;
N1-(cyanomethyl)-N2-{4-[4-(trifluoromethyl)phenyl]thien-3-yl}-L-leucinamide;
N2-[4-(3-bromophenyl)thien-3-yl]-N1-(cyanomethyl)-L-leucinamide;
N1-(cyanomethyl)-N2-[4-(1-naphthyl)thien-3-yl]-L-leucinamide;
N2-(5-acetyl-2,3'-bithien-4'-yl)-N1-(cyanomethyl)-L-leucinamide;
N1-(cyanomethyl)-N2-(5-methyl-2,3'-bithien-4'-yl)-L-leucinamide;
N2-[4-(4-chlorophenyl)thien-3-yl]-N1-(cyanomethyl)-L-leucinamide;
N1-(cyanomethyl)-N2-[4-(4-fluorophenyl)thien-3-yl]-L-leucinamide;
N1-(cyanomethyl)-N2-[4-(2-methylphenyl)thien-3-yl]-L-leucinamide;
N1-(cyanomethyl)-N2-[4-(4-vinylphenyl)thien-3-yl]-L-leucinamide;
N1-(cyanomethyl)-N2-[4-(3-ethoxyphenyl)thien-3-yl]-L-leucinamide;
N1-(cyanomethyl)-N2-[4-(1H-indol-5-yl)thien-3-yl]-L-leucinamide;
N1-(cyanomethyl)-N2-[4-(3-fluoro-2-methylphenyl)thien-3-yl]-L-leucinamide;
N1-(cyanomethyl)-N2-[4-(1H-pyrrol-2-yl)thien-3-yl]-L-leucinamide;

N1-(cyanomethyl)-N2-[4-(4-methylphenyl)thien-3-yl]-L-leucinamide;
N1-(cyanomethyl)-N2-(4-pyridin-3-ylthien-3-yl)-L-leucinamide;
N1-(cyanomethyl)-N2-[4-(4-methoxyphenyl)thien-3-yl]-L-leucinamide;
N1-(cyanomethyl)-N2-[4-(5-fluoro-2-methylphenyl)thien-3-yl]-L-leucinamide;
N2-(3,3'-bithien-4-yl)-N1-(cyanomethyl)-L-leucinamide;
N1-(cyanomethyl)-N2-[4-(3,5-dichlorophenyl)thien-3-yl]-L-leucinamide;
N2-{4-[3-(acetylamino)phenyl]thien-3-yl}-N1-(cyanomethyl)-L-leucinamide;
N2-[4-(4-bromophenyl)thien-3-yl]-N1-(cyanomethyl)-L-leucinamide;
N1-(cyanomethyl)-N2-{4-[4-fluoro-3-(trifluoromethyl)phenyl]thien-3-yl}-L-leucinamide;
N2-[4-(1-benzofuran-2-yl)thien-3-yl]-N1-(cyanomethyl)-L-leucinamide;
N1-(cyanomethyl)-N2-[4-(2-formylphenyl)thien-3-yl]-L-leucinamide;
N2-[4-(3-chlorophenyl)thien-3-yl]-N1-(cyanomethyl)-L-leucinamide;
N1-(cyanomethyl)-N2-[4-(2,4-dichlorophenyl)thien-3-yl]-L-leucinamide;
N1-(cyanomethyl)-N2-{4-[4-(trifluoromethyl)phenyl]thien-3-yl}-L-leucinamide;
N1-(cyanomethyl)-N2-{4-[3-(trifluoromethyl)phenyl]thien-3-yl}-L-leucinamide;
N1-(cyanomethyl)-N2-[4-(3-fluorophenyl)thien-3-yl]-L-leucinamide;
N1-(cyanomethyl)-N2-[4-(2-methoxyphenyl)thien-3-yl]-L-leucinamide;
N2-{4-[3,5-bis(trifluoromethyl)phenyl]thien-3-yl}-N1-(cyanomethyl)-L-leucinamide;
N2-[4-(3-chloro-4-fluorophenyl)thien-3-yl]-N1-(cyanomethyl)-L-leucinamide;
N1-(cyanomethyl)-N2-{4-[2-(trifluoromethyl)phenyl]thien-3-yl}-Leucinamide;
N1-(cyanomethyl)-N2-{4-[4-(methylthio)phenyl]thien-3-yl}-L-leucinamide;
N1-(cyanomethyl)-N2-[4-(3-fluoro-4-methoxyphenyl)thien-3-yl]-L-leucinamide;
N1-(cyanomethyl)-N2-[4-(3,4-dichlorophenyl)thien-3-yl]-L-leucinamide;
N2-[4-(1,3-benzodioxol-5-yl)thien-3-yl]-N1-(cyanomethyl)-L-leucinamide;
N1-(cyanomethyl)-N2-[4-(3,4-dimethoxyphenyl)thien-3-yl]-L-leucinamide;
N1-(cyanomethyl)-N2-[4-(3,4,5-trimethoxyphenyl)thien-3-yl]-L-leucinamide;
N1-(cyanomethyl)-N2-[4-(3-formyl-2-furyl)thien-3-yl]-L-leucinamide;
N1-(cyanomethyl)-N2-[4-(3-isopropoxyphenyl)thien-3-yl]-L-leucinamide;
N1-(cyanomethyl)-N2-[4-(2,3-dimethoxyphenyl)thien-3-yl]-L-leucinamide;
N1-(cyanomethyl)-N2-{4-[4-(trifluoromethoxy)phenyl]thien-3-yl}-L-leucinamide;
N1-(cyanomethyl)-N2-{4-[4-(hydroxymethyl)phenyl]thien-3-yl}-L-leucinamide;
N2-[4-(1,1'-biphenyl-3-yl)thien-3-yl]-N1-(cyanomethyl)-L-leucinamide;
N1-(cyanomethyl)-N2-[4-(3-cyanophenyl)thien-3-yl]-L-leucinamide;
N1-(cyanomethyl)-N2-[4-(1H-indol-5-yl)thien-3-yl]-L-leucinamide;
N2-[4-(5-chloro-2-methoxyphenyl)thien-3-yl]-N1-(cyanomethyl)-L-leucinamide;
N1-(cyanomethyl)-N2-[4-(2,5-dimethoxyphenyl)thien-3-yl]-L-leucinamide;
N2-[4-(4-chloro-3-fluorophenyl)thien-3-yl]-N1-(cyanomethyl)-L-leucinamide;
N1-(cyanomethyl)-N2-[4-(3,5-dimethylisoxazol-4-yl)thien-3-yl]-L-leucinamide;
N2-[4-(4-acetylphenyl)thien-3-yl]-N1-(cyanomethyl)-L-leucinamide;
N1-(cyanomethyl)-N2-[4-(4-methylphenyl)thien-3-yl]-L-leucinamide;
N1-(cyanomethyl)-N2-(4-pyrimdin-5-ylthien-3-yl)-L-leucinamide
N1-(cyanomethyl)-N2-[4-(3-nitrophenyl)thien-3-yl]-L-leucinamide;
N1-(cyanomethyl)-N2-(4-phenylthien-3-yl)-L-leucinamide;
N1-(cyanomethyl)-N2-[4-(3-methoxyphenyl)thien-3-yl]-L-leucinamide;
N1-(cyanomethyl)-N2-{4-[2-(hydroxymethyl)phenyl]thien-3-yl}-L-leucinamide;
N2-[4-(3-aminophenyl)thien-3-yl]-N1-(cyanomethyl)-L-leucinamide;
N1-(cyanomethyl)-N2-(4-pyridin-4-ylthien-3-yl)-L-leucinamide;
N1-(cyanomethyl)-N2-[4-(4-cyanophenyl)thien-3-yl]-L-leucinamide;
N2-[4-(1-benzothien-3-yl)thien-3-yl]-N1-(cyanomethyl)-L-leucinamide;
N1-(cyanomethyl)-N2-(4-quinolin-5-ylthien-3-yl)-L-leucinamide;
N1-(cyanomethyl)-N2-(4-quinolin-8-ylthien-3-yl)-L-leucinamide;
N1-(cyanomethyl)-N2-[4-(1H-pyrazol-3-yl)thien-3-yl]-L-leucinamide;
N1-(cyanomethyl)-N2-[4-(5-fluoro-2-methoxyphenyl)thien-3-yl]-L-leucinamide;
N2-[4-(1-benzothien-7-yl)thien-3-yl]-N1-(cyanomethyl)-L-leucinamide;
N1-(cyanomethyl)-N2-(4-quinolin-6-ylthien-3-yl)-L-leucinamide;
N1-(cyanomethyl)-N2-[4-(3-oxo-3-phenylpropanoyl)thien-3-yl]-L-leucinamide;
N1-(cyanomethyl)-N2-[4-(3-phenylisoxazol-5-yl)thien-3-yl]-L-leucinamide;
N1-(cyanomethyl)-N2-[4-(2-naphthyl)thien-3-yl]-L-leucinamide;
N-(cyanomethyl)-2-[(5,5-dimethyl-2-oxo-4-phenyl-2,5-dihydro-3-furanyl)amino]-4-methylpentanamide;
(2S)-N-(cyanomethyl)-4-methyl-2-({4-[4-(1-piperazinyl)phenyl]-3-thienyl}amino)pentanamide;
and the pharmaceutically acceptable salts and N-oxide derivatives thereof.

11. The compound of claim 1 wherein X is S, and the pharmaceutically acceptable salts and N-oxide derivatives thereof.

12. The compound of claim 11 selected from:
2-{[4'-(aminomethyl)-1,1'-biphenyl-4-yl]thio}-N-(cyanomethyl)-4-methylpentanamide;
2-(1,1'-biphenyl-4-ylthio)-N-(cyanomethyl)-4-methylpentanamide;
N-(cyanomethyl)-2-{[4'-(ydroxymethyl)-1,1'-biphenyl-4-yl]thio}-4-methylpentanamide;
N-(cyanomethyl)-4-methyl-2-[(4'-piperidin-1-yl-1,1'-biphenyl-4-yl)thio]pentanamide;

2-({4'-[(benzylamino)methyl]-1,1'-biphenyl-4-yl}thio)-N-(cyanomethyl)-4-methylpentanamide;
N-(cyanomethyl)-2-({4'-[(cyclopropylamino)methyl]-1,1'-biphenyl-4-yl}thio)-4-methylpentanamide;
N-(cyanomethyl)-4-methyl-2-[(4'-{[(1-methylpiperidin-4-yl)amino]methyl}-1,1'-biphenyl-4-yl)thio]pentanamide;
N-(cyanomethyl)-2-({4'-[(dicyclobutylamino)methyl]-1,1'-biphenyl-4-yl}thio)-4-methylpentanamide;
N-(cyanomethyl)-2-({4'-[(dicyclopentylamino)methyl]-1,1'-biphenyl-4-yl}thio)-4-methylpentanamide;
N-(cyanomethyl)-2-({4'-[(cyclopentylamino)methyl]-1,1'-biphenyl-4-yl}thio)-4-methylpentanamide;
N-(cyanomethyl)-4-methyl-2-[(4-piperazin-1-ylphenyl)thio]pentanamide;
N-(cyanomethyl)-2-[(3',5'-difluoro-1,1'-biphenyl-4-yl)thio]-4-methylpentanamide;
2-{[4-(5-chlorothien-2-yl)phenyl]thio}-N-(cyanomethyl)-4-methylpentanamide;
N-(cyanomethyl)-4-methyl-2-{[4'-(trifluoromethyl)-1,1'-biphenyl-4-yl]thio}pentanamide;
N-(cyanomethyl)-4-methyl-2-[(3'-methyl-1,1'-biphenyl-4-yl)thio]pentanamide;
N-(cyanomethyl)-4-methyl-2-[(4-quinolin-5-ylphenyl)thio]pentanamide;
2-{[4-(1-benzothien-3-yl)phenyl]thio}-N-(cyanomethyl)-4-methylpentanamide;
N-(cyanomethyl)-4-methyl-2-[(4-quinolin-8-ylphenyl)thio]pentanamide;
2-[(4'-cyano-1,1'-biphenyl-4-yl)thio]-N-(cyanomethyl)-4-methylpentanamide;
N-(cyanomethyl)-4-methyl-2-{[4-(1H-pyrazol-3-yl)phenyl]thio}pentanamide;
N-(cyanomethyl)-2-[(5'-fluoro-2'-methoxy-1,1'-biphenyl-4-yl)thio]4-methylpentanamide;
2-{[4-(1-benzothien-7-yl)phenyl]thio}-N-(cyanomethyl)-4-methylpentanamide;
N-(cyanomethyl)-4-methyl-2-[(4-quinolin-6-ylphenyl)thio]pentanamide;
N-(cyanomethyl)-2-[(3'-fluoro-4'-piperazin-1-yl-1,1'-biphenyl-4-yl)thio]-4-methylpentanamide;
N-(cyanomethyl)-2-{[4'-(4-ethylpiperazin-1-yl)-1,1'-biphenyl-4-yl]thio}-4-methylpentanamide;
N-(cyanomethyl)-2-[(3'-ethyl-4'-piperazin-1-yl-1,1'-biphenyl-4-yl)thio]-4-methylpentanamide;
N-(cyanomethyl)-4-methyl-2-[(4-{2-[(4-propylpiperazin-1-yl)carbonyl]-1H-indol-5-yl}phenyl)thio]pentanamide;
N-(cyanomethyl)-4-methyl-2-[(4-{2-[(4-methylpiperazin-1-yl)carbonyl]-1H-indol-5-yl}phenyl)thio]pentanamide;
N-(cyanomethyl)-4-methyl-2-({4-[2-(piperazin-1-ylcarbonyl)-1H-indol-5-yl]phenyl}thio)pentanamide;
N-(cyanomethyl)-4-methyl-2-{[4'-(4-methoxypiperidin-4-yl)-1,1'-biphenyl-4-yl]thiol}-4-methylpentanamide;
N-(cyanomethyl)-4-methyl-2-{[4-(2-piperazin-1-ylpyrimidin-5-yl)phenyl]thio}pentanamide;
N-(cyanomethyl)-4-methyl-2-{[4'-piperazin-1-yl-2'-(trifluoromethyl)-1,1'-biphenyl-4-yl]thio}pentanamide;
N-(cyanomethyl)-1-{[4'-(4-ethylpiperazin-1-yl)-1,1'-biphenyl-4-yl]thio}cyclohexanecarboxamide;
N-(cyanomethyl)-2-{[4'-(2,6-dimethylpiperazin-1-yl)-1,1'-biphenyl-4-yl]thio}-4-methylpentanamide;
N-(cyanomethyl)-2-({4-[5-(2-hydroxyethyl)-4-methyl-1,3-thiazol-2-yl]phenyl}thio)-4-methylpentanamide;
2-[(4'-acetyl-1,1'-biphenyl-4-yl)thio]-N-(cyanomethyl)-4-methylpentanamide;
N-(cyanomethyl)-3-(1-methylcyclopropyl)-2-[(4'-piperazin-1-yl-1,1'-biphenyl-4-yl)thio]propanamide;
N-(cyanomethyl)-2-{[4-(1H-imidazol-4-yl)phenyl]thio}-4-methylpentanamide;
(2R)-N-(cyanomethyl)-4-methyl-2-[(4'-piperazin-1-yl-1,1'-biphenyl-4-yl)thio]pentanamide;
(2S)-N-(cyanomethyl)-4-methyl-2-[(4'-piperazin-1-yl-1,1'-biphenyl-4-yl)thio]pentanamide;
N-(cyanomethyl)-1-[(4'-piperazin-1-yl-1,1'-biphenyl-4-yl)thio]cyclohexanecarboxamide;
N-(cyanomethyl)-4-methyl-2-[(4'-{[2-(trimethylsilyl)ethyl]sulfonyl}-1,1'-biphenyl-4-yl)thio]pentanamide;
2-{[4-(4-chlorophenyl)-1,2,3-thiadiazol-5-yl]thio}-N-(cyanomethyl)-4-methylpentanamide;
N-(cyanomethyl)-4-methyl-2-[(3-methyl-1-phenyl-1H-pyrazol-5-yl)thio]pentanamide;
2-[(4-bromo-3-methyl-1-phenyl-1H-pyrazol-5-yl)thio]-N-(cyanomethyl)-4-methylpentanamide;
N-(cyanomethyl)-4-methyl-2-[(5-phenyl-4H-1,2,4-triazol-3-yl)sulfanyl]pentanamide;
N-(cyanomethyl)-4-methyl-2-{[4'-(1-piperazinyl)[1,1'-biphenyl]-3-yl]sulfanyl}pentanamide;
N-(cyanomethyl)-4-methyl-2-{[4'-(1-piperazinyl)[1,1'-biphenyl]-2-yl]sulfanyl}pentanamide;
1-[(2-bromophenyl)sulfanyl]-N-(cyanomethyl)cyclohexanecarboxamide;
N-(cyanomethyl)-4-methyl-2-{[4'-(1-piperazinyl)[1,1'-biphenyl]-4-yl]sulfanyl}pentanamide;
1-[(3-bromophenyl)sulfanyl]-N-(cyanomethyl)cyclohexanecarboxamide;
N-(cyanomethyl)-1-{[4'-(1-piperazinyl)[1,1'-biphenyl]-2-yl]sulfanyl}cyclohexanecarboxamide;
N-(cyanomethyl)-1-{[4'-(1-piperazinyl)[1,1'-biphenyl]-3-yl]sulfanyl}cyclohexanecarboxamide; and the pharmaceutically acceptable salts and N-oxide derivatives thereof.

13. The compound of claim 1 selected from:
N-(cyanomethyl)-4-methyl-2-[(4-piperazin-1-ylbenzyl)thio]pentanamide;
N-(cyanomethyl)-4-methyl-2-{[(4'-piperazin-1-yl-1,1'-biphenyl-4-yl)methyl]thio}pentanamide;
(2S)-N-(cyanomethyl)-4-methyl-2-{[4'-(1-piperazinyl)[1,1'-biphenyl]-4-yl]amino}pentanamide;
(2S)-N-(cyanomethyl)-4-methyl-2-{[4'-(1-piperazinyl)[1,1'-biphenyl]-3-yl]amino}pentanamide;
1-(3-bromoanilino)-N-(cyanomethyl)cyclohexanecarboxamide;
(2S)-N-(cyanomethyl)-4-methyl-2-{[4'-(1-piperazinyl)[1,1'-biphenyl]-2-yl]amino}pentanamide;
(2S)-N-(cyanomethyl)-4-methyl-2-({4'-[2-(4-methyl-1-piperazinyl)-1,3-thiazol-4-yl][1,1'-biphenyl]-3-yl}amino)pentanamide;
(2S)-N-(cyanomethyl)methyl-2-({4'-[2-(4-methyl-1-piperazinyl)-1,3-thiazol-4-yl][1,1'-biphenyl]-2-yl}amino)pentanamide;
N-(cyanomethyl)-4-methyl-2-({3-[4-(1-piperazinyl)phenyl]-2-pyridinyl}oxy)pentanamide;
(2S)-N-(cyanomethyl)-4-methyl-2-({5-[4-(1-piperazinyl)phenyl]-2-pyridinyl}amino)pentanamide;
2-([1,1'-biphenyl]-4-ylmethoxy)-N-(cyanomethyl)-4-methylpentanamide;
N-(cyanomethyl)-4-methyl-2-{[4'-(1-piperazinyl)[1,1'-biphenyl]-4-yl]sulfonyl}pentanamide;
N-(cyanomethyl)-4-methyl-2-{[4'-(1-piperazinyl)[1,1'-biphenyl]-3-yl]sulfonyl}pentanamide;
N-(cyanomethyl)-4-methyl-2-{[4'-(1-piperazinyl)[1,1'-biphenyl]-2-yl]sulfonyl}pentanamide;
N-(cyanomethyl)-4-methyl-2-({5-[4-(1-piperazinyl)phenyl]-2-pyrinidinyl}amino)pentanamide;
N-(cyanomethyl)-1-{[4'-(1-piperazinyl)[1,1'-biphenyl]-3-yl]amino}cyclohexanecarboxamide;

triisopropylsilyl 4-[3'-(1-{[(cyanomethyl)amino]carbonyl}-3-methylbutoxy)[1,1'-biphenyl]-4-yl]-1-piperazinecarboxylate;
triisopropylsilyl 4-[4'-(1-{[(cyanomethyl)amino]carbonyl}-3-methylbutoxy)[1,1'-biphenyl]-4-yl]-1-piperazinecarboxylate;
N-(cyanomethyl)-1-{[4'-(1-piperazinyl)[1,1'-biphenyl]-4-yl]amino}cyclohexanecarboxamide;
N-(cyanomethyl)-4-methyl-2-{[4'-(1-piperazinyl)[1,1'-biphenyl]-3-yl]oxy}pentanamide;
N-(cyanomethyl)-4-methyl-2-{[4'-(1-piperazinyl)(1,1'-biphenyl]-4-yl]oxy}pentanamide;
N-(cyanomethyl)-1-{[4'-(1-piperazinyl)[1,1'-biphenyl]-2-yl]amino}cyclohexanecarboxamide;
N-(cyanomethyl)-4-methyl-2-{[4'-(1-piperazinyl)[1,1'-biphenyl]-2-yl]oxy}pentanamide;
N-(cyanomethyl)-4-methyl-2-{[4'-(1-piperazinyl)[1,1'-biphenyl]-2-yl]methyl}pentanamide;
N-(cyanomethyl)-4-methyl-2-{[4'-(1-piperazinyl)[1,1'-biphenyl]-3-yl]methyl}pentanamide;
N-(cyanomethyl)-4-methyl-2-{[4'-(1-piperazinyl)[1,1'-biphenyl]-4-yl]methyl}pentanamide;
(2S)-N-(cyanomethyl)-4-methyl-2-({2-methyl-3-oxo-5-[4-(1-piperazinyl)phenyl]-2,3-dihydro-4-pyridazinyl}amino)pentanamide;
(2S)-N-(cyanomethyl)-4-methyl-2-({[4'-(1-piperazinyl)[1,1'-biphenyl]-3-yl]methyl}amino)pentanamide;
(2S)-N-(cyanomethyl)-4-methyl-2-({[4'-(1-piperazinyl)[1,1'-biphenyl]-4-yl]methyl}amino)pentanamide;
tert-butyl 4-{3'-[(1-{[(cyanomethyl)amino]carbonyl}-3-methylbutoxy)methyl][1,1'-biphenyl]-4-yl}-1-piperazinecarboxylate;
tert-butyl 4-{4'-[(1-{[(cyanomethyl)amino]carbonyl}-3-methylbutoxy)methyl][1,1'-biphenyl]-4-yl}-1-piperazinecarboxylate;
tert-butyl 4-{2'-[(1-{[(cyanomethyl)amino]carbonyl}-3-methylbutoxy)methyl][1,1'-biphenyl]-4-yl}-1-piperazinecarboxylate;
N-(cyanomethyl)-4-methyl-2-{[4'-(1-piperazinyl)[1,1'-biphenyl]-2-yl]methoxy}pentanamide;
N-(cyanomethyl)-4-methyl-2-{[4'-(1-piperazinyl)[1,1'-biphenyl]-3-yl]methoxy}pentanamide;
N-(cyanomethyl)-4-methyl-2-{[4'-(1-piperazinyl)[1,1'-biphenyl]-4-yl]methoxy}pentanamide;
[(3S)-3-isobutyl-2-oxo-2,3-dihydroimidazo[2,1-a]thieno[3,4-c]isoquinolin-1(11bH)-yl]acetonitrile;
[(3S)-3-isobutyl-2-oxo-2,3-dihydrofuro[3,2-c]imidazo[1,2-a]thieno[3,4-e]pyridin-1(10bH)-yl]acetonitrile;
N1-(cyanomethyl)-N2-(2,2,3,3-tetrafluoro-1-phenylcyclopropyl)-L-leucinamide;
N1-(cyanomethyl)-N2-(3,3,4,4-tetrafluoro-1-phenylcyclopentyl)-L-leucinamide;
N1-(cyanomethyl)-N2-(2,2-difluoro-5-phenylcyclopentyl)-L-leucinamide;
N1-(cyanomethyl)-N2-(2,2-difluoro-2,3-dihydro-1H-inden-1-yl)-L-leucinamide;
N1-(cyanomethyl)-N2-{1-[4-(N,N-dimethylglycyl)phenyl]cyclopropyl}-L-leucinamide;
1-{4-[2-(4-methyl-piperazin-1-yl)-thiazol-4-yl]-phenoxy}-cyclohexanecarboxylic acid cyanomethylamide;
2-(biphenyl-3-yloxy)-4-methyl-pentanoic cyanomethylamide;
2-(biphenyl-4-yloxy)-4-methyl-pentanoic cyanomethylamide;
and the pharmaceutically acceptable salts and N-oxide derivatives thereof.

14. $N^1$-(cyanomethyl)-$N^2$-[3-methyl-4-(4-piperazin-1-ylphenyl)isothiazol-5-yl]-L-leucinamide and the pharmaceutically acceptable salts and N-oxide derivatives thereof.

15. $N^1$-(cyanomethyl)-$N^2$-(4-{4-[4-(2-hydroxyethyl)piperazin-1-yl]phenyl}-3-methylisothiazol-5-yl)-L-leucinamide and the pharmaceutically acceptable salts and N-oxide derivatives thereof.

16. (4S)-1-{4-chloro-4'-[(dimethylamino)methyl]-1,1'-biphenyl-3-yl}-N-(cyanomethyl)-4-methyl-L-prolinamide and the pharmaceutically acceptable salts and N-oxide derivatives thereof.

17. (4S)-1-(4-chloro-4'-piperazin-1-y]-1,1'-biphenyl-3-yl)-N-(cyanomethyl)-4-methyl-L-prolinamide and the pharmaceutically acceptable salts and N-oxide derivatives thereof.

18. N-(cyanomethyl)-4-methyl-2-{[4'-(1-piperazinyl)[1,1'-biphenyl]-4-yl]sulfanyl}pentanamide and the pharmaceutically acceptable salts and N-oxide derivatives thereof.

19. A pharmaceutical composition comprising a compound according to claim 1 and a pharmaceutically acceptable carrier.

20. A pharmaceutical composition made by combining a compound according to claim 1 and a pharmaceutically acceptable carrier.

21. A process for making a pharmaceutical composition comprising combining a compound according to claim 1 and a pharmaceutically acceptable carrier.

22. A method of inhibiting cathepsin activity in a mammal in need thereof, comprising administering to the mammal a therapeutically effective amount of a compound according to claim 1.

23. The method according to claim 11 wherein the cathepsin activity is Cathepsin K activity.

24. A method of treating or preventing bone loss in a mammal in need thereof by administering to the mammal a therapeutically effective amount of a compound according to claim 1.

25. A method of treating or preventing osteoporosis in a mammal in need thereof by administering to the mammal a therapeutically effective amount of a compound according to claim 1.

26. A method of treating cathepsin dependent conditions in a mammal in need thereof by administering to the mammal a therapeutically effective amount of a compound according to claim 1.

27. A pharmaceutical composition comprising a compound of claim 1 and another agent selected from: an organic bisphosphonate, an estrogen receptor modulator, an androgen receptor modulator, an inhibitor of osteoclast proton ATPase, an inhibitor of HMG-CoA reductase, an integrin receptor antagonist, or an osteoblast anabolic agent, and the pharmaceutically acceptable salts and mixtures thereof.

28. A method of treating osteoporosis comprising a compound of claim 1 and another agent selected from: an organic bisphosphonate, an estrogen receptor modulator, an androgen receptor modulator, an inhibitor of osteoclast proton ATPase, an inhibitor of HMG-CoA reductase, an integrin receptor antagonist, or an osteoblast anabolic agent, and the pharmaceutically acceptable salts and mixtures thereof.

29. A method of treating bone loss comprising a compound of claim 1 and another agent selected from: an organic bisphosphonate, an estrogen receptor modulator, an androgen receptor modulator, an inhibitor of osteoclast proton ATPase, an inhibitor of HMG-CoA reductase, an integrin receptor antagonist, or an osteoblast anabolic agent, and the pharmaceutically acceptable salts and mixtures thereof.

* * * * *

UNITED STATES PATENT AND TRADEMARK OFFICE
CERTIFICATE OF CORRECTION

| | | |
|---|---|---|
| PATENT NO. | : 7,012,075 B2 | Page 1 of 1 |
| APPLICATION NO. | : 10/469430 | |
| DATED | : March 14, 2006 | |
| INVENTOR(S) | : Petpihoon Prasit et al. | |

It is certified that error appears in the above-identified patent and that said Letters Patent is hereby corrected as shown below:

On Title Page, Col. 1, (73) Assignees, delete "Merck & Co., Inc." and insert therefore -- Merck Frosst Canada & Co. --.

Signed and Sealed this

First Day of August, 2006

JON W. DUDAS
*Director of the United States Patent and Trademark Office*